US009408890B2

(12) United States Patent
Comolli et al.

(10) Patent No.: US 9,408,890 B2
(45) Date of Patent: Aug. 9, 2016

(54) MULTIVALENT LIPOSOME FORMULATIONS

(71) Applicant: The Charles Stark Draper Laboratory, Inc., Cambridge, MA (US)

(72) Inventors: James Comolli, Boxborough, MA (US); Jose Trevejo, Brighton, MA (US); Ram Sasisekharan, Cambridge, MA (US); Zachary Shriver, Winchester, MA (US); Karthik Viswanathan, Waltham, MA (US); Deborah Fygenson, Santa Barbara, CA (US); Robert Finberg, Newtonville, MA (US); Jennifer Wang, Shrewsbury, MA (US)

(73) Assignees: The Charles Stark Draper Laboratory, Inc., Cambridge, MA (US); The Massachusetts Institute of Technology, Cambridge, MA (US); University of California, Santa Barbara (UCSB), Santa Barbara, CA (US); University of Massachusetts Medical School, Boston, MA (US)

( * ) Notice: Subject to any disclaimer, the term of this patent is extended or adjusted under 35 U.S.C. 154(b) by 0 days.

(21) Appl. No.: 14/161,555

(22) Filed: Jan. 22, 2014

(65) Prior Publication Data

US 2014/0255470 A1 Sep. 11, 2014

Related U.S. Application Data

(60) Provisional application No. 61/755,394, filed on Jan. 22, 2013.

(51) Int. Cl.

| | |
|---|---|
| *A61K 9/127* | (2006.01) |
| *A61K 38/16* | (2006.01) |
| *A61K 47/48* | (2006.01) |
| *A61K 31/7012* | (2006.01) |

(52) U.S. Cl.

CPC .......... *A61K 38/162* (2013.01); *A61K 31/7012* (2013.01); *A61K 47/48815* (2013.01)

(58) Field of Classification Search

None

See application file for complete search history.

(56) References Cited

U.S. PATENT DOCUMENTS

| | | | | |
|---|---|---|---|---|
| 5,591,448 | A | 1/1997 | Tepic | |
| 2002/0102236 | A1 | 8/2002 | Taylor et al. | |
| 2010/0004195 | A1 | 1/2010 | Sasisekharan et al. | |
| 2013/0129636 | A1 * | 5/2013 | Kamaly et al. | 424/9.321 |

FOREIGN PATENT DOCUMENTS

| | | | |
|---|---|---|---|
| WO | WO-89/05633 | A1 | 6/1989 |

OTHER PUBLICATIONS http://en.wikipedia.org/wiki/Sialic_acid, "Sialic Acid", authors unknown, published online by Wikipedia Foundation, San Francisco, CA, downloaded Apr. 20, 2015 as a PDF version, 5 pages long.* http://en.wikipedia.org/wiki/Virus, authors unknown, published online by Wikipedia Foundation, San Francisco, CA, downloaded Apr. 20, 2015 as a PDF version, 27 pages long.* http://www.wisegeek.org/how-many-species-of-bacteria-are-there.htm, Author(s) unknown, Published by WiseGeek, Sparks, NV, downloaded Apr. 20, 2015, 4 pages long.*

Alford, et al., Fusion of Influenza Virus with Sialic Acid-Bearing Target Membranes, Biochemistry, vol. 33, No. 8, pp. 1977-1987 (1994).

Hendricks, et al., Sialylneolacto-N-tetraose c (LSTc)-bearing Liposomal Decoys Capture Influenza A Virus, Journal of Biological Chemistry. vol. 288, No. 12, pp. 8061-8073 (Jan. 28, 2013).

International Search Report and Written Opinion mailed Mar. 27, 2014 in PCT Application No. PCT/US2014/012577 (13 pages), John Tatjana.

* cited by examiner

*Primary Examiner* — Robert M Kelly

(74) *Attorney, Agent, or Firm* — Edward A. Gordon; Paul S. Hunter; Foley & Lardner LLP

(57) ABSTRACT

This disclosure provides compositions, kits, and methods useful for treating or preventing viral and bacterial infection and reducing or preventing the effects of toxins. The methods comprise administering to a subject an effective amount of a liposomal composition.

17 Claims, 16 Drawing Sheets

| Compound | Full Name | Purpose |
|---|---|---|
| LSTc-DOPE | LSTc-1,2-dioleoyl-sn-glycero-3-phosphoethanolamine | Glycolipid. Mimics the influenza receptor |
| DOPE-NBD or -Rh | 1,2-dioleoyl-sn-glycero-3-phosphoethanolamine-N-(7-nitro-2-1,3-benzoxadiazol-4-yl) or -rhodamine | Fluorescent lipid. Enables quantification and tracking of decoys |
| DOPG | 1, 2-dioleoyl-sn-glycero-3-[phospho-rac-(1-glycerol)] | Negatively charged lipid. Maintains decoy charge when varying mol% LSTc-DOPE |
| DOPC | 1, 2-dioleoyl-sn-glycero-3-phosphocholine | Neutral lipid. Constitutes majority of decoy |

B.

201

202

203

204

205

206

A.

B.

F.

MULTIVALENT LIPOSOME FORMULATIONS

CROSS-REFERENCE TO RELATED APPLICATIONS

This application claims priority to U.S. Application No. 61/755,394 filed Jan. 22, 2013. The entire contents of the application listed above are hereby incorporated by reference in their entirety.

GOVERNMENT SUPPORT

This invention was made with government support under contract number W911NF-10-1-0268 awarded by the Defense Advanced Research Projects Agency, Defense Sciences Office. The government has certain rights in the invention.

BACKGROUND

The following description is provided to assist the understanding of the reader. None of the information provided or references cited is admitted to be prior art to the present technology.

Viral and bacterial infections are a major cause of illness. Many strains of viruses and bacteria are prone to developing drug resistance due to the high mutation rate in the viral and bacterial genome.

Viruses and bacteria are known to bind to compounds on the cell surface to facilitate entry into the cell. For example, influenza uses many individually weak ligand-binding interactions for a high-avidity multivalent attachment to sialic acid-bearing cells.

SUMMARY

In one aspect, the present technology provides compositions that have a first population of lipids, a second population of lipids, cholesterol, and at least two binding targets, wherein the binding targets are linked to the first population of lipids to form BT-lipids, wherein the BT-lipids, the second population of lipids, and cholesterols form a liposome, wherein the binding targets are displayed on the outer surface of the liposome, wherein the first and second population of lipids have a phase transition temperature below 41° C., and wherein the cholesterol comprises 15 to 30 mol % of the liposome. In some implementations, the first population of lipids and the second population of lipids are the same. In another implementation, the first population of lipids and the second population of lipids are different.

In some implementations, the binding targets are specific for influenza A. In some implementations, the influenza A binding targets are one or more binding targets selected from the group consisting of LSTc, α-5-N-acetyl-neuraminic acid (Neu5Ac), Neu5Acα2-3Galβ1-4GlcNAc, Neu5Acα2-6Galβ1-4GlcNAc, Neu5Acα2-3Galβ1-4GlcNAβ1-3Galβ14GlcNAc, Neu5Acα2-6Galβ1-4GlcNAcβ1-3Galβ1-4GlcNAc, Neu5Acα2-3Galβ1-4GlcNAcβ1-3Galβ1-4GlcNAcβ1-3Galβ1-4GlcNAc, Neu5Acα6Galβ4GlcNAcβ3Galβ4Glc, Neu5Acα3Galβ4GlcNAc, Neu5Acα6Galβ4GlcNAc, Neu5Acα3Gal, Neu5Acα6Gal, Neu5Acα3Galβ4Glc, Neu5Acα3Galβ3GlcNAc, Neu5Acα2-6Galβ1-4GlcNAcβ1-3Galβ1-4GlcNAc-, Neu5Acα2-6GalNAcβ1-4GlcNAcβ1-3GalNAcβ1-4GlcNAc-, Neu5Acα2-6GlcNAcβ1-3Galβ1-3/4GlcNAc-, Neu5Acα2-6Galβ1-4GlcNAcβ1-3Galβ1-3GalNAcα, Neu5Acα2-6Galβ1-4GlcNAcβ1-3Galβ1-4GlcNAcβ1-3Galβ1-3GalNAcα, Neu5Acα2-6GalNAcβ1-4GlcNAcβ1-3Galβ1-3GalNAcα, Neu5Acα2-6GalNAcβ1-4GlcNAcβ1-3GalNAcβ1-4GlcNAcβ1-3Galβ1-3GalNAcα, Neu5Acα2-6GalNAcα-β1-3Galα2-3Neu5Ac, Neu5Acα2-6Galβ1-4GlcNAcβ1-3/6GalNAcα, Neu5Acα2-6Galβ1-4GlcNAcβ1-3Galβ1-4GlcNAcβ1-3/6GalNAcα, Neu5Acα2-6GalNAcβ1-4GlcNAcβ1-3/6GalNAcα, Neu5Acα2-6GalNAcβ1-4GlcNAcβ1-3GalNAcβ1-4GlcNAcβ1-3/6GalNAcα, Neu5Acα2-6Galβ1-4GlcNAcβ1-6GalNAcα-β1-3Galα2-3Neu5Ac, Neu5Acα2-6Galβ1-4GlcNAcβ1-3/6GalNAcα-β1-3/6GlcNAcβ1-4Galα2-3/6Neu5Ac, Neu5Acα2-6GlcNAcβ1-3Galβ1-4GlcNAcβ1-3Galβ1-3GalNAc, Neu5Acα2-6GlcNAcβ1-3Galβ1-3GlcNAcβ1-3/6GalNAc, Neu5Acα2-6GlcNAcβ1-3Galβ1-4GlcNAcβ1-3/6GalNAc, Neu5Acα2-6Galβ1-3GalNAcβ1-4Galα1-3Galβ1-4Glc, Neu5Acα2-6Galβ1-4GlcNAcβ1-3Galβ1-4Glc, Neu5Acα2-6Galβ1-3GalNAcβ1-3Galα1-4Galβ1-4Glc, Neu5Acα2-6Galβ1-3GlcNAcβ1-3Galβ1-4Glc, Neu5α2-6Galβ1-4GlcNAcβ1-3GalNAcα, Neu5Acα2-6Galβ1-4GlcNAcβ1-3Gal~1-3GalNAcα, Neu5Acα2-6GalNAc(β1-3Gal)β1-4Galβ1-4Glc, and Neu5Acα2-6GalNAc(β1-3Gal-)β1-3Galα1-4Galβ1-4Glc.

In some implementations, the first population and second population of lipids is selected from the group consisting of 12:0 phosphatidylcholine (PC) (DLPC), 13:0 PC, 14:0 PC (DMPC), 15:0 PC, 16:0 PC (DPPC), 16:1 PC, 18:1c9 PC (DOPC), 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC (POPC), 16:0-22:6 PC, 18:0-14:0 PC, 18:0-18:1 PC, 18:1-16:0 PC, 18:1-18:0 PC, 12:0 phosphatidylglycerol (PG) (DLPG); 14:0 PG (DMPG), 16:0 PG (DPPG), 18:1 PG (DOPG), 16:0-18:1 PG (POPG), 14:0 phosphatidylserine (PS) (DMPS), 18:1 PS (DOPS), 16:0-18:1 PS (POPS), 12:0 phosphatidic acid (PA) (DLPA), 18:1 PA (DOPA), 16:0-18:1 PA (POPA), 12:0 phosphatidylethanolamine (PE) (DLPE), 18:1c9 PE (DOPE), 18:1t9 PE, 18:2 PE, 18:3 PE, 16:0-18:1 PE (POPE), or a combination thereof. In some implementations, the second population of lipids are 18:1 lipids. In another implementation, the second population of lipids is selected from the group consisting of DOPE, DOPC, DOPG, or a combination thereof.

In some implementations, the BT-lipids comprises LSTc linked to DOPE and wherein the second population of lipids is selected from the group consisting of DOPE, DOPC, DOPG, or a combination thereof.

In another aspect, the present technology provides methods for making a liposome composition including linking at least one binding target (BT) to a lipid to form a BT-lipid, combining a plurality of BT-lipids, a second population of lipids, and cholesterol, and forming a liposome, wherein the BT-lipid and second population of lipids have a phase transition temperature below 41° C., and wherein the cholesterol is about 15 to 30 mol % of the liposome.

In some implementations, the lipid in the BT-lipid and the lipids in the second population of lipids are selected from the group consisting of 12:0 phosphatidylcholine (PC) (DLPC), 13:0 PC, 14:0 PC (DMPC), 15:0 PC, 16:0 PC (DPPC), 16:1 PC, 18:1c9 PC (DOPC), 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC (POPC), 16:0-22:6 PC, 18:0-14:0 PC, 18:0-18:1 PC, 18:1-16:0 PC, 18:1-18:0 PC, 12:0 phosphatidylglycerol (PG) (DLPG); 14:0 PG (DMPG), 16:0 PG (DPPG), 18:1 PG (DOPG), 16:0-18:1 PG (POPG), 14:0 phosphatidylserine (PS) (DMPS), 18:1 PS (DOPS), 16:0-18:1 PS (POPS), 12:0 phosphatidic acid (PA) (DLPA), 18:1

PA (DOPA), 16:0-18:1 PA (POPA), 12:0 phosphatidylethanolamine (PE) (DLPE), 18:1c9 PE (DOPE), 18:1t9 PE, 18:2 PE, 18:3 PE, 16:0-18:1 PE (POPE), or a combination thereof. In some implementations, the second population of lipids consist of 18:1 lipids. In some implementations, the 18:1 lipids are selected from DOPE, DOPC, DOPG, or a combination thereof.

In some implementations, the binding targets are one or more binding targets selected from the group consisting of LSTc, α-5-N-acetyl-neuraminic acid (Neu5Ac), Neu5Acα2-3Galβ1-4GlcNAc, Neu5Acα2-6Galβ1-4GlcNAc, Neu5Acα2-3Galβ1-4GlcNAβ1-3Galβ14GlcNAc, Neu5Acα2-6Galβ1-4GlcNAcβ1-3Galβ1-4GlcNAc, Neu5Acα2-3Galβ1-4GlcNAcβ11-3Galβ1-4GlcNAcβ1-3Galβ1-4GlcNAc, Neu5Acα6Galβ4GlcNAcβ3Galβ4Glc, Neu5Acα3Galβ4GlcNAc, Neu5Acα6Galβ4GlcNAc, Neu5Acα3Gal, Neu5Acα6Gal, Neu5Acα3Galβ4Glc, Neu5Acα3Galβ3GlcNAc, Neu5Acα2-6Galβ1-4GlcNAcβ1-3Galβ1-4GlcNAc-, Neu5Acα2-6GalNAcβ1-4GlcNAcβ1-3GalNAcβ1-4GlcNAc-, Neu5Acα2-6GlcNAcβ1-3Galβ1-3/4GlcNAc-, Neu5Acα2-6Galβ1-4GlcNAcβ1-3Galβ1-3GalNAcα, Neu5Acα2-6Galβ1-4GlcNAcβ1-3Galβ1-4GlcNAcβ1-3Galβ1-3GalNAcα, Neu5Acα2-6GalNAcβ1-4GlcNAcβ1-3Galβ1-3GalNAcα, Neu5Acα2-6GalNAcβ1-4GlcNAcβ1-3GalNAcβ1-4GlcNAcβ1-3Galβ1-3GalNAcα, Neu5Acα2-6GalNAcα-β1-3Galα2-3Neu5Ac, Neu5Acα2-6Galβ1-4GlcNAcβ1-3/6GalNAcα, Neu5Acα2-6Galβ1-4GlcNAcβ1-3Galβ1-4GlcNAcβ1-3/6GalNAcα, Neu5Acα2-6GalNAcβ1-4GlcNAcβ1-3/6GalNAcα, Neu5Acα2-6GalNAcβ1-4GlcNAcβ1-3GalNAcβ1-4GlcNAcβ1-3/6GalNAcα, Neu5Acα2-6Galβ1-4GlcNAcβ1-6GalNAcα-β1-3Galα2-3Neu5Ac, Neu5Acα2-6Galβ1-4GlcNAcβ1-3/6GalNAcα-β1-3/6GlcNAcβ1-4Galα2-3/6Neu5Ac, Neu5Acα2-6GlcNAcβ1-3Galβ1-4GlcNAcβ1-3Galβ1-3GalNAc, Neu5Acα2-6GlcNAcβ1-3Galβ1-3GlcNAcβ1-3/6GalNAc, Neu5Acα2-6GlcNAcβ1-3Galβ1-4GlcNAcβ1-3/6GalNAc, Neu5Acα2-6Galβ1-3GalNAcβ1-4Galα1-3Galβ1-4Glc, Neu5Acα2-6Galβ1-4GlcNAcβ1-3Galβ1- 4Glc, Neu5Acα2-6Galβ1-3GalNAcβ1-3Galα1-4Galβ1-4Glc, Neu5Acα2-6Galβ1-3GlcNAcβ1-3Galβ1-4Glc, Neu5α2-6Galβ1-4GlcNAcβ1-3GalNAcα, Neu5Acα2-6Galβ1-4GlcNAcβ1-3Gal~1-3GalNAcα, Neu5Acα2-6GalNAc(β1-3Gal)β1-4Galβ1-4Glc, and Neu5Acα2-6GalNAc(β1-3Gal-)β1-3Galα1-4Galβ1-4Glc, α-Dystroglycan, asialoglycoprotein, sialyl Lewis, Neu5Ac(α2-3)Gal(β1-4)Glc, Neu5Acα2Me, dextran sulfate, heparin, or a combination thereof.

In another aspect, the present technology provides methods for treating or preventing viral infection including administering an effective amount of a liposome composition to a subject in need thereof, wherein the liposome composition comprises at least two binding targets, wherein the binding targets are linked to a first population of lipids to form BT-lipids, a second population of lipids, and cholesterols, wherein the BT-lipids, the second population of lipids, and cholesterols form a liposome, wherein the binding targets are displayed on the outer surface of the liposome, wherein the first and second population of lipids have a phase transition temperature below 41° C., and wherein the cholesterol is about 15 to 30 mol % of the liposome.

In some implementations, the first population of lipids and the second population of lipids are the same. In another implementation, the first population of lipids and the second population of lipids are different. In some implementations, the first and second population of lipids are selected from the group consisting of 12:0 phosphatidylcholine (PC), 13:0 PC, 14:0 PC, 15:0 PC, 16:0 PC, 16:1 PC, 18:1c9 PC, 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC, 16:0-22:6 PC, 18:0-14:0 PC, 18:0-18:1 PC, 18:1-16:0 PC, 18:1-18:0 PC, 12:0 phosphatidylglycerol (PG); 14:0 PG, 16:0 PG, 18:1 PG, 16:0-18:1 PG, 18:1 phosphatidylserine (PS), 16:0-18:1 PS, 12:0 phosphatidic acid (PA), 18:1 PA, 16:0-18:1 PA, 12:0 phosphatidylethanolamine (PE), 18:1c9 PE, 18:1t9 PE, 18:2 PE, 18:3 PE, 16:0-18:1 PE, or a combination thereof.

In some implementations, the binding targets are select from the group consisting of LSTc, α-5-N-acetyl-neuraminic acid (Neu5Ac), Neu5Acα2-3Galβ1-4GlcNAc, Neu5Acα2-6Galβ1-4GlcNAc, Neu5Acα2-3Galβ1-4GlcNAβ1-3Galβ14GlcNAc, Neu5Acα2-6Galβ1-4GlcNAcβ1-3Galβ1-4GlcNAc, Neu5Acα2-3Galβ1-4GlcNAcβ11-3Galβ1-4GlcNAcβ1-3Galβ1-4GlcNAc, Neu5Acα6Galβ4GlcNAcβ3Galβ4Glc, Neu5Acα3Galβ4GlcNAc, Neu5Acα6Galβ4GlcNAc, Neu5Acα3Gal, Neu5Acα6Gal, Neu5Acα3Galβ4Glc, Neu5Acα3Galβ3GlcNAc, Neu5Acα2-6Galβ1-4GlcNAcβ1-3Galβ1-4GlcNAc-, Neu5Acα2-6GalNAcβ1-4GlcNAcβ1-3GalNAcβ1-4GlcNAc-, Neu5Acα2-6GlcNAcβ1-3Galβ1-3/4GlcNAc-, Neu5Acα2-6Galβ1-4GlcNAcβ1-3Galβ1-3GalNAcα, Neu5Acα2-6Galβ1-4GlcNAcβ1-3Galβ1-4GlcNAcβ1-3Galβ1-3GalNAcα, Neu5Acα2-6GalNAcβ1-4GlcNAcβ1-3Galβ1-3GalNAcα, Neu5Acα2-6GalNAcβ1-4GlcNAcβ1-3GalNAcβ1-4GlcNAcβ1-3Galβ1-3GalNAcα, Neu5Acα2-6GalNAcα-β1-3Galα2-3Neu5Ac, Neu5Acα2-6Galβ1-4GlcNAcβ1-3/6GalNAcα, Neu5Acα2-6Galβ1-4GlcNAcβ1-3Galβ1-4GlcNAcβ1-3/6GalNAcα, Neu5Acα2-6GalNAcβ1-4GlcNAcβ1-3/6GalNAcα, Neu5Acα2-6GalNAcβ1-4GlcNAcβ1-3GalNAcβ1-4GlcNAcβ1-3/6GalNAcα, Neu5Acα2-6Galβ1-4GlcNAcβ1-6GalNAcα-β1-3Galα2-3Neu5Ac, Neu5Acα2-6Galβ1-4GlcNAcβ1-3/6GalNAcα-β1-3/6GlcNAcβ1-4Galα2-3/6Neu5Ac, Neu5Acα2-6GlcNAcβ1-3Galβ1-4GlcNAcβ1-3Galβ1-3GalNAc, Neu5Acα2-6GlcNAcβ1-3Galβ1-3GlcNAcβ1-3/6GalNAc, Neu5Acα2-6GlcNAcβ1-3Galβ1-4GlcNAcβ1-3/6GalNAc, Neu5Acα2-6Galβ1-3GalNAcβ1-4Galα1-3Galβ1-4Glc, Neu5Acα2-6Galβ1-4GlcNAcβ1-3Galβ1-4Glc, Neu5Acα2-6Galβ1-3GalNAcβ1-3Galα1-4Galβ1-4Glc, Neu5Acα2-6Galβ1-3GlcNAcβ1-3Galβ1-4Glc, Neu5α2-6Galβ1-4GlcNAcβ1-3GalNAcα, Neu5Acα2-6Galβ1-4GlcNAcβ1-3Gal-1-3GalNAcα, Neu5Acα2-6GalNAc(β1-3Gal)β1-4Galβ1-4Glc, and Neu5Acα2-6GalNAc(β1-3Gal-)β1-3Galα1-4Galβ1-4Glc, Dystroglycan, asialoglycoprotein, sialyl Lewis, Neu5Ac(α2-3)Gal(β1-4)Glc, Neu5Acα2Me, dextran sulfate, heparin, or a combination thereof.

In another aspect, the present technology provides compositions having a plurality of lipids and cholesterols, wherein the lipids and cholesterols form a liposome, wherein the lipids have a phase transition temperature below 41° C., and wherein the cholesterol is about 15 to 30 mol % of the liposome.

In some implementations, the lipids are selected from the group consisting of 12:0 phosphatidylcholine (PC), 13:0 PC, 14:0 PC, 15:0 PC, 16:0 PC, 16:1 PC, 18:1c9 PC, 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC, 16:0-22:6 PC, 18:0-14:0 PC, 18:0-18:1 PC, 18:1-16:0 PC, 18:1-18:0 PC, 12:0 phosphatidylglycerol (PG); 14:0 PG, 16:0 PG, 18:1 PG, 16:0-18:1 PG, 18:1 phosphatidylserine (PS), 16:0-18:1 PS, 12:0 phosphatidic acid (PA), 18:1 PA, 16:0-18:1 PA, 12:0 phosphatidylethanolamine (PE), 18:1c9 PE, 18:1t9 PE, 18:2 PE, 18:3 PE, 16:0-18:1 PE, or a combination thereof.

In some implementations, the liposome consists of 18:1 lipids and cholesterol, wherein the cholesterol is 15 to 30 mol % of the liposome. In some implementations, the 18:1 lipids are selected from the group consisting of DOPE, DOPC, DOPG, or a combination thereof.

In some implementations, at least two binding targets, wherein the binding targets are displayed on the outer surface of the lipid bilayer.

In another aspect, the present technology provides a kit including at least one liposome composition, wherein the liposome composition comprises at least two binding targets, wherein the binding targets are linked to a first population of lipids to form BT-lipids, a second population of lipids, and a plurality of cholesterols, wherein the BT-lipids, the second population of lipids, and cholesterols form a liposome, wherein the binding targets are displayed on the outer surface of the liposome, wherein the first and second population of lipids have a phase transition temperature below 41° C., and wherein the cholesterol is about 15 to 30 mol % of the liposome.

In some implementations, the first population of lipids and the second population of lipids are the same. In some implementations, the first population of lipids and the second population of lipids are different. In some implementations, the first and second population of lipids are selected from the group consisting of 12:0 phosphatidylcholine (PC), 13:0 PC, 14:0 PC, 15:0 PC, 16:0 PC, 16:1 PC, 18:1c9 PC, 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC, 16:0-22:6 PC, 18:0-14:0 PC, 18:0-18:1 PC, 18:1-16:0 PC, 18:1-18:0 PC, 12:0 phosphatidylglycerol (PG); 14:0 PG, 16:0 PG, 18:1 PG, 16:0-18:1 PG, 18:1 phosphatidylserine (PS), 16:0-18:1 PS, 12:0 phosphatidic acid (PA), 18:1 PA, 16:0-18:1 PA, 12:0 phosphatidylethanolamine (PE), 18:1c9 PE, 18:1t9 PE, 18:2 PE, 18:3 PE, 16:0-18:1 PE, or a combination thereof.

In some implementations, the liposome consists of 18:1 lipids and cholesterol, wherein the cholesterol is about 15 to 30 mol % of the liposome. In some implementations, the 18:1 lipids are selected from the group consisting of DOPE, DOPC, DOPG, or a combination thereof.

In some implementations, the binding targets are selected from the group consisting of LSTc, Neu5Acα2-3Galβ1-4GlcNAc, Neu5Acα2-6Galβ1-4GlcNAc, Neu5Acα2-3Galβ1-4GlcNAβ1-3Galβ14GlcNAc, Neu5Acα2-6Galβ1-4GlcNAcβ1-3Galβ1-4GlcNAc, Neu5Acα2-3Galβ1-4GlcNAcβ11-3Galβ1-4GlcNAcβ1-3Galβ1-4GlcNAc, Neu5Ac, Neu5Acα6Galβ4GlcNAcβ3Galβ4Glc, Neu5Acα3Galβ4GlcNAc, Neu5Acα6Galβ4GlcNAc, Neu5Acα3Gal, Neu5Acα6Gal, Neu5Acα3Galβ4Glc, Neu5Acα3Galβ3GlcNAc, α-Dystroglycan, asialoglycoprotein, sialyl Lewis, Neu5Ac(α2-3)Gal(β1-4)Glc, Neu5Acα2Me, heparin, or a combination thereof.

In some implementations, the kit also includes a tool for delivering the liposome composition.

BRIEF DESCRIPTION OF DRAWINGS

FIGS. 6A and 6C show LSTc liposomes that contain NBD (green) bound specifically to WSN HA-647 (red) and can be seen binding to the apical portion of virus foci when the field of view is rotated 37 degrees. FIGS. 6B and 6D show control liposomes that do not display significant co-localization with WSN HA-647. Scale-bar equals 1 μm.

DETAILED DESCRIPTION

Figure 1:
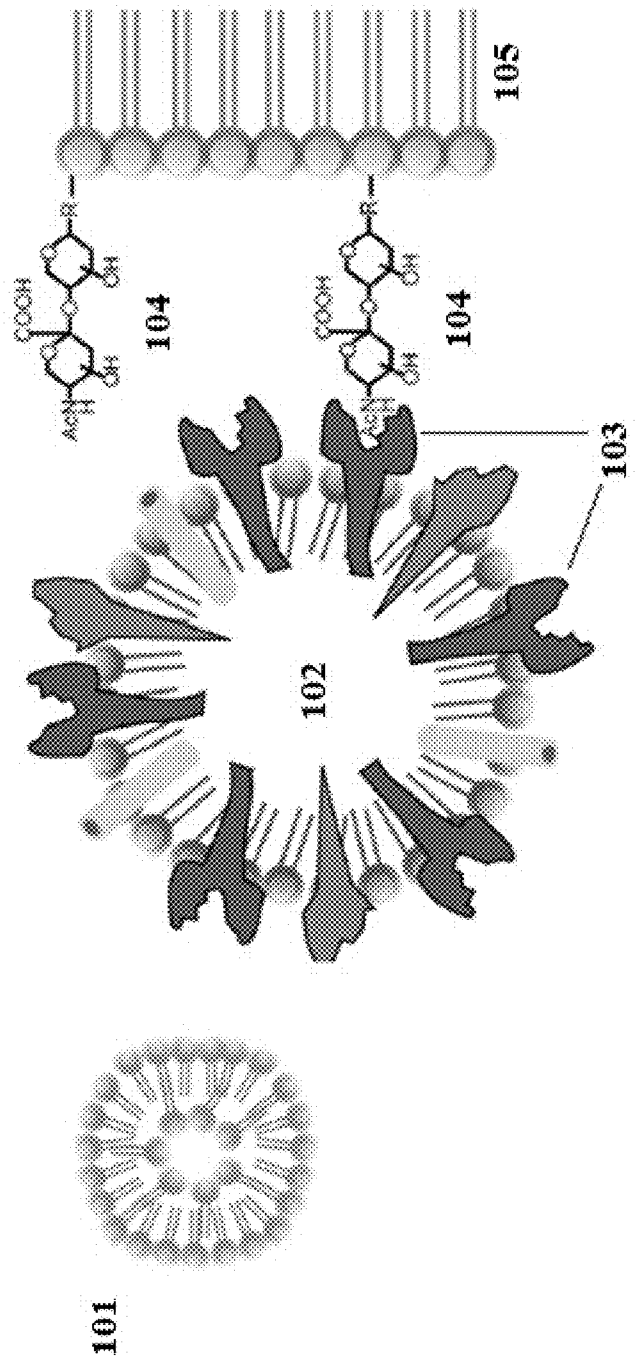
FIG. 1A-C is an exemplary, non-limiting diagram showing how sialylneolacto-N-tetraose c (LSTc) liposomes are more effective in inhibiting influenza A virus binding to the cell membrane as compared to monovalent LSTc liposomes and liposome without binding targets.
Figure 1:
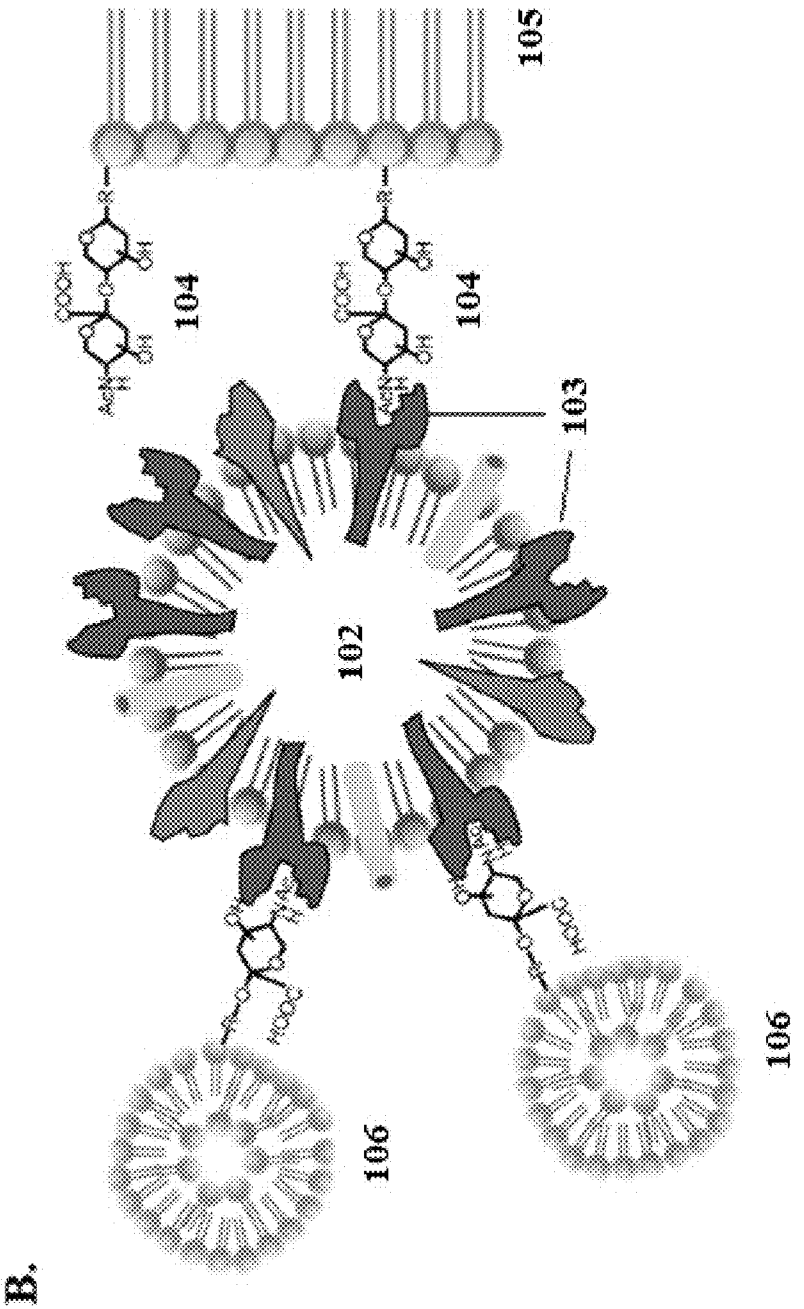
Figure 1:
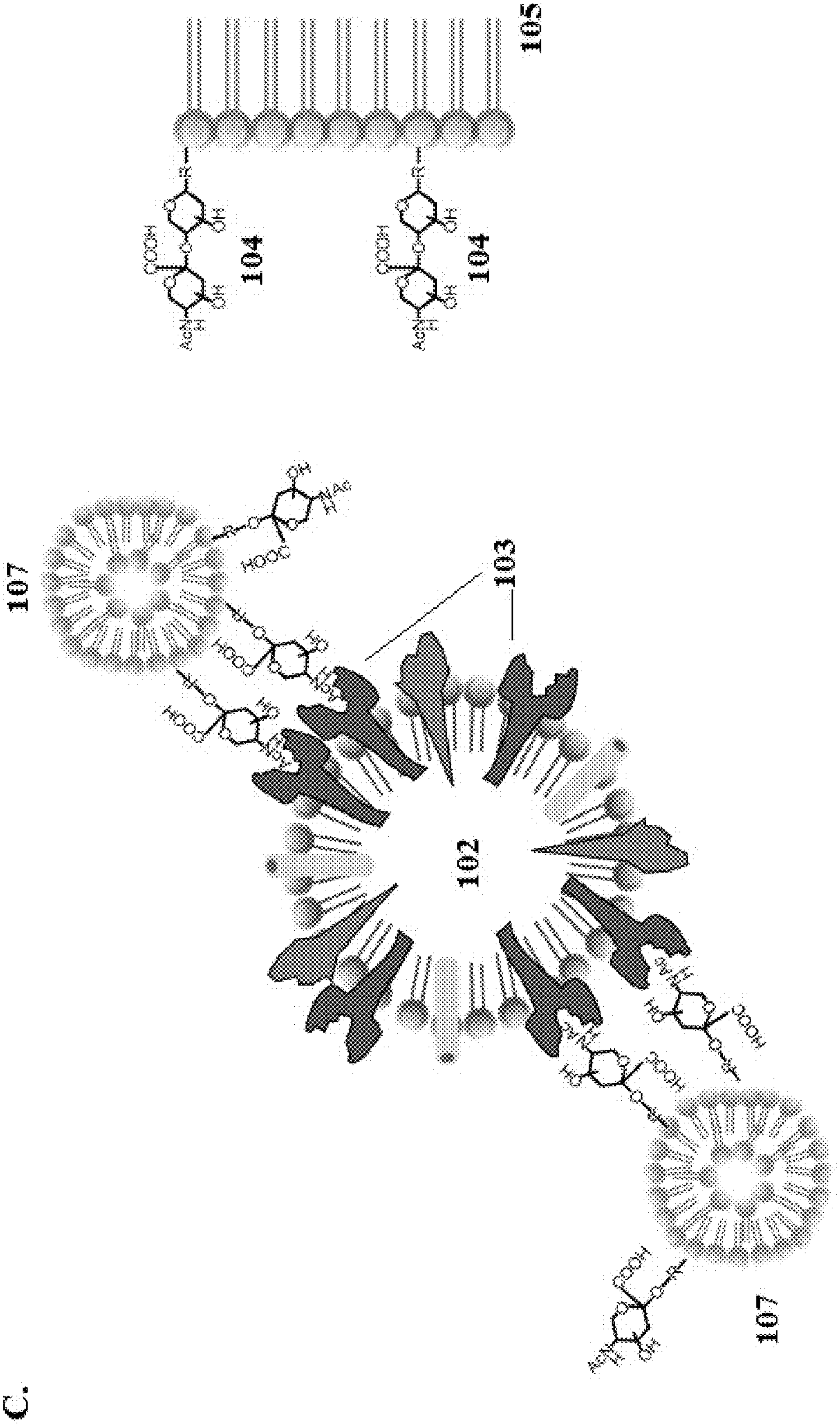

The various concepts introduced above and discussed in greater detail below can be implemented in any of numerous ways, as the described concepts are not limited to any particular manner of implementation. Examples of specific implementations and applications are provided primarily for illustrative purposes. The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent, drug, or multivalent composition to a subject includes any route of introducing or delivering to a subject a compound to perform its intended function. Administration can be carried out by any suitable route, including inhalation, orally, intranasally, or parenterally (intravenously, intramuscularly, intraperitoneally, or subcutaneously). Administration includes self-administration and the administration by another.

As used herein, "binding target" or "binding targets" refers to a molecule or compound that resembles, mimics, or is the binding molecule or compound on the cell surface of a host cell that a virus, bacteria, or toxin binds to gain entry into the cell. For example, influenza A, through influenza hemaggglutinin (HA), binds to sialic acid (SA) on a host cell's outer membrane. In this example, SA is the binding target. As used herein "cellular binding target" refers to those binding targets that are on the cell, e.g., naturally presented on the cell surface. By way of example, but not by limitation, a binding target that is not on the cell would also bind to viral HA, and would prevent the influenza virus from binding to the cellular SA on the host cell's outer membrane. Examples of binding targets include, but are not limited to, sialylneolacto-N-tetraose c (LSTc), Neu5Acα2-3Galβ1-4GlcNAc, Neu5Acα2-6Galβ1-4GlcNAc, Neu5Acα2-3Galβ1-4GlcNAβ1-3Galβ14GlcNAc, Neu5Acα2-6Galβ1-4GlcNAcβ1-3Galβ1-4GlcNAc, Neu5Acα2-3Galβ1-4GlcNAcβ11-3Galβ1-4GlcNAcβ1-3Galβ1-4GlcNAc, Neu5Ac, Neu5Acα6Galβ4GlcNAcβ3Galβ4Glc, Neu5Acα3Galβ4GlcNAc, Neu5Acα6Galβ4GlcNAc, Neu5Acα3Gal, Neu5Acα6Gal, Neu5Acα3Galβ4Glc, and Neu5Acα3Galβ3GlcNAc.

As used herein, the term "effective amount" refers to a quantity sufficient to achieve a desired therapeutic and/or prophylactic effect, e.g., an amount, which results in the decrease of viral or bacterial infection in a subject. In the context of therapeutic or prophylactic applications, in some implementations, the amount of a composition administered to the subject will depend on the levels of virus or bacteria in the subject, and on the characteristics of the individual, such as general health, age, sex, body weight and tolerance to drugs. In some implementations, it will also depend on the degree, severity, and type of disease. The skilled artisan will be able to determine appropriate dosages depending on these and other factors. The compositions can also be administered in combination with one or more additional therapeutic compounds. In the methods described herein, the multivalent composition of the present technology can be administered to a subject having one or more signs or symptoms of viral or bacterial infection such as, e.g., sneezing, muscle aches, fever, congestion (sinus or bronchial), coughing, headaches, bronchiolitis, vomiting, fatigue, cramping, chills, and diminished appetite. For example, a "therapeutically effective amount" of a multivalent composition includes amounts in which the level of virus or bacteria is reduced in a subject after administration compared to control subjects who do not receive the compositions. In some implementations, a therapeutically effective amount also reduces or ameliorates the physiological effects, signs or symptoms (e.g., fever, cough, sinus congestion, muscle aches, etc.) of viral or bacterial infection.

As use herein, "isolated" or "purified" refers to a compound that is substantially free of cellular material or other contaminates from the source from which the compound is derived, or substantially free from chemical precursors or other chemicals when chemically synthesized. For example, isolated LSTc would be free of materials that would interfere with diagnostic or therapeutic uses of the agent. Such interfering materials may include enzymes, hormones and other proteinaceous and nonproteinaceous materials.

As used herein, "glycolipid" has its customary and ordinary meaning and refers to a carbohydrate linked to a lipid. In some implementations, the binding target is a carbohydrate (e.g., LSTc), and a glycolipid is formed by linking the carbohydrate-containing binding target to a lipid. As used herein, "lipid" has its customary meaning in the art and refers, for example, to any synthetic, semi-synthetic, or naturally occurring lipids, including phospholipids. By way of example, but not by limitation, in some implementations, a glycolipid includes LSTc linked to a phospholipid, e.g., DOPE.

As used herein, "mobile," "mobility," or "fluidity" refers to the lateral movement within a lipid bilayer. Lateral movement is associated with the phase behavior of the lipid bilayer. For example, longer tailed lipids have more area over which to interact; thus increasing the strength of the Van der Waals interaction between them and consequently decreasing the mobility, i.e., lateral movement, within a lipid bilayer. Unsaturated lipids, which have kinks in the lipid tails, are likely to increase mobility within the lipid bilayer because the kinks in the lipid tail prevent a tightly pack lipid bilayer.

As used herein, "prevention" or "preventing" of an infection or exposure to a toxin refers to a compound that, in a statistical sample, reduces the occurrence of viral or bacterial infection or reduces the effects of a toxin in the treated sample relative to an untreated control sample, or delays the onset or reduces the severity of one or more symptoms of the viral or bacterial infection or exposure to toxin relative to the untreated control sample. As used herein, preventing viral or bacterial infection includes, but is not limited to, preventing the initiation of viral entry into a cell, preventing a virus or bacteria from binding to a cell or tissue, delaying the infection of a cell by a virus, preventing the progression or advancement of viral or bacterial infection, prevention of bacterial colonization, prevention of bacterial toxins binding to a cell, and reversing the progression of viral and bacterial infection from an advanced to a less advanced stage. As used herein, preventing physiological effects of a toxin or toxins includes, but is not limited to, preventing the initiation of toxin entry into a cell, preventing a toxin or toxins from binding to a cell or tissue, delaying the entry of a toxin or toxins into a cell, preventing the progression or advancement of toxic effect by the toxin or toxins, and reversing the progression of exposure to a toxin or toxins from an advanced to a less advanced stage.

As used herein, the term "separate" therapeutic administration refers to an administration of at least two active ingredients at the same time or at substantially the same time by different routes.

As used herein, the term "sequential" therapeutic administration refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients.

As used herein, the term "simultaneous" therapeutic administration refers to the administration of at least two active ingredients by the same route and at the same time or at substantially the same time.

As used herein, the terms "treating" or "treatment" or "alleviation" refers to therapeutic course of action (e.g., administering a therapeutic composition), wherein the object is to prevent, alleviate, ameliorate or slow down (lessen) the targeted pathologic condition or disorder. For example, a subject is successfully "treated" for viral or bacterial infection if, after receiving a therapeutic amount of a multivalent liposome composition of the present disclosure according to the methods described herein, the subject shows observable and/or measurable reduction in or absence of one or more signs and symptoms of viral or bacterial infection, such as, e.g., sneezing, muscle aches, fever, congestion (sinus or bronchial), coughing, headaches, bronchiolitis, vomiting, fatigue, cramping, chills, and diminished appetite. It is also to be appreciated that the various modes of treatment or prevention of medical conditions as described are intended to mean "substantial," which includes total but also less than total treatment or prevention, and wherein some biologically or medically relevant result is achieved.

I. Multivalent Liposome Composition

General

The present technology generally relates to the treatment or prevention of infection, e.g., viral infection or bacterial infection, by administration of at least one multivalent liposome composition that includes two or more binding targets linked to a liposome with a fluid lipid bilayer, to a subject in need thereof. The compositions typically bind the virus (or virions), e.g., influenza, or bacteria, e.g., *Streptococcus pneumonia*, with high affinity to reduce or prevent infectivity. The compositions can be administered to animals, e.g., humans or avian species infected with viruses or bacteria to treat infection, or administered to those exposed to virus or bacteria or likely to be exposed to virus or bacteria, or those at risk of infection, thereby to prevent infection.

In some implementations, the present technology is used to reduce or prevent the effects of a toxin. The composition will bind to the toxin, e.g., ricin, with high affinity to reduce or prevent toxin entry into a cell. The compositions can be administered to animals, e.g., or avian species, exposed to toxins, or given to those likely to be exposed to toxins, or those at risk of exposure to toxins, thereby to prevent, delay onset or alleviate toxic effects.

Binding targets are compounds that resemble or mimic molecules or compounds, and in some implementations are the molecules or compounds, to which virus (or virions), bacteria, or toxin bind to facilitate entry into a cell. In general, the molecules or compounds to which a virus (or virions), bacteria, or toxins bind are located on a cell or tissue surface (cellular binding targets). Additionally, in general, the virus (or virions), bacteria, or toxin bind to the cellular binding target on the cell surface or tissue to infect the cell or tissue (or in the case of toxins enter the cell or tissue). In some cases, bacteria form colonies on tissue. In some implementations of the present technology, binding targets bind to the virus (or virions), bacteria, or toxins to prevent binding of the virus (or virions), bacteria, or toxins to the cellular binding target on a cell or tissue surface. Additionally, or alternatively, in some implementation, the binding targets bind to bacteria to prevent bacteria from forming colonies.

The multivalent liposome composition of the present technology has enhanced binding due to the multivalent display of binding targets and the mobility of the binding targets on the surface of the liposome. Multivalency is the display of at least two binding targets on the surface of the liposome. By way of example, but not by way of limitation, FIGS. 1A-C illustrate the enhanced inhibitory effect of multivalent liposome compositions. Referring to FIG. 1A, influenza virus 102 infects host cells by first attaching to α2-6 terminally linked SA 104 on the cell membrane 105 through HA 103. Liposomes 101 that do not contain LSTc, in general, have low effect in inhibiting influenza virus adhesion or infection.

With reference to FIG. 1B, monovalent LSTc liposomes 106 bind to the HA receptors 103 of the influenza virus 102.

With reference to FIG. 1C, a single multivalent LSTc liposome composition 107, e.g., with 5 mol % or more LSTc on the surface, are capable of competitively binding multiple HA receptors 203 of the influenza virus 102. The presence of multiple binding targets on the surface of a single liposome allows a single liposome to have enhanced, efficient, and high affinity binding to the virus, bacteria, or toxin as compared to the monovalent LSTc liposome of FIG. 1B.

Mobility of the binding targets on the surface on the liposome relates to the lateral movement of the binding targets on the surface of the liposome. The mobility of the binding targets enhances binding to multiple targets as compared to fixed binding targets or less mobile binding target because a mobile binding target can change its position relative to an adjacent bound binding target to bind a second receptor on the virus, bacteria, or toxin or bind a receptor on second virus, bacteria, or toxin. The mobility relates to the fluidity of the liposome's surface membrane.

The fluidity, i.e., the phase behavior, of lipid bilayers is largely determined by the strength of the attractive Van der Waals interactions between adjacent lipid molecules. The strength of the interaction can be governed by how long the lipid tails are and how well they can pack together. For example, longer tailed lipids have more area over which to interact, thus increasing the strength of the Van der Waals interaction and consequently decreasing the lipid mobility. At a given temperature, a short-tailed lipid is more fluid than an otherwise identical long-tailed lipid. For example, saturated phosphatidylcholine lipids with tails longer than 14 carbons are solid at room temperature, while those with fewer than 14 are liquid.

Aside from chain length, phase behavior can also be affected by the degree of unsaturation of the lipid tails. An unsaturated double bond can produce a kink in the alkane chain, disrupting the regular periodic structure. The disruption creates extra free space within the lipid bilayer, which allows additional flexibility in the adjacent chains. The disruption of packing leads to lower transition temperatures with increasing double bonds, which is a significant effect. For example, decreasing the overall chain length by one carbon usually alters the transition temperature of a lipid by ten degrees Celsius or less, but adding a single double bond can decrease the transition temperature by fifty degrees or more.

The phase behavior of lipid bilayers is also dependent on temperature. In general, all lipids have a temperature where the lipid transitions, i.e., "melts," from a solid to a liquid.

In some implementations, cholesterol and/or short-chain alcohols are included in the liposome. In general, cholesterol usually decreases the fluidity of lipid bilayers by increasing membrane packing. However, cholesterol at certain concentrations in the lipid bilayers can lead to the formation of lipid rafts.

Figure 3:
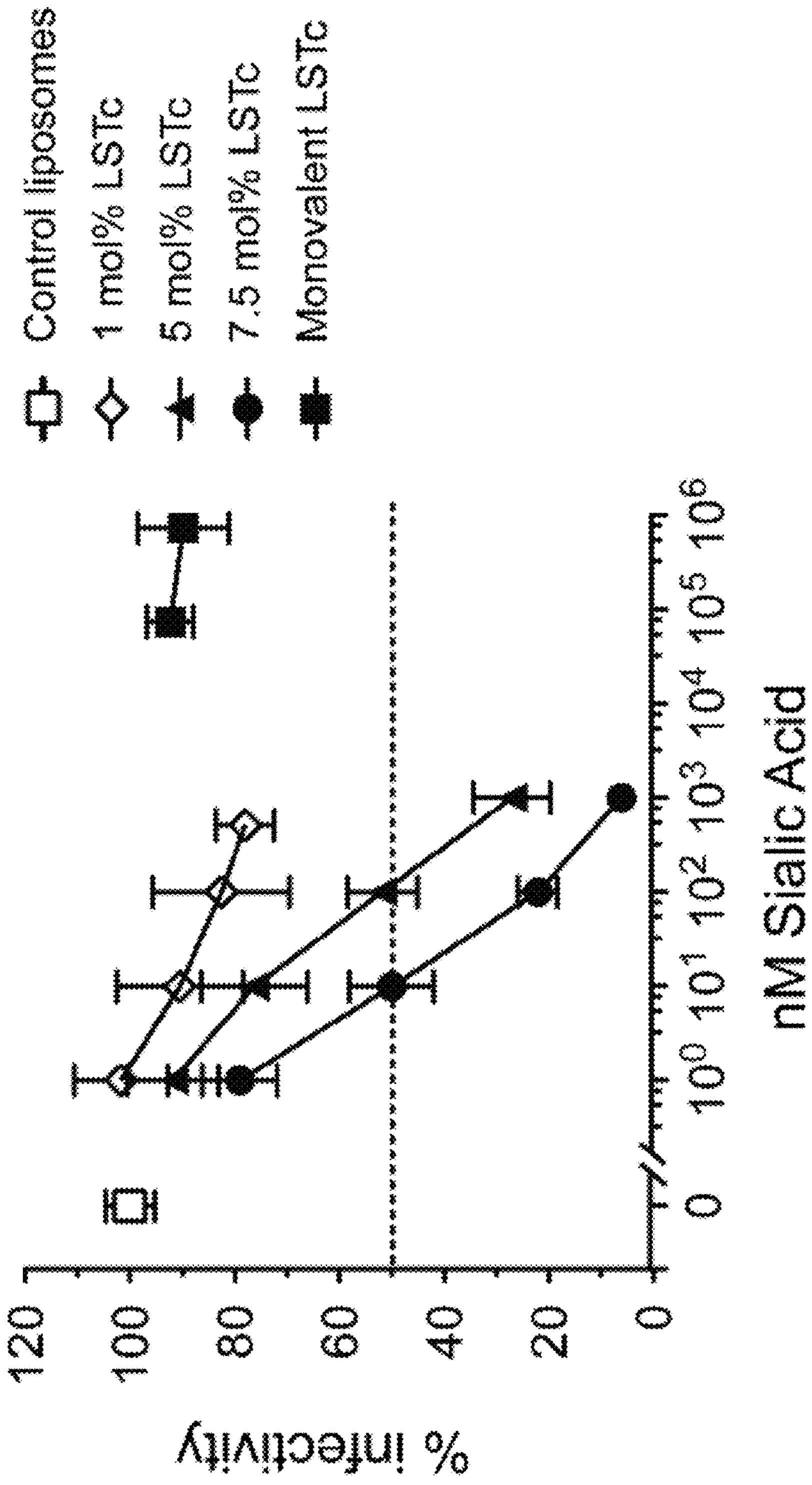
FIG. 3A is a graph showing that LSTc liposomes inhibit influenza infection of MDCK cells. PR/8 (50 PFU/well) was incubated with control or LSTc liposomes before addition to MDCK cells. Plaques per well of virus treated with control liposomes (0 mol % LSTc) are defined as 100% infectivity (open square) and virus treated with different liposome formulations are expressed as the percent reduction from its respective control. LSTc liposomes with 7.5 mol % LSTc inhibited PR/8 (circles) to the greatest extent. LSTc liposomes with 5 mol % LSTc (triangles) also significantly inhibited infection. However LSTc liposomes with 1 mol % LSTc (open diamonds) did not significantly inhibited infection. Monovalent LSTc liposomes (closed square) also did not significantly inhibited infection at high concentrations.
FIG. 3B is a graph showing that LSTc liposomes specifically inhibit influenza infection. LSTc liposomes containing 7.5 mol % LSTc inhibit multiple strains of influenza. LSTc liposomes inhibited Philippines (open triangles, 50 PFU/well), X-31 (crosses, 50 PFU/well), and Beijing (open circles, 15 PFU/well) strains of influenza. LSTc liposomes did not inhibit RSV (filled squares, 50 PFU/well). The data represent the average±SEM of three experiments for PR/8 and two experiments for Philippines, X-31, Beijing, and RSV.
Figure 3:
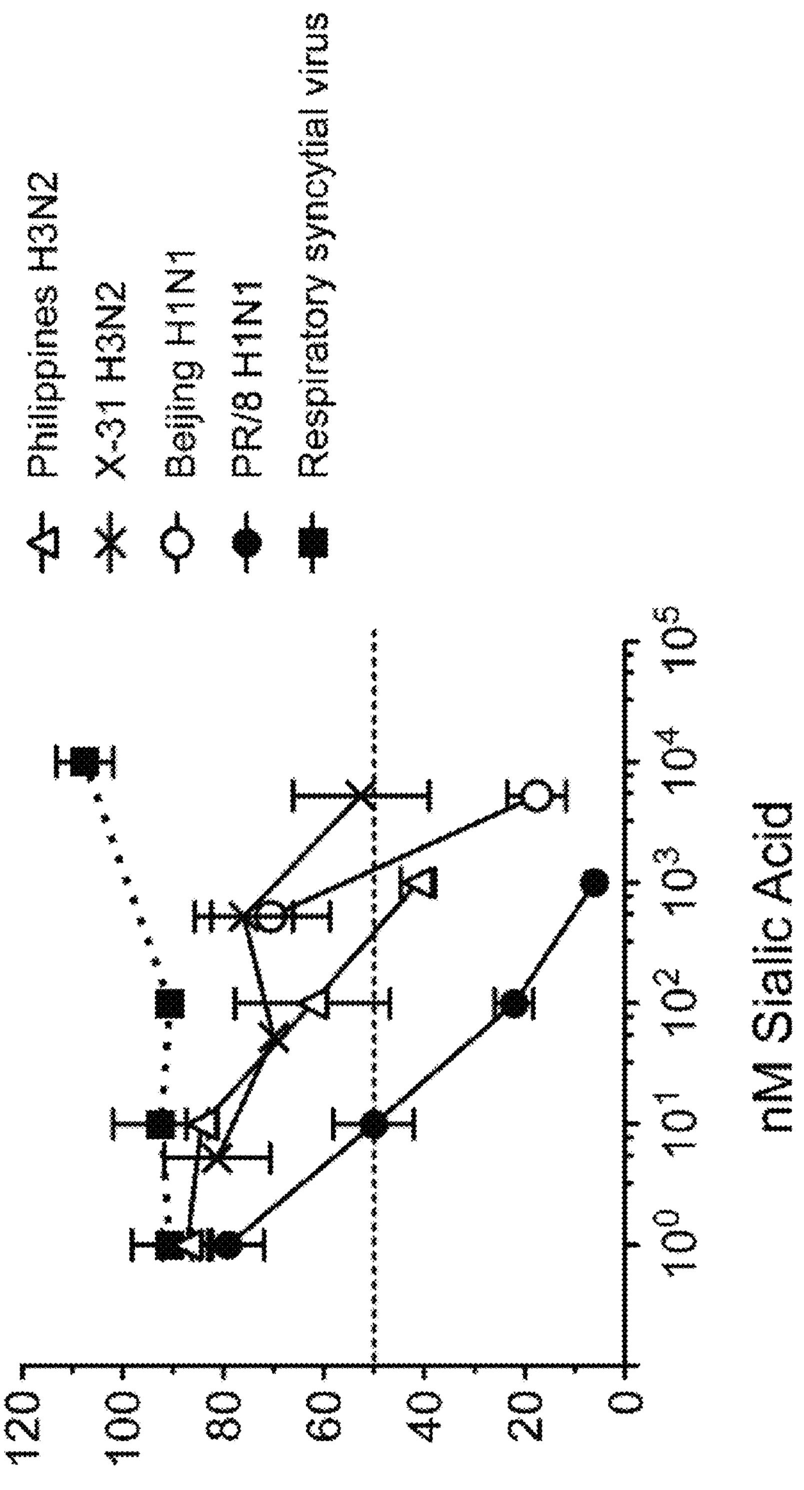
Figure 8:
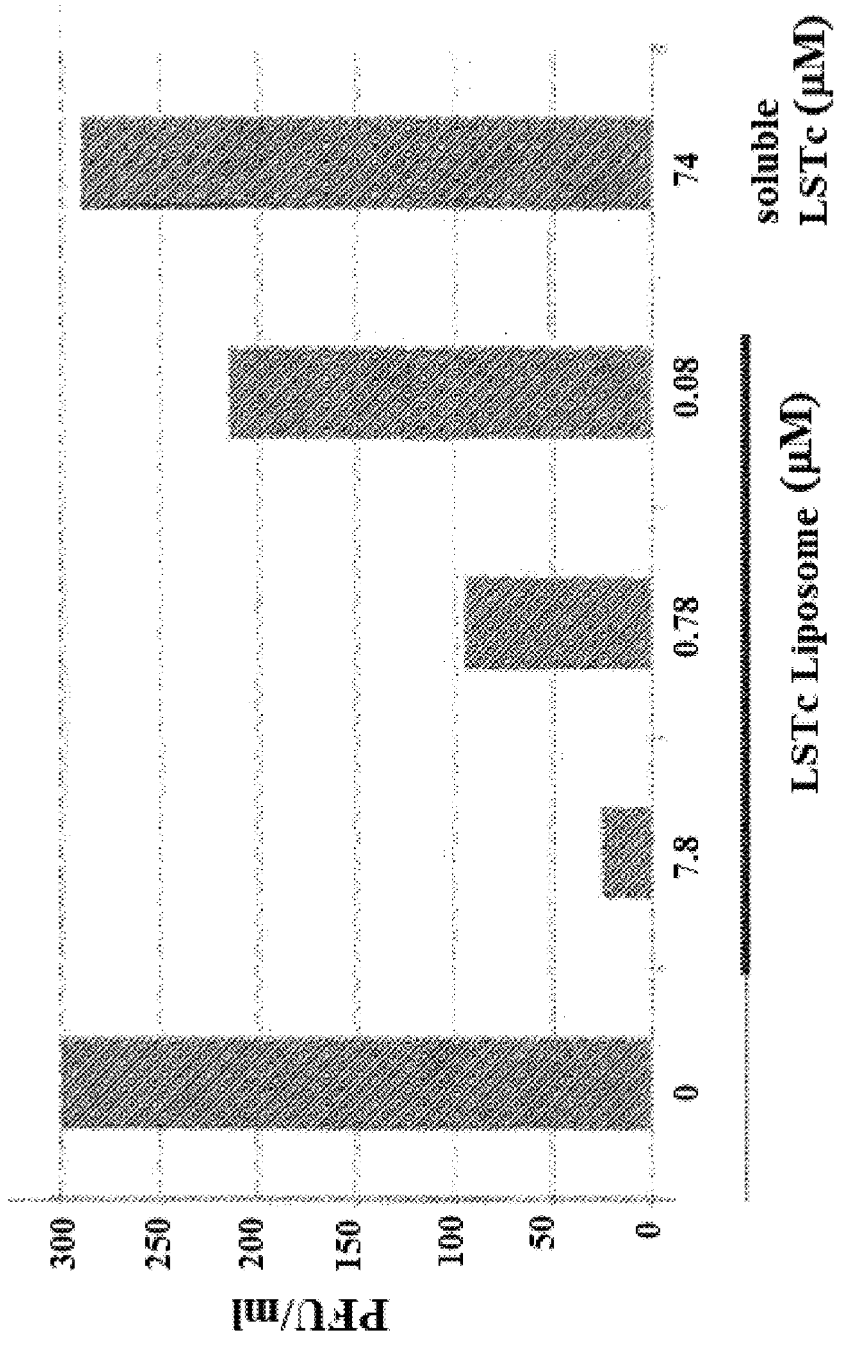
FIG. 8 is a chart comparing the anti-viral effect of LSTc liposomes and free LSTc on influenza infection of cells grown in tissue culture. LSTc liposomes are at least 1000-fold more effective in inhibiting influenza infection (indicated by viral yield in PFU/ml) than soluble LSTc.

The multivalent display and increased mobility of the liposome compositions of the present technology allows for more efficient and effective binding by the composition as compared to monovalent display or treatment with a plurality of binding targets not bound to a liposome by the methods disclosed herein, see, e.g., FIG. 3A and FIG. 8.

Binding Targets

A. Virus or Virions

In general, viruses infect host cells by receptor-mediated binding. For example, influenza hemagglutinin (HA) is a glycoprotein found on the surface of the influenza viruses. HA binds to specific carbohydrate structures on the cell surface of a host cell. Generally, human-adapted influenza virus binds to terminal sialic acid (SA), see, e.g., FIG. 1A, on the cell surface in α2-6 linkage.

Binding targets that resemble, mimic, or are the molecules or compounds on the cell surface to which viruses bind can be used to reduce, treat, or prevent viral infection. In some implementations, binding targets are useful for reducing, treating, or preventing infection by a virus or virions. In some implementations, binding targets are one or more glycans.

In some implementations, the binding target is specific for preventing infection by influenza A (IAV). Additionally, or alternatively, in some implementations, the IAV binding target contains an α2-6 linked SA. In other implementations, the IAV binding target contains an α2-3 linked SA. In some implementations, the α2-3 linked SA binding target is used to reduce or prevent IAV infection in avian species. Examples of binding targets that reduce or prevent IAV infection include, but are not limited to, sialylneolacto-N-tetraose c (LSTc), α-5-N-acetyl-neuraminic acid (Neu5Ac), Neu5Acα2-3Galβ1-4GlcNAc, Neu5Acα2-6Galβ1-4GlcNAc, Neu5Acα2-3Galβ1-4GlcNAβ1-3Galβ14GlcNAc, Neu5Acα2-6Galβ1-4GlcNAcβ1-3Galβ1-4GlcNAc, Neu5Acα2-3Galβ1-4GlcNAcβ11-3Galβ1-4GlcNAcβ1-3Galβ1-4GlcNAc, Neu5Acα6Galβ4GlcNAcβ3Galβ4Glc, Neu5Acα3Galβ4GlcNAc, Neu5Acα6Galβ4GlcNAc, Neu5Acα3Gal, Neu5Acα6Gal, Neu5Acα3Galβ4Glc, Neu5Acα3Galβ3GlcNAc, Neu5Acα2-6Galβ1-4GlcNAcβ1-3Galβ1-4GlcNAc-, Neu5Acα2-6GalNAcβ1-4GlcNAcβ1-3GalNAcβ1-4GlcNAc-, Neu5Acα2-6GlcNAcβ1-3Galβ1-3/4GlcNAc-, Neu5Acα2-6Galβ1-4GlcNAcβ1-3Galβ1-3GalNAcα, Neu5Acα2-6Galβ1-4GlcNAcβ1-3Galβ1-4GlcNAcβ1-3Galβ1-3GalNAcα, Neu5Acα2-6GalNAcβ1-4GlcNAcβ1-3Galβ1-3GalNAcα, Neu5Acα2-6GalNAcβ1-4GlcNAcβ1-3GalNAcβ1-4GlcNAcβ1-3Galβ1-3GalNAcα, Neu5Acα2-6GalNAcα-β1-3Galα2-3Neu5Ac, Neu5Acα2-6Galβ1-4GlcNAcβ1-3/6GalNAcα, Neu5Acα2-6Galβ1-4GlcNAcβ1-3Galβ1-4GlcNAcβ1-3/6GalNAcα, Neu5Acα2-6GalNAcβ1-4GlcNAcβ1-3/6GalNAcα, Neu5Acα2-6GalNAcβ1-4GlcNAcβ1-3GalNAcβ1-4GlcNAcβ1-3/6GalNAcα, Neu5Acα2-6Galβ1-4GlcNAcβ1-6GalNAcα-β1-3Galα2-3Neu5Ac, Neu5Acα2-6Galβ1-4GlcNAcβ1-3/6GalNAcα-β1-3/6GlcNAcβ1-4Galα2-3/6Neu5Ac, Neu5Acα2-6GlcNAcβ1-3Galβ1-4GlcNAcβ1-3Galβ1-3GalNAc, Neu5Acα2-6GlcNAcβ1-3Galβ1-3GlcNAcβ1-3/6GalNAc, Neu5Acα2-6GlcNAcβ1-3Galβ1-4GlcNAcβ1-3/6GalNAc, Neu5Acα2-6Galβ1-3GalNAcβ1-4Galα1-3Galβ1-4Glc, Neu5Acα2-6Galβ1-4GlcNAcβ1-3Galβ1-4Glc, Neu5Acα2-6Galβ1-3GalNAcβ1-3Galα1-4Galβ1-4Glc, Neu5Acα2-6Galβ1-3GlcNAcβ1-3Galβ1-4Glc, Neu5α2-6Galβ1-4GlcNAcβ1-3GalNAcα, Neu5Acα2-6Galβ1-4GlcNAcβ1~3Gal-1-3GalNAcα, Neu5Acα2-6GalNAc(β1-3Gal)β1-4Galβ1-4Glc, and Neu5Acα2-6GalNAc(β1-3Gal-)β1-3Galα1-4Galβ1-4Glc. In some implementations, the binding target is LSTc.

In some implementations, the IAV binding target is a umbrella-topology glycan. In some implementations, the umbrella-topology glycan has the structure of Neu5Acα2-6Sug1-Sug2-Sug3-Sug4, wherein one or more of the following conditions are met: 1) Neu5Ac α2-6 is at the non-reducing end of the glycan; 2) Sug1, Sug2, Sug3, or Sug4 is a hexose or hexosamine in a or β configuration; 3) no sugars other than Neu5Acα2-6 are attached to any of the non-reducing positions of Sug1; 4) non-sugar moieties are attached to non-reducing positions of Sug1, Sug2, Sug3, or Sug4; 5) Linkage between any two sugars in the oligosaccharide apart from Neu5Acα2-6 linkage are 1-2, 1-3, 1-4, and/or 1-6; and 6) the Neu5Acα2-6Sug1-Sug2-Sug3-portion satisfies structural constraints or hemagglutinin contact constraints of the umbrella-like topology glycan.

In some implementations, the binding target is specific for a non-IAV virus. Examples of non-IAV viruses include, but are not limited to, Cercopithecine herpes virus 1, Arenavirus (e.g., Lassa virus), Picornavirus (e.g., foot-and-mouth and Enterovirus 71), Orthomyxovirus (e.g., influenza B), influenza C, Paramyxovirus (e.g., parainfluenza), Reovirus (e.g., rotavirus and norovirus), Alphavirus (e.g., Eastern equine encephalitis), Filovirus (e.g., Marburg virus), Polyomavirus (e.g., human polyomaviruses), Herpes B, epidemic keratoconjunctivitis virus, adenovirus, and respiratory syncytial virus (RSV). Examples of binding targets that reduce or prevent non-IAV viral infection include, but are not limited to, any one of the above listed binding targets, α-Dystroglycan (e.g., for use against Lassa virus), asialoglycoprotein (for use against Marburg virus), sialyl Lewis (for use against norovirus), Neu5Ac(α2-3)Gal(β1-4)Glc (for use against rotavirus), Neu5Acα2Me (e.g., for use against rotavirus), dextran sulphate, heparin, chondrotin sulphate B (e.g., for use against RSV), NeuAcα2-3Galβ1-4GlcNAc (for use against human parainfluenza virus type 1), NeuGcα2-3Galβ1-4GlcNAc, NeuAcα2-6Galβ1-4GlcNAc, NeuAcα2-3Galβ1-4GlcNAc (for use against human parainfluenza virus type 1), NeuAc (α2-3)Gal (e.g., for use against influenza B), and N-acetyl-9-O-NeuAc(α2-3)Gal (e.g., for use against influenza C).

B. Bacteria

In general, bacteria infect cells or tissue by receptor-mediated binding. For example, *Streptococcus pneumonia* bind to N-acetylhexosamine-galactose disaccharide on the surface of mucosal epithelium.

Binding targets that resemble, mimic, or are the molecules or compounds on the cell or tissue surface to which bacteria bind can be used to reduce, treat, or prevent bacterial infection. In some implementations, binding targets are useful for reducing, treating, or preventing infection by a bacteria.

In some implementations, the binding target is specific for treating or preventing infection by bacteria. Examples of binding targets that reduce or prevent bacterial infection include, but are not limited to, amphotericin B, dextran sulphate, Fucα2GalβGlcNAc, Manα3Manα6Man, Galα4Gal, NeuAc (α2-3)Galβ3GalNAc, NeuAc (α2-8), GalNAcβ4Galβ, GlcNAc, GlcNAcβ4GlcNAc, NeuAc(α2-3) Galβ4Glc, NeuAc(α2-3)Galβ4GlcNAc, Fucα2Galβ3 (Fucα4)Gal, Man, Galβ4Glc(NAc), $[NeuAc(\alpha 2\text{-}3)]_{0,1}$, Galβ4GlcNAcβ3Galβ4GlcNAc, L-Fuc, Galβ3Glc(NAc) β3Galβ4Glc, and Galα4Galβ4Glc.

C. Toxins

In general, a toxin or toxins penetrate cells or tissue by receptor-mediated binding. For example, ricin binds to glycolipids and glycoproteins with terminal galactose on the cell surface.

Binding targets that resemble, mimic, or are the molecules or compounds on the cell or tissue surface to which a toxin binds can be used to reduce or prevent toxin entry into a cell or tissue. In some implementations, binding targets are useful for reducing, treating, or preventing toxin entry into a cell or tissue.

In some implementations, the binding target is specific for reducing or preventing a toxin from entering a cell or tissue. Examples of binding targets that reduce or prevent a toxin from entering a cell or tissue include, but are not limited to, GT1b, GQ1b, GD1a, phosphatidylethanolamine, unsaturated fatty acids, synaptotagmins I and II, digalactosylceramide, $Lewis^a$, Asialo-GM1, lactosylceramide, and N-acetyllactosamine glycans In some implementations, the binding target is specific for a single toxin. In some implementations, the binding target binds to one or more types of toxins. In some implementations, the toxin is a bacterial toxin.

BT-Lipids

In some implementations, the binding target ("BT") is linked to a lipid, e.g., a first population of lipid, to form a BT-lipid. In some implementations, at least two BT-lipids (e.g., 2, 3, 4, or plurality) are combined with a mixture of additional lipids, e.g., a second population of lipids, to form at least one multivalent liposome composition. In some implementations, the first population of lipids and the second population of lipids are the same. In some implementations, the first population of lipids and the second population of lipids are different. In some implementations, the multivalent liposome composition improves the binding efficiency of the binding targets to at least one virus, bacteria, or toxin by facilitating multivalent interactions with the virus, bacteria, or toxin.

In some implementations, multivalent display is achieved by having at least two binding targets (e.g., a plurality) displayed on the surface of a liposome. In some implementations, the binding targets are all the same. By way of example, but not by limitation, two or more LSTc are linked to DOPE, to form BT-lipids that are incorporated into a liposome such that that the LSTc moieties are displayed on the surface of a liposome (e.g., having a first population of lipids linked to the binding target and a second population of lipids not bound to the liposome. In another implementation, a plurality of different binding targets, i.e., two or more different types of binding targets are used. By way of example, but not by limitation, at least one LSTc and at least one Neu5Acα2-3Galβ1-4GlcNAc are linked to DOPE, and incorporated into a liposome such that the LSTc and the Neu5Acα2-3Galβ1-4GlcNAc are displayed on the surface of the liposome.

In some implementations, the lipids linked to the binding target, e.g., a first population of lipids, include, but are not limited to, synthetic, semi-synthetic, or naturally occurring lipids.

In some implementations, the lipid linked to the binding target has a phase transition temperature below about 41° C. In some implementations, the lipid linked to the binding target has a phase transition temperature between about −69° C. and 41° C., between about −60° C. and 30° C., between about −50° C. and 20° C., between about −40° C. and 10° C., between about −30° C. and 0° C., or between about −20° C. and −10° C. In some implementations, the lipid linked to the binding target has a phase transition temperature below about 0° C. In some implementations, the lipid linked to the binding target has a phase transition temperature between about −69° C. and 0° C., between about −60° C. and −10° C., between about −50° C. and −20° C., or between about −40° C. and −30° C. Examples of lipids with a phase transition temperature below 41° C. include, but are not limited to, 12:0 phosphatidylcholine (PC) (DLPC), 13:0 PC, 14:0 PC (DMPC), 15:0 PC, 16:0 PC (DPPC), 16:1 PC, 18:1c9 PC (DOPC), 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC (POPC), 16:0-22:6 PC, 18:0-14:0 PC, 18:0-18:1 PC, 18:1-16:0 PC, 18:1-18:0 PC, 12:0 phosphatidylglycerol (PG) (DLPG); 14:0 PG (DMPG), 16:0 PG (DPPG), 18:1 PG (DOPG), 16:0-18:1 PG (POPG), 14:0 phosphatidylserine (PS) (DMPS), 18:1 PS (DOPS), 16:0-18:1 PS (POPS), 12:0 phosphatidic acid (PA) (DLPA), 18:1 PA (DOPA), 16:0-18:1 PA (POPA), 12:0 phosphatidylethanolamine (PE) (DLPE), 18:1c9 PE (DOPE), 18:1t9 PE, 18:2 PE, 18:3 PE, and 16:0-18:1 PE (POPE). In some implementations, the lipid linked to the binding target includes natural-lipids with similar properties of the lipids listed above.

In some implementations, the lipid linked to the binding target is a lipid with terminal amine groups on the lipid head. Examples of lipids with terminal amine groups on the lipid head include, but are not limited to DOPE, DLPE, 18:1t9 PE, 18:2 PE, 18:3 PE, DMPE, and POPE. In some implementations, the binding target is linked to DOPE.

Liposomes

The enhanced binding of the multivalent liposomes of the present technology is, in part, related to the mobility of the binding targets on the liposome surface due to the fluidity of the lipid bilayer. As discussed above, the increased mobility of the binding targets enhances binding to multiple targets as compared to fixed binding targets or less mobile binding target because a mobile binding target can change its position relative to an adjacent bound binding target to bind a second receptor on the virus, bacteria, or toxin or bind a receptor on second virus, bacteria, or toxin.

Also discussed above, the increased mobility is relative to the fluidity of the liposome's surface membrane, which is related to phase behavior of the lipid bilayer. Fluidity is dependent of the amount of interaction, e.g., Van der Waals interactions, between the lipid tails of adjacent lipids, the ability to pack lipids, e.g., saturated verse unsaturated lipid tails, presence of cholesterol or short-chained alcohols, and temperature.

In some implementations, additional lipids, e.g., a second population of lipids, not linked to the binding target include, but are not limited to, synthetic, semi-synthetic, or naturally occurring lipids.

In some implementations, additional lipids not linked to the binding target are included in the compositions to form the liposome. In some implementations, the additional lipids not linked to the binding target have a phase transition temperature below about 41° C. In some implementations, the additional lipids not linked to the binding target have a phase transition temperature between about −69° C. and 41° C., between about −60° C. and 30° C., between about −50° C. and 20° C., between about −40° C. and 10° C., between about −30° C. and 0° C., or between about −20° C. and −10° C. In some implementations, the additional lipids not linked to the binding target have a phase transition temperature below about 0° C. In some implementations, the additional lipids not linked to the binding target have a phase transition temperature between about −69° C. and 0° C., between about −60° C. and −10° C., between about −50° C. and −20° C., or between about −40° C. and −30° C. Examples of lipids with a phase transition temperature below 41° C. include, but are not limited to, 12:0 phosphatidylcholine (PC) (DLPC), 13:0 PC, 14:0 PC (DMPC), 15:0 PC, 16:0 PC (DPPC), 16:1 PC, 18:1c9 PC (DOPC), 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC (POPC), 16:0-22:6 PC, 18:0-14:0 PC, 18:0-18:1 PC, 18:1-16:0 PC, 18:1-18:0 PC, 12:0 phosphatidylglycerol (PG) (DLPG); 14:0 PG (DMPG), 16:0 PG (DPPG), 18:1 PG (DOPG), 16:0-18:1 PG (POPG), 14:0 phosphatidylserine (PS) (DMPS), 18:1 PS (DOPS), 16:0-18:1 PS (POPS), 12:0 phosphatidic acid (PA) (DLPA), 18:1 PA (DOPA), 16:0-18:1 PA (POPA), 12:0 phosphatidylethanolamine (PE) (DLPE), 18:1c9 PE (DOPE), 18:1t9 PE, 18:2 PE, 18:3 PE, and 16:0-18:1 PE (POPE).

In some implementations, the additional lipids, e.g., a second population of lipids, are lipids with unsaturated acid fatty acid tails, i.e., with 1, 2, 3, 4 or more double bonds. In some implementations, the lipid tails of the lipids are 12 to 24 carbons in length with one or more double bonds, e.g., between 12:1-4 to 22:1-6. In some implementations, the lipids are phospholipids made from a glycerol to which two hydrocarbon chains are linked, with any head group.

In some implementations, the additional lipids are sphingomyelin, which has one fatty acid chain.

Alternatively, or additionally, in some implementations, the additional lipids, phospholipids, or sphingomyelin are modified with glycans (viral-binding or other) or other moieties such as PEG100 to PEG10,000.

In some implementations, the additional lipids, e.g., a second population of lipids, are DO-based lipids. In some implementations, the additional lipids are 18:1 lipids, i.e., the lipids have tails with 18 carbons and one unsaturated bond. In some implementations, the additional lipids are 18:2 lipids, i.e., the lipids have tails with 18 carbons and two unsaturated bond. In some implementations, the additional lipids are a combination of 18:1 and 18:2 lipids. In some implementations, the additional lipids have at least one 18:1 lipid tail. In some implementations, the additional lipids are DOPE, DOPC, DOPG, or a combination thereof. In some implementations, the additional lipids includes an amount of a lipid with a negatively charged head group (e.g., PG) to vary the proportion of glycolipids to maintain a constant average overall charge per liposome. Examples of lipids that can be used to maintain a constant average overall charge per liposome include, but are not limited to, lipids with PG head groups, e.g., DOPG, and lipids with PS head groups, e.g., DOPS. In some implementations, the additional lipids are only a single type of lipid, e.g., DOPG or DOPC.

In some implementations, the liposome is formed from a lipid mixture that includes between about 1 to 30 mol %, or between about 3 to 27 mol %, or between about 6 to 24 mol %, or between about 9 to 21 mol %, or between about 12 to 18 mol % of BT-lipid (e.g., a glycolipid such as LSTc linked to DOPE). By way of example, but not by limitation, in some implementations, the liposome is formed from a lipid mixture that includes 7.5 mol % LSTc linked DOPE.

In some implementations, the liposome is formed from a lipid mixture that includes between about 50 to 84 mol %, or between about 55 to 80 mol %, or between about 60 to 75 mol %, or between about 65 to 70 mol % of additional lipids. In some implementations, the additional lipid is DOPC, DOPG, or a combination thereof.

In some implementation, the liposome is formed from a lipid mixture that includes cholesterol and/or short-chained alcohols. In some implementations, the lipid mixture includes between about 10 to 35 mol %, or between about 15 to 30 mol %, or between about 18 to 27 mol %, or between about 21 to about 24 mol % of cholesterol. In some implementations, the cholesterol forms lipid rafts in the lipid bilayer. By way of example, but not by limitation, in some implementations, the liposome is formed from a lipid mixture that includes 30 mol % cholesterol.

In some implementations, the multivalent liposome composition includes BT-lipids, which includes LSTc linked to DOPE and is present in the liposome at about 7.5 mol %, additional lipid(s), which includes DOPC and/or DOPG and is present in the liposome at about 62.5 mol %, and cholesterol, which is present in the liposome at about 30%.

By way of example, but not by limitation, in some implementations, the liposome is formed from 30% cholesterol, 62.5% DOPC or DOPG, and 7.5% LSTc-DOPE.

In some implementations, the multivalent liposome composition is more effective in inhibiting viral or bacterial infection or toxin entry into cell or tissue than the binding target or liposome alone. In some implementations, multivalent liposome compositions are about 10-fold, 20-fold, 30-fold, 40-fold, 50-fold, 60-fold, 70-fold, 80-fold, 90-fold, 100-fold, 200-fold, 400-fold, 800-fold, 1000-fold, 1500-fold, 2000-fold more effective in inhibiting viral or bacterial infection than the binding target or liposome alone.

II. Methods for Making Liposomes

General

By way of example, but not by limitation, in some implementations, formation of a liposome includes: 1) attaching at least one binding target to a lipid, e.g., a first population of lipids, to form a BT-lipid; 2) combining at least one BT-lipid with additional lipids e.g., a second population of lipids, to form a lipid mixture; and 3) forming liposomes by pressing the lipid mixture through a membrane. In some implementations, the first population of lipids and the second population of lipids are the same. In some implementations, the first population of lipids and the second population of lipids are different.

Methods for Making BT-Lipids

Examples of lipids used in the formation of the BT-lipid are described above. By way of example, but not by limitation, in some implementations, methods useful for linking a lipid to the binding target include: 1) Reductive amination using polar aprotic solvents, e.g., DMSO, DMF or THF, using a high amine to sugar ratio, e.g., about 10-100:1 at a pH of about 4-5; 2) Click chemistry between an azide and an alkyne in biological buffers at a ratio of 1:1; 3) Aminooxy conjugation in biological buffers at a ratio of 1:1 at a pH of about 4-5; 4) Hydrazide or semicarbazide at a ratio of about 1-5:1 at a pH of about 4-5. It should be noted that a skilled artisan could use other known methods of linking a binding target to a lipid based on the type of binding target and the lipid being used.

By way of example, but not by way of limitation, in some implementations, the binding target is LSTc, and the lipid is DOPE. In some implementations, the LSTc and DOPE are linked by reductive amination.

In some implementations, the lipid linked to the binding target includes, but is not limited to, synthetic, semi-synthetic, or naturally occurring lipids.

In some implementations, the lipid linked to the binding target, e.g., a first population of lipids, has a phase transition temperature below about 41° C. In some implementations, the lipid linked to the binding target has a phase transition temperature between about −69° C. and 41° C., between about −60° C. and 30° C., between about −50° C. and 20° C., between about −40° C. and 10° C., between about −30° C. and 0° C., or between about −20° C. and −10° C. In some implementations, the lipid linked to the binding target has a phase transition temperature below about 0° C. In some implementations, the lipid linked to the binding target has a phase transition temperature between about −69° C. and 0° C., between about −60° C. and −10° C., between about −50° C. and −20° C., or between about −40° C. and −30° C. Examples of lipids with a phase transition temperature below 41° C. include, but are not limited to, 12:0 phosphatidylcholine (PC) (DLPC), 13:0 PC, 14:0 PC (DMPC), 15:0 PC, 16:0 PC (DPPC), 16:1 PC, 18:1c9 PC (DOPC), 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC (POPC), 16:0-22:6 PC, 18:0-14:0 PC, 18:0-18:1 PC, 18:1-16:0 PC, 18:1-18:0 PC, 12:0 phosphatidylglycerol (PG) (DLPG); 14:0 PG (DMPG), 16:0 PG (DPPG), 18:1 PG (DOPG), 16:0-18:1 PG (POPG), 14:0 phosphatidylserine (PS) (DMPS), 18:1 PS (DOPS), 16:0-18:1 PS (POPS), 12:0 phosphatidic acid (PA) (DLPA), 18:1 PA (DOPA), 16:0-18:1 PA (POPA), 12:0 phosphatidylethanolamine (PE) (DLPE), 18:1c9 PE (DOPE), 18:1t9 PE, 18:2 PE, 18:3 PE, and 16:0-18:1 PE (POPE). In some implementations, the lipid linked to the binding target includes natural-lipids with similar properties of the lipids listed above.

In some implementations, the lipid linked to the binding target e.g., a first population of lipids, is a lipid with terminal amine groups on the lipid head. Examples of lipids with terminal amine groups on the lipid head include, but are not limited to DOPE, DLPE, 18:1t9 PE, 18:2 PE, 18:3 PE, DMPE, and POPE. In some implementations, the binding target is linked to DOPE.

Liposome Formation

In some implementations, one or more BT-lipids (e.g., LSTc linked to DOPE) is combined with a plurality of at least one additional lipid e.g., a second population of lipids, to form a lipid mixture that will be used to make liposomes. In some implementations, the additional lipids are mixed in chloroform before mixing with the BT-lipid. In some implementations, the additional lipids are mixed in methanol or other alcohols (e.g., t-butyl alcohol) before mixing with the BT-lipid. In some implementations, the BT-lipid is in water before mixing with the additional lipids. In some implementations, methanol is added to the chloroform, water mixtures. In some implementations, the water mixture with the BT-lipid and the chloroform mixture of additional lipids are combined at room temperature.

In some implementations, the additional lipids e.g., a second population of lipids, include, but are not limited to, synthetic, semi-synthetic, or naturally occurring lipids.

In some implementations, the additional lipids have a phase transition temperature below about 41° C. In some implementations, the additional lipids not linked to the binding target have a phase transition temperature between about −69° C. and 41° C., between about −60° C. and 30° C., between about −50° C. and 20° C., between about −40° C. and 10° C., between about −30° C. and 0° C., or between about −20° C. and −10° C. In some implementations, the additional lipids not linked to the binding target have a phase transition temperature below about 0° C. In some implementations, the additional lipids not linked to the binding target have a phase transition temperature between about −69° C. and 0° C., between about −60° C. and −10° C., between about −50° C. and −20° C., or between about −40° C. and −30° C. Examples of lipids with a phase transition temperature below 41° C. include, but are not limited to, 12:0 phosphatidylcholine (PC) (DLPC), 13:0 PC, 14:0 PC (DMPC), 15:0 PC, 16:0 PC (DPPC), 16:1 PC, 18:1c9 PC (DOPC), 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC (POPC), 16:0-22:6 PC, 18:0-14:0 PC, 18:0-18:1 PC, 18:1-16:0 PC, 18:1-18:0 PC, 12:0 phosphatidylglycerol (PG) (DLPG); 14:0 PG (DMPG), 16:0 PG (DPPG), 18:1 PG (DOPG), 16:0-18:1 PG (POPG), 14:0 phosphatidylserine (PS) (DMPS), 18:1 PS (DOPS), 16:0-18:1 PS (POPS), 12:0 phosphatidic acid (PA) (DLPA), 18:1 PA (DOPA), 16:0-18:1 PA (POPA), 12:0 phosphatidylethanolamine (PE) (DLPE), 18:1c9 PE (DOPE), 18:1t9 PE, 18:2 PE, 18:3 PE, and 16:0-18:1 PE (POPE).

In some implementations, the additional lipids are lipids with unsaturated acid fatty acid tails, i.e., with 1, 2, 3, 4 or more double bonds. In some implementations, the lipid tails of the lipids are 12 to 24 carbons in length with one or more double bonds, e.g., between 12:1-4 to 22:1-6. In some implementations, the lipids are phospholipids made from a glycerol to which two hydrocarbon chains are linked, with any head group.

In some implementations, the lipids are sphingomyelin, which has one fatty acid chain.

Alternatively, or additionally, in some implementations, the lipids, phospholipids, or sphingomylein are modified with glycans (viral-binding or other) or other moieties such as PEG100 to PEG10,000.

In some implementations, the additional lipids e.g., a second population of lipids, are DO-based lipids. In some implementations, the additional lipids are 18:1 lipids, i.e., the lipids have tails with 18 carbons and one unsaturated bond. In some implementations, the additional lipids are 18:2 lipids, i.e., the lipids have tails with 18 carbons and two unsaturated bond. In some implementations, the additional lipids are a combination of 18:1 and 18:2 lipids. In some implementations, the additional lipids have at least one 18:1 lipid tail. In some implementations, the additional lipids are DOPE, DOPC, DOPG, or a combination thereof. In some implementations, the additional lipids includes an amount of a lipid with a negatively charged head group (e.g., PG) to vary the proportion of glycolipids to maintain a constant average overall charge per liposome. Examples of lipids that can be used to maintain a constant average overall charge per liposome include, but are not limited to, lipids with PG head groups, e.g., DOPG, and lipids with PS head groups, e.g., DOPS. In some implementations, the additional lipids are only a single type of lipid, e.g., DOPG.

In some implementations, the liposome is formed from a lipid mixture that includes between about 1 to 30 mol %, or between about 3 to 27 mol %, or between about 6 to 24 mol %, or between about 9 to 21 mol %, or between about 12 to 18 mol % of BT-lipid (e.g., a glycolipid such as LSTc linked to DOPE). By way of example, but not by limitation, in some implementations, the liposome is formed from a lipid mixture that includes 7.5 mol % LSTc linked DOPE.

In some implementations, the liposome is formed from a lipid mixture that includes between about 50 to 84 mol %, or between about 55 to 80 mol %, or between about 60 to 75 mol %, or between about 65 to 70 mol % of additional lipids. In some implementations, the additional lipid is DOPC, DOPG, or a combination thereof.

In some implementation, the liposome is formed from a lipid mixture that includes cholesterol and/or short-chained alcohols. In some implementations, the lipid mixture includes between about 10 to 35 mol %, or between about 15 to 30 mol %, or between about 18 to 27 mol %, or between about 21 to about 24 mol % of cholesterol. In some implementations, the cholesterol forms lipid rafts in the lipid bilayer. By way of example, but not by limitation, in some implementations, the liposome is formed from a lipid mixture that includes 30 mol % cholesterol.

Figure 10:
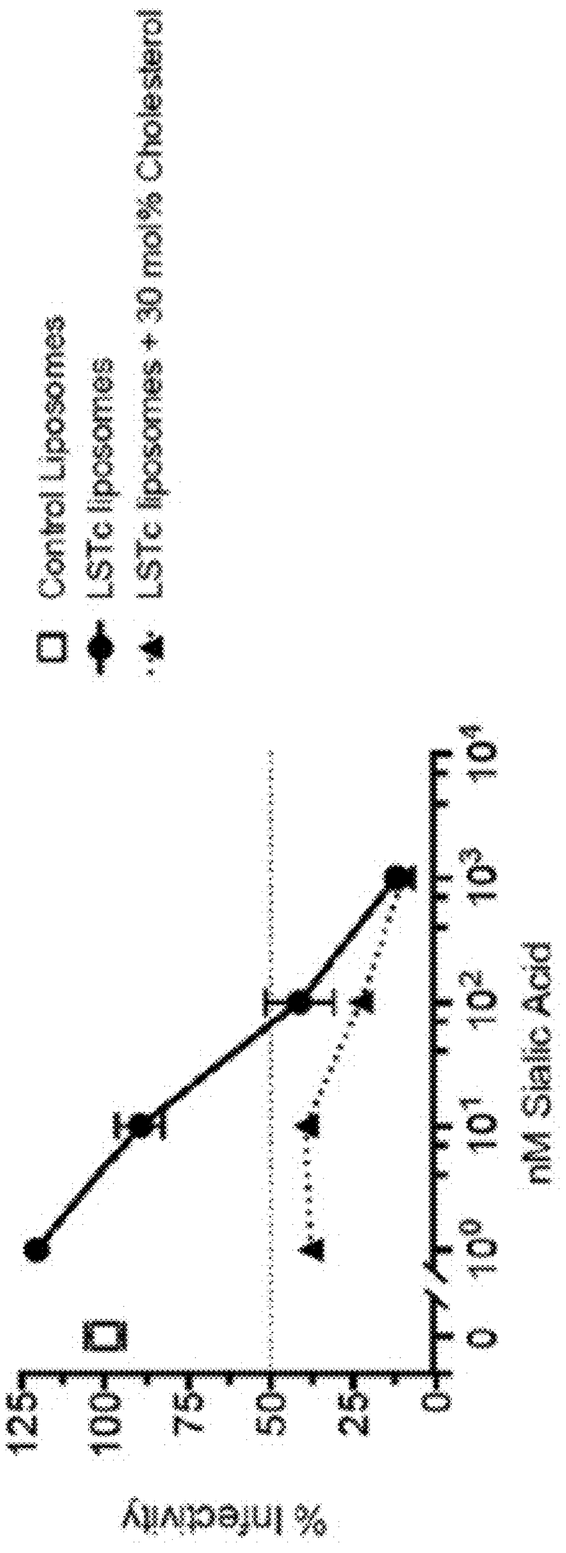
FIG. 10 is a graph showing the inhibitory activity of LSTc liposomes and LSTc liposomes with 30 mol % cholesterol.
Figure 11:
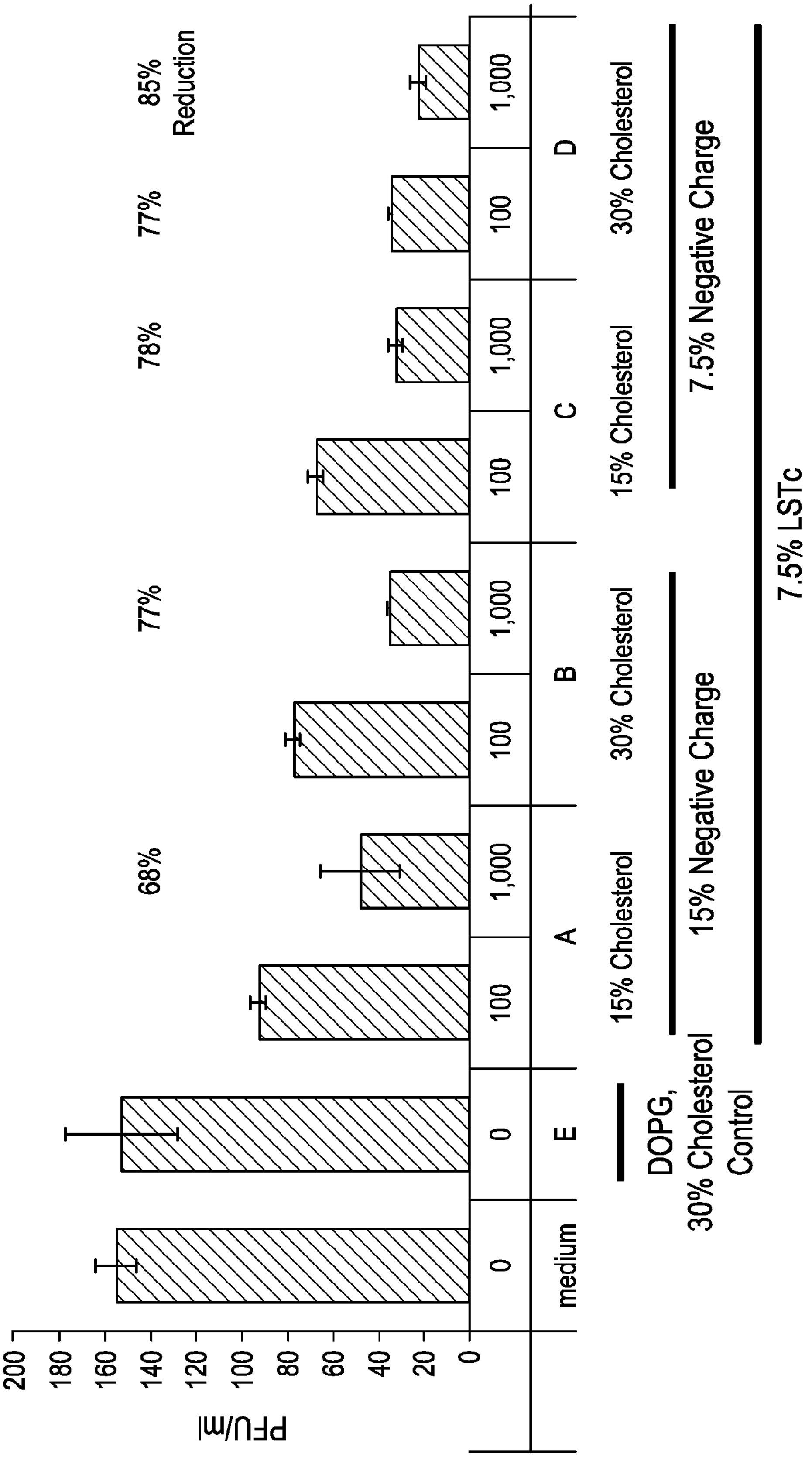
FIG. 11 is a graph showing the inhibitory of activity of LSTc liposomes with 15 and 30 mol % cholesterol.

In some implementations, about 15-30 mol % cholesterol in the liposome enhances the inhibitory activity of the multivalent liposome compositions (see FIGS. 10-11).

In some implementations, the multivalent liposome composition is formed from a mixture containing BT-lipids, which includes LSTc linked to DOPE and is present in the liposome at about 7.5 mol %, additional lipid(s), which includes DOPC and/or DOPG and is present in the liposome at about 62.5 mol %, and cholesterol, which is present in the liposome at about 30%.

In some implementations, the glycolipids/additional lipid mixture is extruded through a membrane to form liposomes. In some implementations, the pores in the membrane are about 25 nm, about 50 nm, about 100 nm, about 200 nm, about 300 nm, about 400 nm, about 500 nm, about 600 nm, about 700 nm, about 800 nm, about 900 nm, about 1000 nm, or any ranges between any two of these values. In some implementations, the membrane is an aluminum oxide membrane or a polycarbonate membrane. In some implementations, extrusions through the membrane are between about 5 to 30 passes, or about 10 to 25 passes, or about 15 to 20 passes.

III. Methods of Treatment/Administration/Formulations

General

The liposome compositions described herein are useful to reduce, prevent, or treat viral and bacterial infections. Additionally, the liposome composition described herein are used to reduce, prevent, or treat exposure to a toxin. The disclosure provides for both prophylactic and therapeutic methods of treating a subject having or at risk of viral or bacterial infection or having been exposed or at risk for exposure to toxins. Accordingly, the present methods provide for the prevention and/or treatment of viral infection, bacterial infection, or toxin exposure in a subject by administering an effective amount of the multivalent liposome composition disclosed herein to a subject in need thereof. By way of example, but not by limitation, in some implementations, the multivalent liposome composition is able to treat or prevent viral infection by, but not limited to, influenza A, Cercopithecine herpes virus 1, Arenavirus, Picornavirus, Orthomyxovirus, Paramyxovirus, Reovirus, Alphavirus, Filovirus, Polyomavirus, Herpes B, and respiratory syncytial virus. By way of example, but not by limitation, in some implementations, the liposome composition is able to treat or prevent bacterial infection by, but not limited to, *Mycoplasma pneumonia, Pseudomonas aeruginosa, Streptococcus pneumonia*, and *Haemophilus influenzae*. By way of example, but not by limitation, in some implementations, the multivalent liposome composition is able to treat or prevent the effects of toxins, which include, but are not limited to, ricin, abrin, shiga, tetanus, botulinum A-E, *C. difficile* toxin A, cholera, pertussis, *E. coli* heat-labile enterotoxin, streptolysin O, and *staph* enterotoxin.

Therapeutic and prophylactic methods include administering an effective amount of a multivalent liposomal composition described herein to a subject in need thereof. The multivalent liposomal composition includes multiple binding targets to which the virus, bacteria, or toxin will bind. In effect, the multivalent liposome composition reduces or prevents viruses, bacteria, or toxins from binding to cellular binding targets on the cell or tissue surface, which reduces or prevents entry of the virus, bacteria, or toxin into the cell or tissue.

Therapeutic Methods

One aspect of the present technology includes methods of treating viral infection, bacterial infection, and toxin exposure in a subject for therapeutic purposes. In therapeutic applications, compositions or medicaments are administered to a subject suspected of, or already suffering from, a viral infection, bacterial infection, or toxin exposure in an amount sufficient to cure, or at least partially arrest, the symptoms of the disease or exposure, including its complications and intermediate pathological phenotypes in development of the disease or exposure. As such, the present technology provides methods of treating an individual with a viral infection, bacterial infection, or exposure to toxin.

Subjects suffering from viral or bacterial infection can be identified by any or a combination of diagnostic or prognostic assays known in the art. For example, typical symptoms of viral and bacterial infection include, but are not limited to, e.g., sneezing, muscle aches, fever, congestion (sinus or bronchial), coughing, headaches, bronchiolitis, vomiting, fatigue, cramping, chills, and diminished appetite.

Subjects suffering from exposure to toxins can be identified by any or a combination of diagnostic or prognostic assays known in the art. For example, typical symptoms of toxin exposure include, but are not limited to, e.g., sneezing, muscle aches, fever, congestion (sinus or bronchial), coughing, headaches, bronchiolitis, vomiting, fatigue, cramping, chills, and diminished appetite.

Prophylactic Methods

In one aspect, the invention provides a method for preventing, in a subject, viral infection by administering an effective amount of the sulfated polysaccharide, liposomes, linked compositions, or a combination thereof that prevents the initiation or progression of viral infection. Subjects at risk for viral infection can be identified by, e.g., any or a combination of diagnostic or prognostic assays as known in the art. In prophylactic applications, pharmaceutical compositions or medicaments of the sulfated polysaccharide, liposomes, linked compositions, or a combination thereof are administered to a subject susceptible to, or otherwise at risk for viral infection in an amount sufficient to eliminate or reduce the risk, lessen the severity, or delay the progression of the infection. Administration of a prophylactic sulfated polysaccharide, liposomes, linked compositions, or a combination thereof can occur prior to the manifestation of symptoms characteristic of viral infection, such that a viral infection is prevented or, alternatively, delayed in its progression.

For both the therapeutic and prophylactic methods, subjects are administered the multivalent liposome composition to treat or prevent viral infection, bacterial infection, and exposure to toxins. By way of example, but not by limitation, a subject infected with influenza A, would be treated with an effective amount of LSTc liposomes. In some implementations, the LSTc liposome includes BT-lipids comprising LSTc linked to DOPE, cholesterol, DOPC, and DOPG, wherein the liposome has a fluid lipid bilayer, wherein LSTc is displayed on the outer surface of the lipid bilayer, and wherein the cholesterol is 15 to 30 mol % of the liposome.

Determination of the Biological Effect of the Liposomal Composition Therapeutic.

In various implementations, suitable in vitro or in vivo assays are performed to determine the effect of a specific liposome composition based therapeutic and whether its administration is indicated for treatment. In various implementations, in vitro assays are performed with representative animal models to determine if a given sulfated polysaccharide, liposome, linked composition, or a combination thereof based therapeutic exerts the desired effect in preventing or treating viral infection. Compounds for use in therapy are tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

V. Modes of Administration and Effective Dosages

Any method known to those in the art for contacting a cell, organ, or tissue with a multivalent liposome composition may be employed. Suitable methods include in vitro, ex vivo, or in vivo methods. In vivo methods typically include the administration of at least one multivalent liposome composition, such as those described above, to a mammal or avian, e.g., a human or a bird. When used in vivo for therapy, the multivalent liposome composition is administered to the subject in effective amounts (i.e., amounts that have desired therapeutic effect). The dose and dosage regimen will depend upon the degree of the infection in the subject, the characteristics of the particular multivalent liposome composition used, e.g., its therapeutic index, the subject, and the subject's history.

In some implementations, the effective amount is determined during pre-clinical trials and clinical trials by methods familiar to physicians and clinicians. An effective amount of a multivalent liposome composition useful in the methods is administered to a subject in need thereof by any of a number of well-known methods for administering pharmaceutical compounds. The multivalent liposome composition can be administered systemically or locally (e.g., by inhalation).

In some implementations, the dosage for a therapeutic effect by is about 0.1 mg to about 100 mg per dose. The dosage can change depending on the active formulation, method of delivery, and individual.

In some embodiments, doses would be given about every 4 hours, 8 hours, or 12 hours, 16 hours, 24 hours, 36 hours, 48 hours, 60 hours, or 72 hours, or any ranges between any two of these values.

In some implementations, the multivalent liposome composition described herein is incorporated individually or in combination into pharmaceutical compositions for administration to a subject for the treatment or prevention of viral infections, bacterial infections, and exposure to toxins described herein.

Pharmaceutical compositions are typically formulated to be compatible with its intended route of administration. Examples of routes of administration include parenteral (e.g., intravenous, intradermal, intraperitoneal or subcutaneous), oral, inhalation, iontophoretic, intranasal, and transmucosal administration.

In some implementations, the multivalent liposome composition is stored in liquid, which would be delivered to the airway of humans using an inhalational delivery device.

VI. Kits

In some implementations, the compositions of the present technology are provided in a kit.

In some implementations, a kit includes at least one liposome composition, wherein the liposome composition includes a plurality of lipids e.g., a first population of lipids and second population of lipids, cholesterols, and at least two binding targets, wherein the lipids and cholesterols form a liposome, wherein the binding targets are linked to a first population of lipids and displayed on an outer surface of the liposome, wherein the lipids have a phase transition temperature below about 41° C., and wherein the cholesterol is about 10 to 35 mol %, or between about 15 to 30 mol %, or between about 18 to 27 mol %, or between about 21 to 24 mol % of the liposome. In some implementations, the lipids have a phase transition temperature between about −69° C. and 41° C., between about −60° C. and 30° C., between about −50° C. and 20° C., between about −40° C. and 10° C., between about −30° C. and 0° C., or between about −20° C. and −10° C. In some implementations, the additional lipids not linked to the binding target have a phase transition temperature below about 0° C. In some implementations, the additional lipids not linked to the binding target have a phase transition temperature between about −69° C. and 0° C., between about −60° C. and −10° C., between about −50° C. and −20° C., or between about −40° C. and −30° C.

In some implementations, the kit also includes tools (e.g., a syringe or nebulizer) for delivery of the liposome composition.

In some implementations, the lipids in the lipid bilayer include, but are not limited to, 12:0 phosphatidylcholine (PC), 13:0 PC, 14:0 PC, 15:0 PC, 16:0 PC, 16:1 PC, 18:1c9 PC, 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC, 16:0-22:6 PC, 18:0-14:0 PC, 18:0-18:1 PC, 18:1-16:0 PC, 18:1-18:0 PC, 12:0 phosphatidylglycerol (PG); 14:0 PG, 16:0 PG, 18:1 PG, 16:0-18:1 PG, 18:1 phosphatidylserine (PS), 16:0-18:1 PS, 12:0 phosphatidic acid (PA), 18:1 PA, 16:0-18:1 PA, 12:0 phosphatidylethanolamine (PE), 18:1c9 PE, 18:1t9 PE, 18:2 PE, 18:3 PE, 16:0-18:1 PE, or a combination thereof. In some implementations, the lipid bilayer includes only 18:1 lipids and cholesterol, wherein the cholesterol is about 10 to 35 mol %, or between about 15 to 30 mol %, or between about 18 to 27 mol %, or between about 21 to 24 mol % of the liposome. In some implementations, the 18:1 lipids include DOPE, DOPC, DOPG, or a combination thereof.

In some implementations, the binding targets bind to viruses. In some implementations, the binding targets bind to influenza A (IAV). Examples of binding targets that reduce or prevent IAV infection include, but are not limited to, sialylneolacto-N-tetraose c (LSTc), α-5-N-acetyl-neuraminic acid (Neu5Ac), Neu5Acα2-3Galβ1-4GlcNAc, Neu5Acα2-6Galβ1-4GlcNAc, Neu5Acα2-3Galβ1-4GlcNAβ1-3Galβ14GlcNAc, Neu5Acα2-6Galβ1-4GlcNAcβ1-3Galβ1-4GlcNAc, Neu5Acα2-3Galβ1-4GlcNAcβ11-3Galβ1-4GlcNAcβ1-3Galβ1-4GlcNAc, Neu5Acα6Galβ4GlcNAcβ3Galβ4Glc, Neu5Acα3Galβ4GlcNAc, Neu5Acα6Galβ4GlcNAc, Neu5Acα3Gal, Neu5Acα6Gal, Neu5Acα3Galβ4Glc, Neu5Acα3Galβ3GlcNAc, Neu5Acα2-6Galβ1-4GlcNAcβ1-3Galβ1-4GlcNAc-, Neu5Acα2-6GalNAcβ1-4GlcNAcβ1-3GalNAcβ1-4GlcNAc-, Neu5Acα2-6GlcNAcβ1-3Galβ1-3/4GlcNAc-, Neu5Acα2-6Galβ1-4GlcNAcβ1-3Galβ1-3GalNAcα, Neu5Acα2-6Galβ1-4GlcNAcβ1-3Galβ1-4GlcNAcβ1-3Galβ1-3GalNAcα, Neu5Acα2-6GalNAcβ1-4GlcNAcβ1-3Galβ1-3GalNAcα, Neu5Acα2-6GalNAcβ1-4GlcNAcβ1-3GalNAcβ1-4GlcNAcβ1-3Galβ1-3GalNAcα, Neu5Acα2-6GalNAcα-β1-3Galα2-3Neu5Ac, Neu5Acα2-6Galβ1-4GlcNAcβ1-3/6GalNAcα, Neu5Acα2-6Galβ1-4GlcNAcβ1-3Galβ1-4GlcNAcβ1-3/6GalNAcα, Neu5Acα2-6GalNAcβ1-4GlcNAcβ1-3/6GalNAcα, Neu5Acα2-6GalNAcβ1-4GlcNAcβ1-3GalNAcβ1-4GlcNAcβ1-3/6GalNAcα, Neu5Acα2-6Galβ1-4GlcNAcβ1-6GalNAcα-β1-3Galα2-3Neu5Ac, Neu5Acα2-6Galβ1-4GlcNAcβ1-3/6GalNAcα-β1-3/6GlcNAcβ1-4Galα2-3/6Neu5Ac, Neu5Acα2-6GlcNAcβ1-3Galβ1-4GlcNAcβ1-3Galβ1-3GalNAc, Neu5Acα2-6GlcNAcβ1-3Galβ1-3GlcNAcβ1-3/6GalNAc, Neu5Acα2-6GlcNAcβ1-3Galβ1-4GlcNAcβ1-3/6GalNAc, Neu5Acα2-6Galβ1-3GalNAcβ1-4Galα1-3Galβ1-4Glc, Neu5Acα2-6Galβ1-4GlcNAcβ1-3Galβ1-4Glc, Neu5Acα2-6Galβ1-3GalNAcβ1-3Gal1α-4Galβ1-4Glc, Neu5Acα2-6Galβ1-3GlcNAcβ1-3Galβ1-4Glc, Neu5α2-6Galβ1-4GlcNAcβ1-3GalNAcα, Neu5Acα2-6Galβ1-4GlcNAcβ1~3Gal-1-3GalNAcα, Neu5Acα2-6GalNAc(β1-3Gal)β1-4Galβ1-4Glc, and Neu5Acα2-6GalNAc(β1-3Gal-)β1-3Galα1-4Galβ1-4Glc. In some implementations, the binding target is LSTc.

In some implementations, the IAV binding target is a umbrella-topology glycan. In some implementations, the umbrella-topology glycan has the structure of Neu5Acα2-6Sug1-Sug2-Sug3-Sug4, wherein one or more of the following conditions are met: 1) Neu5Ac α2-6 is at the non-reducing end of the glycan; 2) Sug1, Sug2, Sug3, or Sug4 is a hexose or hexosamine in a or β configuration; 3) no sugars other than Neu5Acα2-6 are attached to any of the non-reducing positions of Sug1; 4) non-sugar moieties are attached to non-reducing positions of Sug1, Sug2, Sug3, or Sug4; 5) Linkage between any two sugars in the oligosaccharide apart from Neu5Acα2-6 linkage are 1-2, 1-3, 1-4, and/or 1-6; and 6) the Neu5Acα2-6Sug1-Sug2-Sug3-portion satisfies structural constraints or hemagglutinin contact constraints of the umbrella-like topology glycan.

In some implementations, the binding target is specific for a non-IAV virus. Examples of non-IAV viruses include, but are not limited to, Cercopithecine herpes virus 1, Arenavirus (e.g., Lassa virus), Picornavirus (e.g., foot-and-mouth and Enterovirus 71), Orthomyxovirus (e.g., influenza B), influenza C, Paramyxovirus (e.g., parainfluenza), Reovirus (e.g., rotavirus and norovirus), Alphavirus (e.g., Eastern equine encephalitis), Filovirus (e.g., Marburg virus), Polyomavirus (e.g., human polyomaviruses), Herpes B, epidemic keratoconjunctivitis virus, adenovirus, and respiratory syncytial virus (RSV). Examples of binding targets that reduce or prevent non-IAV viral infection include, but are not limited to, anyone of the above listed binding targets, α-Dystroglycan (for use against Lassa virus), asialoglycoprotein (for use against Marburg virus), sialyl Lewis (for use against norovirus), Neu5Ac(α2-3)Gal(β1-4)Glc (for use against rotavirus), Neu5Acα2Me (for use against rotavirus), dextran sulphate, heparin, chondrotin sulphate B (for use against RSV), NeuAcα2-3Galβ1-4GlcNAc (for use against human parainfluenza virus type 1), NeuGcα2-3Galβ1-4GlcNAc, NeuAcα2-6Galβ1-4GlcNAc, NeuAcα2-3Galβ1-4GlcNAc (for use against human parainfluenza virus type 1), NeuAc (α2-3)Gal (for use against influenza B), and N-acetyl-9-O-NeuAc(α2-3)Gal (for use against influenza C).

In some implementations, the binding targets bind to bacteria. In some implementations, the binding targets bind to bacteria that include, but are not limited to, *Mycoplasma pneumonia, Pseudomonas aeruginosa, Streptococcus pneumonia*, and *Haemophilus influenzae*. Binding targets that bind to bacteria include, but are not limited to, Galβ1-3GalNAcβ1-4(NeuAcα2-3)Galβ1-4Glcβ1-1Cer, dextran, sialylated glycolipids, Lewis$^{4}$, fibronectin, laminin, collagen I, collagen III, amphotericin B, dextran sulphate, Fucα2GalβGlcNAc, Manα3Manα6Man, Galα4Gal, NeuAc (α2-3)Galβ3GalNAc, NeuAc (α2-8), GalNAcβ4Galβ, GlcNAc, GlcNAcβ4GlcNAc, NeuAc(α2-3)Galβ4Glc, NeuAc(α2-3)Galβ4GlcNAc, Fucα2Galβ3(Fucα4)Gal, Man, Galβ4Glc(NAc), [NeuAc(α2-3)]0,1, Galβ4GlcNAcβ3Galβ4GlcNAc, L-Fuc, Galβ3Glc(NAc) β3Galβ4Glc, and Galα4Galβ4Glc.

In some implementations, the binding targets bind to toxins. In some implementations, the toxins are bacterial toxins. In some implementations, the binding targets bind to a toxin that include, but are not limited to, ricin, abrin, shiga, tetanus, botulinum A-E, *C. difficile* toxin A, cholera, pertussis, *E. coli* heat-labile enterotoxin, streptolysin O, and *staph* enterotoxin. Binding targets that bind to a toxin include, but are not limited to, GT1b, GQ1b, GD1a, phosphatidylethanolamine, unsaturated fatty acids, synaptotagmins I and II, digalactosylceramide, Lewisa, Asialo-GM1, lactosylceramide, and N-acetyllactosamine glycans.

In some implementations, a kit includes a first container having a plurality of a first population of lipids, a second container having a plurality of cholesterol, a third container having a plurality of binding targets, and a fourth container having a second population of lipids, wherein the first and second population of lipids have a phase transition temperature below about 37° C., or about 38° C., or about 39° C., or about 40° C., or about 41° C. In some implementations, the first population of lipids and the second population of lipids are the same. In some implementations, the first population of lipids and the second population of lipids are different. In some implementations, the kit includes a tool for extrusion of a lipid mixture through the membrane. In some implementations, the membrane has pores that are about 50 nm, about 100 nm, about 150 nm, about 200 nm, about 250 nm, about 300 nm. In some implementations, the kit also includes instructions for making a multivalent liposome composition.

In some implementations, the lipids in the first container and fourth container, e.g., the first and second population of lipids, respectively, include, but are not limited to, synthetic, semi-synthetic, or naturally occurring lipids. In some implementations, the first and second population of lipids, are selected from, but not limited to, 12:0 phosphatidylcholine (PC), 13:0 PC, 14:0 PC, 15:0 PC, 16:0 PC, 16:1 PC, 18:1c9 PC, 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC, 16:0-22:6 PC, 18:0-14:0 PC, 18:0-18:1 PC, 18:1-16:0 PC, 18:1-18:0 PC, 12:0 phosphatidylglycerol (PG); 14:0 PG, 16:0 PG, 18:1 PG, 16:0-18:1 PG, 18:1 phosphatidylserine (PS), 16:0-18:1 PS, 12:0 phosphatidic acid (PA), 18:1 PA, 16:0-18:1 PA, 12:0 phosphatidylethanolamine (PE), 18:1c9 PE, 18:1t9 PE, 18:2 PE, 18:3 PE, 16:0-18:1 PE, or a combination thereof. In some implementations, the plurality of lipids in the first contain are DOPE. In some implementations, the mixture of lipids is only 18:1 lipids. In some implementations, the mixture of lipids is only 18:1 and 18:2 lipids. In some implementations, the mixture of lipids is DOPE, DOPC, DOPG, or a combination thereof. In some implementations, the first population of lipids and the second population of lipids are the same. In some implementations, the first population of lipids and the second population of lipids are different.

VII. Combination Therapy with Multivalent Liposome Composition and Other Therapeutic Agents In some implementations, the multivalent liposome composition is combined with one or more additional agents for the prevention or treatment of viral infection. For example, current treatments for viral infection includes, but is not limited to, ribavirin, favipiravir, peramivir, amantadine, rimantadine, zanamivir, oseltamivir, protease inhibitors, rifampicin, neuraminidase, and interferons. A skilled artisan would be able to select other anti-viral agents based on the type of viral infection. In some implementations, the multivalent liposome composition is combined with ribavirin, favipiravir, peramivir, amantadine, rimantadine, zanamivir, oseltamivir, protease inhibitors, rifampicin, neuraminidase, interferons, or a combination thereof.

In some implementations, the multivalent liposome composition is combined with one or more additional agents for the prevention or treatment of bacterial infection. For example, current treatments for bacterial infections or includes, but is not limited to, amoxicillin, cefazolin, ciavulanate, moxifloxacin, azithromycin, sulfamethoxazole, trimethoprim, ceftriaxone, levofloxacin, penicillin, cephalexin, and metronidazole. A skilled artisan would be able to select other anti-bacterial agents based on the type of bacterial infection. In some implementations, the multivalent liposome composition is combined with amoxicillin, cefazolin, ciavulanate, moxifloxacin, azithromycin, sulfamethoxazole, trimethoprim, ceftriaxone, levofloxacin, penicillin, cephalexin, metronidazole, Cephaolsporins (1st to 4th and next generation, cefaclor, cefuroxime); penicillins (amoxicillin, ampicillin, piperacillin); fluoroquinolones (ciprofloxacin, oflaxacin); macrolides (clarithomycin, erythromycin, clindamycin, azithromycin); tetracyclines (minocycline, doxycycline), aminoglycosides (gentamicin, tobramycin, amikacin), glycopeptides (vancomycin), other systemic antibiotics (imipenem, rifampin), fosfomycins; monobactams (aztreonam); carbenpenems (imipenem, meropenem, ertalenem); phenocols (cholampehenical); glycylcyclines (tigecycline); oxazolidinones (linezolid), ansamycins (rifampin); Antimicrobial peptides (LL37, cathepsin), lipopeptides (polymixins, cyclic lipopeptides); sulfonamides; trimethoprim/sulfamethoxazole; quinolones (furanes); other types of non-antibiotic antimicrobials (triclosan, chlorhexidine, quaterenary ammonium compounds, silver compounds, natural oils), or a combination thereof.

In some implementations, the combination with another therapeutic agent produces a synergistic therapeutic effect. Therefore, lower doses of one or both of the therapeutic agents is used in treating viral infection, bacterial infection, or exposure to toxins, resulting in increased therapeutic efficacy and decreased side effects.

In some implementations, multiple therapeutic agents, e.g., multivalent liposome and zanamivir, are administered separately in any order or even simultaneously. If simultaneously, the multiple therapeutic agents can be provided in a single, unified form, or in multiple forms (by way of example only, either as a single pill or as two separate pills). In some implementations, one of the therapeutic agents is given in multiple doses. In another implementation, both therapeutic agents are given as multiple doses.

VIII. Exemplary Implementations

In a first exemplary implementation, methods of treating bacterial infection are presented. In some implementations, a method for treating or preventing bacterial infection includes administering an effective amount of a liposome composition, wherein the liposome composition comprises at least two binding targets, wherein the binding targets are linked to lipids (e.g., a first population of lipids) to form BT-lipids, a mixture of lipids (e.g., a second population of lipids), and a plurality of cholesterols, wherein the BT-lipids, the mixture of lipids and cholesterols form a liposome, wherein the binding targets are displayed on the outer surface of the liposome, wherein the mixture of lipids have a phase transition temperature below 41° C., and wherein the cholesterol is about 15 to 30 mol % of the liposome. In some implementations, the binding targets are select from the group consisting of amphotericin B, dextran sulphate, Fucα2GalβGlcNAc, Manα3Manα6Man, Galα4Gal, NeuAc (α2-3) Galβ3GalNAc, NeuAc (α2-8), GalNAcβ4Galβ, GlcNAc, GlcNAcβ4GlcNAc, NeuAc(α2-3)Galβ4Glc, NeuAc(α2-3) Galβ4GlcNAc, Fucα2Galβ3(Fucα4)Gal, Man, Galβ4Glc (NAc), [NeuAc(α2-3)]0,1, Galβ4GlcNAcβ3Galβ4GlcNAc, L-Fuc, Galβ3Glc(NAc)β3Galβ4Glc, and Galα4Galβ4Glc. In some implementations, the bacterial infection is caused by one or more bacteria selected from the group consisting of *Mycoplasma pneumonia, Pseudomonas aeruginosa, Streptococcus pneumonia*, and *Haemophilus influenzae*.

In another exemplary implementation, multivalent liposome compositions for treating or preventing bacterial infection are presented. In some implementations, a multivalent liposome compositions for treating or preventing bacterial infection includes a liposome composition including at least two binding targets, wherein the binding targets are linked to lipids, e.g., a first population of lipids, to form BT-lipids, a mixture of lipids, e.g., a second population of lipids, and a plurality of cholesterols, wherein the BT-lipids, the mixture of lipids and cholesterols form a liposome, wherein the binding targets are displayed on the outer surface of the liposome, wherein the mixture of lipids have a phase transition temperature below 41° C., and wherein the cholesterol is about 15 to 30 mol % of the liposome. In some implementations, the binding targets are select from the group consisting of amphotericin B, dextran sulphate, Fucα2GalβGlcNAc, Manα3Manα6Man, Galα4Gal, NeuAc (α2-3) Galβ3GalNAc, NeuAc (α2-8), GalNAcβ4Galβ, GlcNAc, GlcNAcβ4GlcNAc, NeuAc(α2-3)Galβ4Glc, NeuAc(α2-3) Galβ4GlcNAc, Fucα2Galβ3(Fucα4)Gal, Man, Galβ4Glc (NAc), [NeuAc(α2-3)]0,1, Galβ4GlcNAcβ3Galβ4GlcNAc, L-Fuc, Galβ3Glc(NAc)β3Galβ4Glc, and Galα4Galβ4Glc In some implementations, the lipid linked to the bind target, e.g., a first population of lipids, is selected from the group consisting of 12:0 phosphatidylcholine (PC) (DLPC), 13:0 PC, 14:0 PC (DMPC), 15:0 PC, 16:0 PC (DPPC), 16:1 PC, 18:1c9 PC (DOPC), 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC (POPC), 16:0-22:6 PC, 18:0-14:0 PC, 18:0-18:1 PC, 18:1-16:0 PC, 18:1-18:0 PC, 12:0 phosphatidylglycerol (PG) (DLPG); 14:0 PG (DMPG), 16:0 PG (DPPG), 18:1 PG (DOPG), 16:0-18:1 PG (POPG), 14:0 phosphatidylserine (PS) (DMPS), 18:1 PS (DOPS), 16:0-18:1 PS (POPS), 12:0 phosphatidic acid (PA) (DLPA), 18:1 PA (DOPA), 16:0-18:1 PA (POPA), 12:0 phosphatidylethanolamine (PE) (DLPE), 18:1c9 PE (DOPE), 18:1t9 PE, 18:2 PE, 18:3 PE, 16:0-18:1 PE (POPE), or a combination thereof. In some implementations, the lipid linked to the bind target is DOPE.

In some implementations, the mixture of lipids, e.g., a second population of lipids, is selected from the group consisting of 12:0 phosphatidylcholine (PC) (DLPC), 13:0 PC, 14:0 PC (DMPC), 15:0 PC, 16:0 PC (DPPC), 16:1 PC, 18:1c9 PC (DOPC), 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC (POPC), 16:0-22:6 PC, 18:0-14:0 PC, 18:0-18:1 PC, 18:1-16:0 PC, 18:1-18:0 PC, 12:0 phosphatidylglycerol (PG) (DLPG); 14:0 PG (DMPG), 16:0 PG (DPPG), 18:1 PG (DOPG), 16:0-18:1 PG (POPG), 14:0 phosphatidylserine (PS) (DMPS), 18:1 PS (DOPS), 16:0-18:1 PS (POPS), 12:0 phosphatidic acid (PA) (DLPA), 18:1 PA (DOPA), 16:0-18:1 PA (POPA), 12:0 phosphatidylethanolamine (PE) (DLPE), 18:1c9 PE (DOPE), 18:1t9 PE, 18:2 PE, 18:3 PE, 16:0-18:1 PE (POPE), or a combination thereof. In some implementations, the mixture of lipids are 18:1 lipids. In some implementations, the mixture of lipids is selected from the group consisting of DOPE, DOPC, DOPG, or a combination thereof.

In another exemplary implementation, methods of treating at least one toxin are presented. In some implementations, a method for preventing or reducing the effects of at least one toxin includes administering an effective amount a multivalent liposome composition, wherein the liposome composition comprises a mixture of lipids, a plurality of cholesterols, and at least two binding targets, wherein the binding targets are linked to lipids to form BT-lipids, wherein the BT-lipids, the mixture of lipids and cholesterols form a liposome, wherein the binding targets are displayed on the outer surface of the liposome, wherein the mixture of lipids have a phase transition temperature below 41° C., and wherein the cholesterol is about 15 to 30 mol % of the liposome. In some implementations, the binding targets are select from the group consisting of GT1b, GQ1b, GD1a, phosphatidylethanolamine, unsaturated fatty acids, synaptotagmins I and II, digalactosylceramide, Lewis[a], Asialo-GM1, lactosylceramide, and N-acetyllactosamine glycans. In some implementations, the toxin is selected from the group consisting of ricin, abrin, shiga, tetanus, botulinum A-E, *C. difficile* toxin A, cholera, pertussis, *E. coli* heat-labile enterotoxin, streptolysin O, and *staph* enterotoxin.

In another exemplary implementation, multivalent liposome compositions for treating, preventing, or reducing the effects of at least one toxin is presented. In some implementations, a multivalent liposome compositions for treating, preventing, or reducing the effects of at least one toxin includes a liposome composition including at least two binding targets, wherein the binding targets are linked to lipids, e.g., a first population of lipids, to form BT-lipids, a mixture of lipids, e.g., a second population of lipids, and a plurality of cholesterols, wherein the BT-lipids, the mixture of lipids and cholesterols form a liposome, wherein the binding targets are displayed on the outer surface of the liposome, wherein the mixture of lipids have a phase transition temperature below 41° C., and wherein the cholesterol is about 15 to 30 mol % of the liposome. In some implementations, the binding targets are select from the group consisting of GT1b, GQ1b, GD1a, phosphatidylethanolamine, unsaturated fatty acids, synaptotagmins I and II, digalactosylceramide, Lewis[a], Asialo-GM1, lactosylceramide, and N-acetyllactosamine glycans In some implementations, the lipid linked to the bind target, e.g., a first population of lipids, is selected from the group consisting of 12:0 phosphatidylcholine (PC) (DLPC), 13:0 PC, 14:0 PC (DMPC), 15:0 PC, 16:0 PC (DPPC), 16:1 PC, 18:1c9 PC (DOPC), 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC (POPC), 16:0-22:6 PC, 18:0-14:0 PC, 18:0-18:1 PC, 18:1-16:0 PC, 18:1-18:0 PC, 12:0 phosphatidylglycerol (PG) (DLPG); 14:0 PG (DMPG), 16:0 PG (DPPG), 18:1 PG (DOPG), 16:0-18:1 PG (POPG), 14:0 phosphatidylserine (PS) (DMPS), 18:1 PS (DOPS), 16:0-18:1 PS (POPS), 12:0 phosphatidic acid (PA) (DLPA), 18:1 PA (DOPA), 16:0-18:1 PA (POPA), 12:0 phosphatidylethanolamine (PE) (DLPE), 18:1c9 PE (DOPE), 18:1t9 PE, 18:2 PE, 18:3 PE, 16:0-18:1 PE (POPE), or a combination thereof. In some implementations, the lipid linked to the bind target is DOPE.

In some implementations, the mixture of lipids, e.g., a second population of lipids, is selected from the group consisting of 12:0 phosphatidylcholine (PC) (DLPC), 13:0 PC, 14:0 PC (DMPC), 15:0 PC, 16:0 PC (DPPC), 16:1 PC, 18:1c9 PC (DOPC), 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC (POPC), 16:0-22:6 PC, 18:0-14:0 PC, 18:0-18:1 PC, 18:1-16:0 PC, 18:1-18:0 PC, 12:0 phosphatidylglycerol (PG) (DLPG); 14:0 PG (DMPG), 16:0 PG (DPPG), 18:1 PG (DOPG), 16:0-18:1 PG (POPG), 14:0 phosphatidylserine (PS) (DMPS), 18:1 PS (DOPS), 16:0-18:1 PS (POPS), 12:0 phosphatidic acid (PA) (DLPA), 18:1 PA (DOPA), 16:0-18:1 PA (POPA), 12:0 phosphatidylethanolamine (PE) (DLPE), 18:1c9 PE (DOPE), 18:1t9 PE, 18:2 PE, 18:3 PE, 16:0-18:1 PE (POPE), or a combination thereof. In some implementations, the mixture of lipids are 18:1 lipids. In some implementations, the mixture of lipids is selected from the group consisting of DOPE, DOPC, DOPG, or a combination thereof.

In another exemplary implementation, kits for the present technology are presented. In some implementations, a kit includes a first container having a plurality of lipids, e.g., a first population of lipids, a second container having a plurality of cholesterol, a third container having a plurality of binding targets, and a fourth container having a mixture of lipids, e.g., a second population of lipids, wherein the lipids and the mixture of lipids have a phase transition temperature below 41° C. In some implementations, the first population of lipids and the second population of lipids are the same. In some implementations, the first population of lipids and the second population of lipids are different.

In some implementations, the plurality of lipids, e.g., a first population of lipids, are selected from the group consisting of 12:0 phosphatidylcholine (PC) (DLPC), 13:0 PC, 14:0 PC (DMPC), 15:0 PC, 16:0 PC (DPPC), 16:1 PC, 18:1c9 PC (DOPC), 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC (POPC), 16:0-22:6 PC, 18:0-14:0 PC, 18:0-18:1 PC, 18:1-16:0 PC, 18:1-18:0 PC, 12:0 phosphatidylglycerol (PG) (DLPG); 14:0 PG (DMPG), 16:0 PG (DPPG), 18:1 PG (DOPG), 16:0-18:1 PG (POPG), 14:0 phosphatidylserine (PS) (DMPS), 18:1 PS (DOPS), 16:0-18:1 PS (POPS), 12:0 phosphatidic acid (PA) (DLPA), 18:1 PA (DOPA), 16:0-18:1 PA (POPA), 12:0 phosphatidylethanolamine (PE) (DLPE), 18:1c9 PE (DOPE), 18:1t9 PE, 18:2 PE, 18:3 PE, 16:0-18:1 PE (POPE), or a combination thereof. In some implementations, the plurality of lipids are DOPE.

In some implementations, the mixture of lipids, e.g., a second population of lipids, is selected from the group consisting of 12:0 phosphatidylcholine (PC) (DLPC), 13:0 PC, 14:0 PC (DMPC), 15:0 PC, 16:0 PC (DPPC), 16:1 PC, 18:1c9 PC (DOPC), 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC (POPC), 16:0-22:6 PC, 18:0-14:0 PC, 18:0-18:1 PC, 18:1-16:0 PC, 18:1-18:0 PC, 12:0 phosphatidylglycerol (PG) (DLPG); 14:0 PG (DMPG), 16:0 PG (DPPG), 18:1 PG (DOPG), 16:0-18:1 PG (POPG), 14:0 phosphatidylserine (PS) (DMPS), 18:1 PS (DOPS), 16:0-18:1 PS (POPS), 12:0 phosphatidic acid (PA) (DLPA), 18:1 PA (DOPA), 16:0-18:1 PA (POPA), 12:0 phosphatidylethanolamine (PE) (DLPE), 18:1c9 PE (DOPE), 18:1t9 PE, 18:2 PE, 18:3 PE, 16:0-18:1 PE (POPE), or a combination thereof. In some implementations, the mixture of lipids are 18:1 lipids. In some implementations, the mixture of lipids comprise one type of lipid.

In some implementations, the binding targets are selected from the group consisting of LSTc, α-5-N-acetyl-neuraminic acid (Neu5Ac), Neu5Acα2-3Galβ1-4GlcNAc, Neu5Acα2-6Galβ1-4GlcNAc, Neu5Acα2-3Galβ1-4GlcNAβ1-3Galβ14GlcNAc, Neu5Acα2-6Galβ1-4GlcNAcβ1-3Galβ1-4GlcNAc, Neu5Acα2-3Galβ1-4GlcNAcβ11-3Galβ1-4GlcNAcβ1-3Galβ1-4GlcNAc, Neu5Acα6Galβ4GlcNAcβ3Galβ4Glc, Neu5Acα3Galβ4GlcNAc, Neu5Acα6Galβ4GlcNAc, Neu5Acα3Gal, Neu5Acα6Gal, Neu5Acα3Galβ4Glc, Neu5Acα3Galβ3GlcNAc, Neu5Acα2-6Galβ1-4GlcNAcβ1-3Galβ1-4GlcNAc-, Neu5Acα2-6GalNAcβ1-4GlcNAcβ1-3GalNAcβ1-4GlcNAc-, Neu5Acα2-6GlcNAcβ1-3Galβ1-3/4GlcNAc-, Neu5Acα2-6Galβ1-4GlcNAcβ1-3Galβ1-3GalNAcα, Neu5Acα2-6Galβ1-4GlcNAcβ1-3Galβ1-4GlcNAcβ1-3Galβ1-3GalNAcα, Neu5Acα2-6GalNAcβ1-4GlcNAcβ1-3Galβ1-3GalNAcα, Neu5Acα2-6GalNAcβ1-4GlcNAcβ1-3GalNAcβ1-4GlcNAcβ1-3Galβ1-3GalNAcα, Neu5Acα2-6GalNAcα-β1-3Galα2-3Neu5Ac, Neu5Acα2-6Galβ1-4GlcNAcβ1-3/6GalNAcα, Neu5Acα2-6Galβ1-4GlcNAcβ1-3Galβ1-4GlcNAcβ1-3/6GalNAcα, Neu5Acα2-6GalNAcβ1-4GlcNAcβ1-3/6GalNAcα, Neu5Acα2-6GalNAcβ1-4GlcNAcβ1-3GalNAcβ1-4GlcNAcβ1-3/6GalNAcα, Neu5Acα2-6Galβ1-4GlcNAcβ1-6GalNAcα-β1-3Galα2-3Neu5Ac, Neu5Acα2-6Galβ1-4GlcNAcβ1-3/6GalNAcα-β1-3/6GlcNAcβ1-4Galα2-3/6Neu5Ac, Neu5Acα2-6GlcNAcβ1-3Galβ1-4GlcNAcβ1-3Galβ1-3GalNAc, Neu5Acα2-6GlcNAcβ1-3Galβ1-3GlcNAcβ1-3/6GalNAc, Neu5Acα2-6GlcNAcβ1-3Galβ1-4GlcNAcβ1-3/6GalNAc, Neu5Acα2-6Galβ1-3GalNAcβ1-4Galα1-3Galβ1-4Glc, Neu5Acα2-6Galβ1-4GlcNAcβ1-3Galβ1-4Glc, Neu5Acα2-6Galβ1-3GalNAcβ1-3Galα1-4Galβ1-4Glc, Neu5Acα2-6Galβ1-3GlcNAcβ1-3Galβ1-4Glc, Neu5α2-6Galβ1-4GlcNAcβ1-3GalNAcα, Neu5Acα2-6Galβ1-4GlcNAcβ1-3Gal~1-3GalNAcα, Neu5Acα2-6GalNAc(β1-3Gal)β1-4Galβ1-4Glc, and Neu5Acα2-6GalNAc(β1-3Gal-)β1-3Galα1-4Galβ1-4Glc, α-Dystroglycan, asialoglycoprotein, sialyl Lewis (for use against norovirus), Neu5Ac(α2-3)Gal(β1-4)Glc, Neu5Acα2Me, dextran sulphate, heparin, chondrotin sulphate B, GalNAcβ1-4Galβ1-4Glcβ1-1Cer, Galβ1-3GalNAcβ1-4Galβ1-4Glcβ1-1Cer, Galβ1-3GalNAcβ1-4(NeuAcα2-3)Galβ1-4Glcβ1-1Cer, dextran, sialylated glycolipids, Lewis$^{A}$, fibronectin, laminin, collagen I, collagen III, NeuAcα2-3Galβ1-4GlcNAc, NeuGcα2-3Galβ1-4GlcNAc, NeuAcα2-6Galβ1-4GlcNAc, NeuAcα2-3Galβ1-4GlcNAc, NeuAc(α2-3)Gal, N-acetyl-9-O-NeuAc(α2-3)Gal, amphotericin B, Fucα2GalβGlcNAc, Manα3Manα6Man, Galα4Gal, NeuAc (α2-3) Galβ3GalNAc, NeuAc (α2-8), GalNAcβ4Galβ, GlcNAc, GlcNAcβ4GlcNAc, NeuAc(α2-3)Galβ4Glc, NeuAc(α2-3)Galβ4GlcNAc, Fucα2Galβ3(Fucα4)Gal, Man, Galβ4Glc(NAc), $[NeuAc(\alpha2\text{-}3)]_{0,1}$, Galβ4GlcNAcβ3Galβ4GlcNAc, L-Fuc, Galβ3Glc(NAc)β3Galβ4Glc, and Galα4Galβ4Glc, GT1b, GQ1b, GD1a, phosphatidylethanolamine, unsaturated fatty acids, synaptotagmins I and II, digalactosylceramide, Lewis$^{a}$, Asialo-GM1, lactosylceramide, and N-acetyllactosamine glycans, or a combination thereof.

In some implementations, the kit also includes instructions for making at least one liposome displaying binding targets on an outer surface of the liposome, and wherein the cholesterol is about 15 to 30 mol % of the liposome.

EXAMPLES

The present examples are non-limiting implementations of methods to prepare multivalent compositions of the present technology and their use. Exemplary, non-limiting components of a LSTc liposome composition are presented in FIG. 2A.

Example 1

Formation of LSTc Liposome

Purification of LSTc

LSTc was either obtained from a commercial source (Dextra, Reading, UK) or purified from milk.

Frozen bovine milk was thawed and centrifuged at 4,000×g for 10 min at 4° C. The upper fatty layer was discarded and the lower aqueous layer was mixed with 2 volumes of ethanol and kept at 4° C. overnight. Precipitate was removed by centrifugation at 12,000×g for 10 min at 4° C. The supernatant was dried under nitrogen at room temperature and then reconstituted with 0.2 volumes of fresh 20% methanol and stored at −20° C. until use. LSTc was separated from other oligosaccharides by subjecting the reconstituted solution to a dual stage purification, wherein the first step was size exclusion to remove high molecular weight material and to exchange the sample into a suitable buffer and the second step was a weak anion exchange purification using ammonium formate as the eluting agent. Fractions were monitored by mass spectrometry. LSTc fractions were pooled and lyophilized. Purity of sample was assessed using capillary electrophoresis.

Glycolipid Synthesis

Materials and Methods 1,2-dioleoyl-sn-glycero-3-phosphoethanolamine (DOPE) was purchased from Avanti Polar Lipids, Inc. and N-(FMOC-13-amino-4,7,10-trioxa-tridecyl)succinamic acid (linker) was purchased from Polypeptide Laboratories, San Diego. LSTc were purchased from Prozyme and Accurate Chemical and Scientific Corporation. Ethyl-3-[3-dimethylaminopropyl]carbodiimide hydrochloride (EDC) was purchased from Sigma-Aldrich (St. Louis, Mo.). Commercial reagents were used without further purification. Thin layer chromatography (TLC) was performed on silica gel coated glass plates. Column chromatography was performed using silica gel 60 Å. $^{1}H$ NMR spectra were obtained using a 600 MHz Bruker instrument at 22° C.; the chemical shifts values are reported in 'δ' and coupling constants (J) in Hz. Mass spectrometry was performed using both 4800 MALDI-MS and MALDI-TOF (Voyager DE-STR, Applied Biosystems). Solvent evaporations were performed on a rotary evaporator under reduced pressure at 30-35° C. All other synthetic lipids were purchased as solutions in chloroform (Avanti Polar Lipids, Alabaster, Ala.) including: DOPC (1,2-dioleoyl-sn-glycero-3-phosphocholine), DOPG (1,2-dioleoyl-sn-glycero-3-[phospho-rac-(1-glycerol)] (sodium salt)), and DOPE-NBD (1,2-dioleoyl-sn-glycero-3-phosphoethanolamine-N-(7-nitro-2-1,3-benzoxadiazol-4-yl)(ammonium salt)). Cholesterol (purity ≥99%, MW 386.65) was purchased dry (Sigma-Aldrich, St. Louis, Mo.) and dissolved in chloroform. Chloroform was >99.8% pure, stabilized with ethanol (Acros Organics, Morris Plains, N.J.), ethanol was 200 proof (Goldshield Chemical Co., Hayward, Calif.), hydrochloric acid was certified ACS plus (Fisher Scientific, Pittsburgh, Pa.) and all water used was ultra-purified (MilliQ Al 0, Millipore, Bilerica, Mass.).

Step-1: Conjugation of Lipid with FMOC Containing Linker

Figure 2:
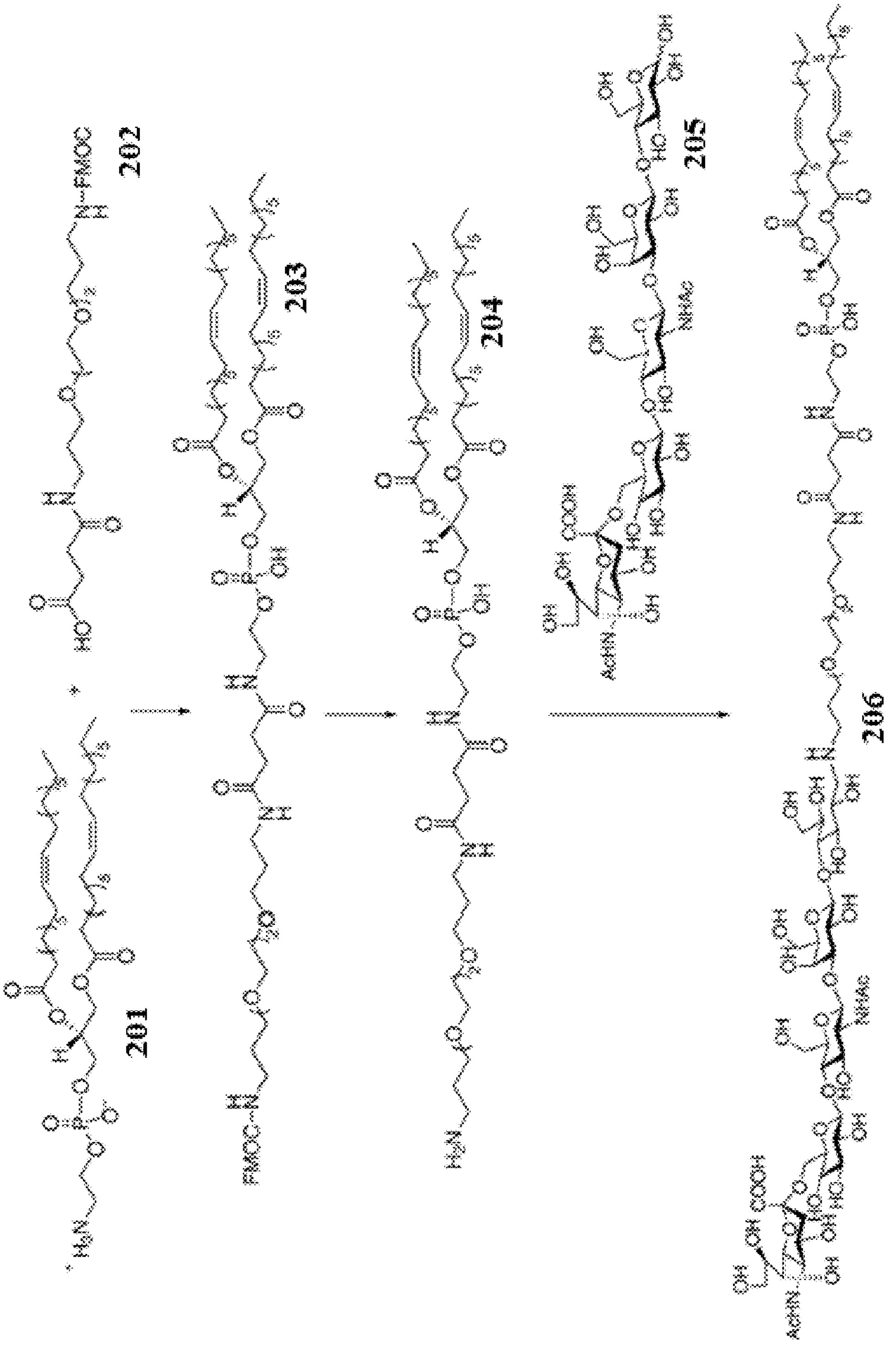
FIG. 2A is an exemplary, non-limiting summary of LSTc liposome components.
FIG. 2B is an exemplary, non-limiting diagram of a chemical synthesis pathway for LSTc-DOPE.

Referring to FIG. 2B, commercially available amine linked unsaturated phospholipid, DOPE 201, was attached with FMOC-protected linker acids 202 using EDC as coupling reagents at room temperature. 1 g of DOPE was dissolved in 10 mL of $CHCl_3$. 2 g of FMOC and 2 gm EDC was added to the solution and stirred for 4 hour at room temperature.

The completion of the reaction was monitored by TLC using $MeOH/CHCl_3$. The crude substance was extracted using dichloromethane and water. The combined organic layer was dried by rotavap to remove dichloromethane and purified by column chromatography (gravity) using silica gel and $MeOH/CHCl_3$ as solvent.

After purification the product solution was concentrated to remove all the organic solvent and dried by under vacuum. The purified and dried product 203 was characterized by NMR spectroscopy and MALDI-TOF mass spectroscopy.

Step-2: Removal of FMOC Group from the Lipid-Linker-FMOC

The FMOC deportation was carried out by secondary amine and formation of the amine linked product with the disappearance of FMOC group was also monitored by TLC.

Referring to FIG. 2B, the purified product from Step 1 203 was dissolved in 30 mL of DMF. 10 mL of piperidine was added and stirred at room temperature for about 4-10 h. The completion of the reaction was monitored by TLC using $MeOH/CHCl_3$ The crude substance was extracted using dichloromethane and water. The combined organic layer was dried by rotavap to remove dichloromethane and purified by column chromatography (gravity) using silica gel and $MeOH/CHCl_3$ as solvent. After purification the product solution was concentrated to remove all the organic solvent and dried by under vacuum.

The purified and dried product 204 was characterized by NMR spectroscopy and MALDI-TOF mass spectroscopy. Subsequently, the purified and characterized amine-linker-lipid conjugate was taken for the conjugation with free non-reducing sugar aldehyde (LSTc) via reductive beta elimination reaction.

Step 3: Reaction of LSTc with Amine-Linker-Lipid from Step 2

The conjugation of LSTc 205 and the amine-linker-lipid conjugate 204 was carried out at 60° C. with the presence of minimum acids.

Referring to FIG. 2B, 250 mg of the amine-linker-lipid 204 (from step 2) was dissolved in 4 ml of DMSO. 300 mg of sodium cyanoborohydride was added and the mixture was stirred at 60° C. for 5 minutes. After stirring, 500 µl of acetic acid was added, and the mixture was stirred for another 5 minutes. 10 mg LSTc 205 was added to the mixture directly and stirred for 4 h at 60° C. After completion of the reaction the crude substance was cooled to room temperature and quenched with 100 ml of $CHCl_3$.

The crude mixture was purified by a two-step procedure. Initially the crude substance was purified by column chromatography using silica gel. After purification by column chromatography, the substance was further purified by HPLC purification.

HPLC conditions: (a) C18 column in reverse phase mode; (b) the products were injected with mixture of water and acetonitrile (7:3); (c) Solvent A: water, solvent B: acetonitrile; (d) Gradient: 20-100% of acetonitrile/water over 2 hours. The fraction in each 5 minute gap was collected and dried by speed-vac and freeze drier.

The MALDI-MS of each fraction was determined to determine the retention time of elution of the product based on the column and HPLC instrument.

In some implementations, the purified and characterized product was further purified. The final purified product was dried by speed-vac and freeze dried and stored at −20° C.

The purified product 206 was characterized by MALDI-MS spectroscopy to obtained the final glycolipid.

Step 4: DMB-HPLC Quantification

LSTc incorporation into glycolipid was quantified by HPLC as described by Klein et al.; briefly, glycolipid or standard was treated with 2N glacial acetic acid at 80° C. for 5 hours then dried by centrifugal evaporation. Samples were treated with 30 µl 1,2-diamino-4,5-methylene dioxybenzene (DMB) labeling mixture (1.6 mg 1,2-diamino-4,5-methylenedioxybenzene dihydrochloride, 3.1 mg sodium hydrosulfite, 58 µl β-mercaptoethanol, 82 µl glacial acetic acid per ml) at 50° C. for 2.5 h in the dark. Samples were diluted with 20 µl ddH20, and analyzed by reverse phase HPLC using a TSKgel ODS-120T column (Tosoh Corp., South San Francisco, Calif.) running 7% methanol in water. Fluorescence of the DMB-SA complex 1s detected at ex373/em448.

Liposome Formation

Gas-tight syringes (Hamilton Co., Reno, Nev.) and 4 mL borosilicate glass vials with Teflon-lined caps (National Scientific, Rockwood, Tenn.) were thoroughly cleaned then rinsed 10× with 100% ethanol and then 10× with chloroform. Vials were soaked in 300 mM HCl for 1.5 h and then rinsed thoroughly with water, 3× with ethanol, and 3× with chloroform. Residual solvent was evaporated under a filtered stream of dry nitrogen gas. LSTc-glycolipids and a mixture of lipids were mixed and deposited in the clean vials using clean syringes.

Figure 9:
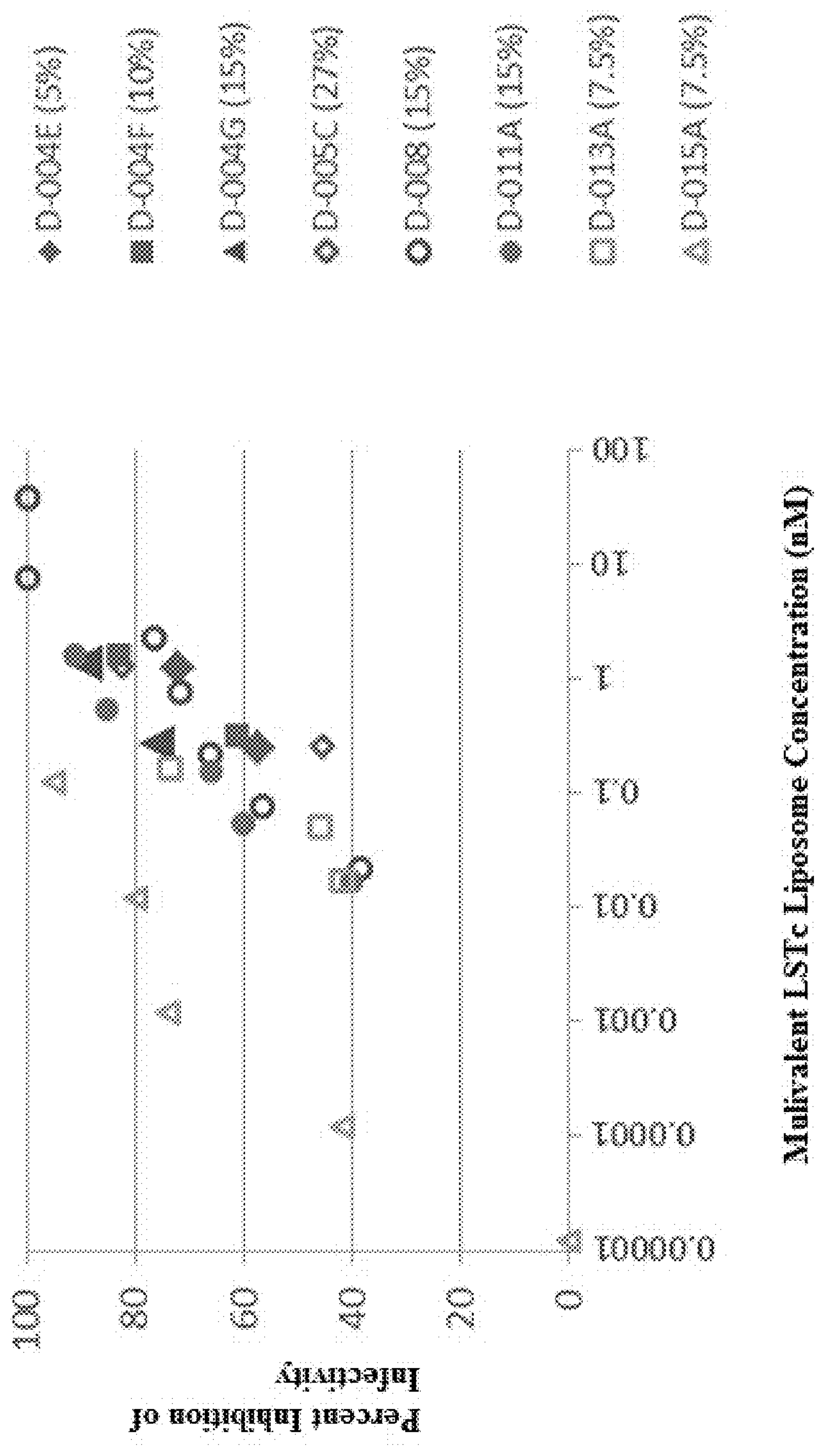
FIG. 9 is a graph showing a comparison of in vitro activity of various LSTc liposome batches. Various LSTc liposome batches containing 5, 7.5, 10, 15, or 27 mol % LSTc-DOPE were tested for their ability to inhibit PR/8 infection of MDCK cells.

Various batches of LSTc liposome composition were made with 5-27 mol % of LSTc-DOPE. LSTc-liposome inhibitory efficacy did not increase significantly when the LSTc concentration was increased beyond 7.5 mol % (FIG. 9). LSTc liposome preparations with 15 or 27 mol % LSTc had roughly the same activity (FIG. 9). The results suggest a limit to the number of binding targets can be appropriately displayed from the liposome surface and/or interact with the virus, bacteria, or toxin.

In some implementations, the final lipid mixture includes between about 1 to 30 mol %, or between about 3 to 27 mol %, or between about 6 to 24 mol %, or between about 9 to 21 mol %, or between about 12 to 18 mol % of glycolipids.

In some implementations, the final lipid mixture that includes between about 50 to 84 mol %, or between about 55 to 80 mol %, or between about 60 to 75 mol %, or between about 65 to 70 mol % of additional lipids.

In some implementation, the final lipid mixture includes cholesterol and/or short-chained alcohols. In some implementations, the lipid mixture includes between about 10 to 35 mol %, or between about 15 to 30 mol %, or between about 18 to 27 mol %, or between about 21 to about 24 mol % of cholesterol. In some implementations, the cholesterol forms lipid rafts in the lipid bilayer.

In some implementations, the solvent for the glycolipid is water. In some implementations, the above mixtures were mixed at room temperature.

Solvent was evaporated under a filtered stream of dry nitrogen gas while manually rotating the vial until only a thin layer of a lipid film remained on the inner walls. Residual solvent was removed by placing uncapped vials in a desiccator (Dry Seal, Wheaton, Millville, N.J.), then followed by application of reduced pressure for 24 hours using an oil-free diaphragm vacuum pump (Gast, Benton Harbor, Mich.).

Aqueous lipid solutions were made by hydrating the lipid film in 150 mM phosphate buffered saline (PBS) (140 mM NaCl, 8.5 mM $NaH_2PO_4$, 1.5 mM $Na_2HPO_4$, pH 7.4) and vortexing for 2 min in 30 second intervals. The lipid solution was then subjected to 10 rapid cycles of freeze-thawing by submersion in liquid nitrogen and 70° C. water, respectively, to break apart multilamellar structures.

The lipid solution was extruded through 200 nm pores. In some implementations, extrusion consisted of 10 passes through an aluminum oxide membrane using a Lipex™ Thermobarrel Extruder (Northern Lipids, Burnaby, BC, Canada). In an alternative implementation, extrusion consisted of 21 passes through a polycarbonate membrane using a Liposo-Fast-Basic Extruder (Avestin; Ottawa, ON, Canada). Before extrusion, the Extruders were cleaned and primed with 150 mM phosphate buffered saline (8.5 mM $Na_2HPO_4$, 1.5 mM $NaH_2PO_4$, and 140 mM NaCl) at pH 7.6. Priming the Liposo-Fast-Basic Extruder consisted of rising all parts with the phosphate buffer solution and passing 500 μl of phosphate buffer through the extruder 21 times. Priming the Lipex™ Thermobarrel Extruder consisted of rising all parts with the water and passing 5 ml of phosphate buffer through the extruder 5 times.

After the final pass, samples were collected in a clean vial, sealed with a Teflon-lined cap, and stored at 4° C. until use. Lipid concentration post-extrusion relative to pre-extrusion was determined by fluorimetry. Typical recoveries were 50% with the Lipex™ Thermobarrel Extruder and ~80% with the LiposoFast-Basic Extruder.

Diameter and polydispersity of the liposomes were determined by dynamic light scattering (Zetasizer Nano; Malvern Instruments, Worcestershire, UK) specifying a lipid refractive index of 1.480 and a dispersant (when PBS) refractive index of 1.332. Measurements were taken using 40 μL disposable cuvettes at room temperature (20° C.) and a back-scattering angle of 173 degrees. Average liposomes were 90 to 150 nm in diameter with a polydispersity of 0.05 to 0.2. Multivalent liposomes were stored at 4° C. for 12 months and were stable over this period, retaining their anti-influenza properties.

Example 2

Multivalent LSTc Liposome Binds to Various Influenza Strains

The ability of purified multivalent LSTc liposomes to bind to different strains of influenza viruses (IVA) was examined.

Materials and Methods

Viral strains—Influenza A/Puerto Rico/8/34 virus (PR/8, H1N1) was provided by Susan Swain (University of Massachusetts, Worcester, Mass.). Influenza A/Philippines X-79 ($H_3N_2$) was provided by Richard Dutton (University of Massachusetts, Worcester, Mass.). Influenza A/Aichi/68 (X-31, H3N2) and Sendai virus (Cantell Strain) were purchased from Charles River Laboratories (North Franklin, Conn.). Influenza A/Beijing/262/95 ($H_1N_1$) was purchased from Meridian Life Science (Saco, Me.). Influenza viruses and Sendai virus were originally grown in the allantoic cavity of embryonated chicken eggs. Influenza viruses were stored at −80° C. prior to use and titered on Madin-Darby canine kidney (MDCK) cells.

Hemagglutination inhibition assay—Red blood cells (RBCs) were isolated from normal human peripheral blood, blood type 0. Whole blood was washed in sterile PBS three times to remove serum. Packed RBCs were diluted 1:30 in sterile PBS and stored at 4° C. prior to use. All procedures involving human subjects were approved by the University of Massachusetts Medical School Committee for the Protection of Human Subjects in Research and in accordance with the Declaration of Helsinki HA titers for each virus were determined on RBCs prior to inhibition studies as described in Choi et al., *Chemistry & Biology:* 3, 97-104 (1996). For hemagglutination inhibition (HAI) assays, liposome samples were diluted two-fold in PBS. Four HA units of virus in 25 μl of PBS were added to all dilutions. Samples were incubated for 30 minutes at room temperature. 50 μl of diluted RBCs were added to the wells and incubated for an additional hour at room temperature to allow agglutination. The HAI titer is the reciprocal of the last dilution of liposomes that results in non-agglutinated RBCs.

Results

Standard hemagglutination inhibition (HAI) assay was performed to assess binding of LSTc liposomes to influenza A/Puerto Rico/8/34 (PR/8, H1N1). Percentage of LSTc at the liposome surface represents the mole percentage of lipid monomers used in liposome synthesis reaction. IAV binds to SA on the surface of RBCs, causing hemagglutination. LSTc liposomes provide an alternative SA binding option for IAV and will inhibit hemagglutination when present in sufficient quantity. The ability of LSTc liposomes to inhibit hemagglutination can be expressed either as the HAI titer (i.e., the reciprocal of the last dilution of liposomes required to inhibit hemagglutination) or as the concentration (molarity of SA) that results in 90% inhibition (IC90). For PR/8, liposomes with 7.5 mol % LSTc had HAI titers of 256 and an IC90 of 0.041 μM SA, and liposomes with 5 mol % LSTc had HAI titers of 128 and an IC90 of 0.04 μM SA (see Table 1). Liposomes containing 1 mol % LSTc did not inhibit hemagglutination at the highest concentration tested, 0.52 μM SA. Control liposomes, i.e., liposomes without LSTc, tested at similar lipid concentrations as the LSTc liposomes, did not inhibit hemagglutination. Monovalent LSTc liposomes, used at $5\times10^5$ μM did not inhibit hemagglutination (see Table 1). Additionally, the activity of LSTc liposomes containing either 10, 20 or 30 mol % LSTc by HAI against various strains of IAV were tested, however, no significant increase in HAI titers compared to liposomes containing 7.5 mol % LSTc was observed (data not shown).

TABLE 1

| Inhibition of PR/8 infection by LSTc liposomes | | |
|---|---|---|
| Mol % LSTc liposomes | HAI Titer | $IC_{90}$ (μM SA) |
| 0 | No inhibition | N/A |
| 1 | No inhibition | >0.52 |
| 5 | 128 | 0.04 |
| 7.5 | 256 | 0.041 |
| Monovalent LSTc | No inhibition | >500,000 |

To test the specificity of LSTc liposomes, HAI assay with several additional strains of IAV as well as the related RNA virus, Sendai virus (SeV) were performed. SeV is a Paramyxoviridae family virus that binds specifically to α2-3 linked SA, which is not present in the LSTc liposomes. LSTc liposomes containing 7.5 mol % LSTc inhibited all strains of IAV tested: A/Philippines/2/82/X-79 (Philippines, H3N2) with an HAI titer of 16 (IC90=0.98 SA), X-31 (A/Aichi/68, H3N2) with an HAI titer of 32 (IC90=0.26 μM SA), and Beijing (H1N1) with an HAI titer of 64 (IC90=0.11 μM SA) (see Table 2). However, 7.5 mol % LSTc liposomes did not inhibit SeV agglutination (see Table 2), demonstrating that the observed LSTc liposome binding is specific for α2-6 linked SA binding and is not a non-specific binding event.

TABLE 2

| LSTc Liposome Inhibition of Various Viral Strains | | |
|---|---|---|
| Virus | HAI Titer | $IC_{90}$ (μM SA) |
| Philippines H3N2 | 16 | 0.98 |
| X-31 H3N2 | 32 | 0.26 |
| Beijing H3N2 | 64 | 0.11 |
| PR/8 HlNl | 256 | 0.041 |
| Sendai | No inhibition | >84 |

The results show that LSTc liposomes of the present technology specifically bind to human IAV and are useful in inhibiting the infectivity of influenza virus. The results show that the compositions of the present technology are useful in the treatment or prevention of viral infection.

Example 3

Multivalent LSTc Liposome Blocks Influenza Infection In Vitro

The ability of purified multivalent LSTc liposomes, in solution, to block influenza A/Puerto Rico/8/34 (PR/8, H1N1) infection of MDCK cells was examined.

Method and Materials

MDCK cells were obtained from the American Type Culture Collection (ATCC, Manassas, Va.) and were cultured in Eagle's minimal essential medium (MEM) with 10% fetal bovine serum (FBS), 2 mM L-glutamine, 2 mM Penicillin/Streptomycin (Pen/Strep), 0.1 mM non-essential amino acids and 1 mM sodium pyruvate. A549 cells were obtained from ATCC and cultured in Dulbecco's modified Eagle's medium (DMEM) with 10% FBS and 2 mM Pen/Strep. Vero cells were obtained from ATCC and cultured in DMEM with 10% FBS and 2 mM Pen/Strep.

MDCK cells were seeded into 12-well plates and incubated at 37° C. for 24 hours to form monolayers. Liposome samples were diluted to the desired concentration in sterile PBS-1% bovine serum albumin (BSA, Sigma-Aldrich, St. Louis, Mo.) in a final volume of 225 μl. IAV was diluted to 300 PFU/mL and mixed 1:1 (v/v) with liposome samples and incubated at 37° C. for 30 min. MDCK cells were washed twice with PBS-1% BSA and samples were added to wells in duplicate (200 μl per well). Samples were incubated at 37° C. for 1 hour on MDCK cells. Cells were washed with PBS-1% BSA and overlaid with freshly prepared 0.5% agar in DMEM-F12 and incubated at 37° C. for 48 hours. Cells were fixed and stained with anti-hemagglutinin antibody MAB8261 (Millipore, Billerica, Mass.). Plaques were visualized with anti-mouse horseradish peroxidase-conjugated secondary antibody (BD Biosciences, San Jose, Calif.) and developed with peroxidase substrate kit (Vector Laboratories, Burlingame, Calif.). Viral plaques in the MDCK monolayer were counted and the PFU/mL was determined.

Results

To test the impact of LSTc liposomes on IAV infectivity, PR/8 was co-incubated with either LSTc liposomes or control liposomes, i.e., without LSTc, prior to infection of MDCK cells. Increasing concentrations of LSTc liposomes inhibited infectivity of PR/8 (FIG. 3A), while control liposomes did not inhibit infection of MDCK cells by PR/8. The molarity of SA in the solution was calculated by multiplying the mole percent input of LSTc-DOPE glycolipids by the total lipid concentration. At 1 nM SA, all LSTc liposomes displayed weak inhibition. As the total concentration of SA increased, i.e., an increased mole percentages of LSTc on the liposome surface, the greater the inhibition of PR/8 infectivity, see FIG. 2A. LSTc liposomes with 1 mol % LSTc inhibited weakly, blocking only 22±5.6% of PR/8 at 515 nM SA. LSTc liposomes at 5 mol % inhibited weakly at low concentrations of LSTc, but increasing the concentration of these LSTc liposomes had a more pronounced inhibitory effect, inhibiting 73±10% of PR/8 at 1,000 nM SA. LSTc liposomes at 7.5 mol % blocked PR/8 infection to the largest extent, inhibiting PR/8 almost completely at 1,000 nM SA, 93.8±1.3% compared to control liposomes (FIG. 3A).

The results show the dose-dependent inhibition of influenza infection by LSTc liposomes. The results also show that the density of LSTc displayed on the surface of each liposome at a given concentration of LSTc affects the extent of viral inhibition. For example, when each series of LSTc liposomes was diluted to 100 nM of total SA and challenged with PR/8, 7.5 mol % LSTc liposomes inhibit to a greater degree than LSTc liposomes with either 1 or 5 mol % LSTc (FIG. 2A). The inhibition occurs despite the fact that the LSTc liposomes with a higher density of LSTc per liposome have fewer liposomes in solution at equimolar concentrations of LSTc. LSTc liposomes with denser LSTc are more efficient at inhibiting influenza.

The infectivity inhibition of LSTc liposomes having more than 7.5 mol % LSTc was tested against several strains of IAV. There was no significant increase of inhibition from liposomes with up to 30 mol % LSTc as compared to 7.5 mol % LSTc (data not shown). These results were similar to the finding that LSTc liposomes with more than 7.5 mol % did not increase HAI titers of IAV.

Inhibition of infectivity by LSTc liposomes at 7.5 mol % LSTc against additional IAV strains was tested. LSTc liposomes at 7.5 mol % inhibited all the additional IAV strains in a dose dependent manner. LSTc liposomes inhibited Philippines up to 58.3±3.4% at 1,000 nM SA. FIG. 3B. At 5,250 nM SA, LSTc liposomes at 7.5 mol % inhibited infectivity of X31 by 47.3±13.5% and infectivity of Beijing by 82.3±5.9%. Control liposomes lacking LSTc did not inhibit any of these strains. FIG. 3B. LSTc liposomes displayed high avidity for influenza in both the HAI and infectivity assays. LSTc liposomes were compared with monovalent LSTc at SA concentrations well in excess of the estimated SA concentrations for LSTc-containing liposomes. FIG. 3B. However, 74,000 nM monovalent LSTc did not inhibit the infectivity of either PR/8 (FIG. 3A) or Philippines (data not shown). At this high concentration, monovalent LSTc was expected to bind to both PR/8 and Philippines HA during the pre-incubation period.

The results show that LSTc liposomes of the present technology are useful in inhibiting the infectivity of influenza virus. The results show that the compositions of the present technology are useful in the treatment or prevention of viral infection.

Example 4

LSTc Liposomes do not Prevent Infection of Respiratory Syncytial Virus

The specificity of LSTc liposomes was examined by testing its ability to bind to respiratory syncytial virus (RSV). The ability of liposomes to block RSV infection of Vero cells was tested.

Method and Materials

Multivalent LSTc liposomes were prepared using the method described in Example 1.

Respiratory syncytial virus (RSV) strain A2 was grown in Vero cells in 5% fetal bovine serum (FBS), cell debris was frozen at −80° C. and subsequently titered on Vero cells.

Vero cells were grown to confluence in 24-well plates. Liposome samples were diluted to the desired concentration in serum-free DMEM in a final volume of 130 μL. RSV was diluted to 1,000 PFU/mL and mixed 1:1 (v/v) with liposome samples and incubated at 37° C. for 30 minutes. Vero cells were prewashed in serum-free DMEM before addition of 100 μL of sample, in duplicate. After one hour of infection, cells were washed with DMEM-10% FBS and incubated in DMEM-10% FBS and 2 mM Pen/Strep for three days at 37° C. Cells were fixed with 80/20 (v/v) acetone/PBS and stained with anti-F and anti-G glycoprotein antibodies (MAB8599 and MAB858, respectively; 1:1000 dilution, Millipore, Billerica, Mass.). RSV plaques were visualized and quantified as for IAV.

Results

RSV interacts with cellular heparin sulfate for attachment and infectivity and has not been reported to interact with SA receptors. 7.5 mol % LSTc liposomes or control liposomes were co-incubated with RSV prior to infection of Vero cells. LSTc liposomes did not affect RSV infectivity (FIG. 3B), even at a SA concentration of 10,000 nM, an amount that inhibits nearly 100% of PR/8 influenza. The lack of inhibition, along with the lack of hemagglutination inhibition of SeV (see Example 3 and Table 2), demonstrates the LSTc liposomes specifically inhibit via α2-6 linked SA.

These results suggest that binding targets can have a great degree of specificity and can target specific viruses, bacteria, or toxins, or a group of related viruses, bacteria, or toxins. The results show that the compositions of the present technology are useful in the treatment or prevention of viral or bacterial infection and reducing or preventing effects of a toxin.

Example 5

LSTc Liposomes Block Viral Growth of IAV in MDCK Cells

The ability of purified multivalent LSTc liposomes to inhibit viral growth in MDCK cells was examined.

Method and Materials

MDCK cells were seeded into 24-well plates and allowed to grow to confluence overnight at 37° C. MDCK monolayers were washed with PBS-1% BSA, and treated with 7.5 mol % LSTc liposomes ranging in concentration from 1 to 1,000 nM LSTc or control liposomes, at lipid concentrations equivalent to the 1,000 nM LSTc liposome treatment, for 30 minutes at 37° C. Treated MDCK cells were then infected at a multiplicity of infection (MOI) of 0.01 or 0.001 of PR/8 diluted in PBS-1% BSA without removal of liposome solution. The cells were incubated for one hour at 37° C. After incubation, the supernatant was removed and MDCK cells were washed with PBS-1% BSA. Viral growth medium (0.5 mL) with identical liposome treatment as during the infection step was added. After 24 hours, supernatants were taken and virus growth was measured by plaque assay (as described in Example 3).

Results

Figure 4:
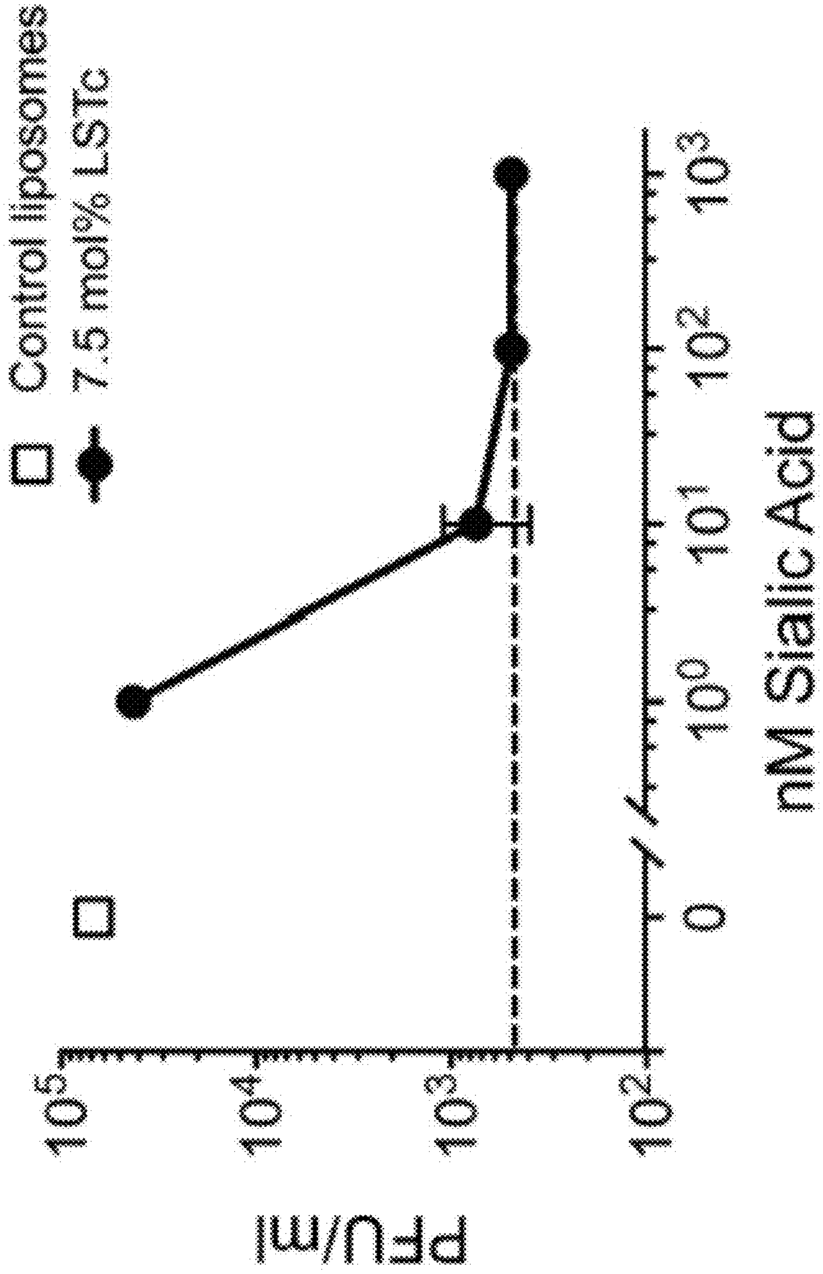
FIG. 4 is a graph showing inhibition of influenza replication by LSTc liposomes. Control (0% mol LSTc) or 7.5 mol % LSTc liposomes were added to confluent monolayers of MDCK cells 30 minutes before infection with PR/8 (MOI 0.01). After infection, cells were incubated in the presence of control or LSTc liposomes for 48 hours. Viral growth was measured by plaque forming unit assay and plotted as PFU/mL, versus total LSTc concentration present in the solution. Control liposomes did not inhibit influenza growth (open squares); however increasing concentrations of 7.5 mol % LSTc liposomes inhibited PR/8 infectivity (filled circles). The dotted line denotes the limit of detection of the assay. Data shown is representative of two experiments, each with similar results.

The amount of virus recovered from wells treated with highly concentrated LSTc liposomes was significantly reduced compared to wells with control liposomes, or with PR/8 and assay medium alone (FIG. 4). Infected MDCK cells treated with 100 or 1,000 nM LSTc liposomes had viral titers below the limit of detection, which was over 100-fold less than control liposome-treated cells (LSTc liposomes 2.7±0 vs. control liposomes 4.8±0.07; $P<0.001$, based on $\log_{10}$-transformed PFU/mL data) (data not shown). 10 nM LSTc liposomes also significantly inhibited PR/8 replication (2.8±0.2 vs. control liposomes 4.8±0.07; $P<0.01$) (FIG. 4). LSTc liposomes diluted to 1 nM LSTc or less did not prevent PR/8 replication (4.6±0.04 vs. control liposomes 4.8±0.07; $P=0.069$).

These results show that adhesion of viral particles to LSTc liposomes depletes the amount of free virus capable of infecting in successive rounds of replication, and that this interaction is long-lasting because the bound virus is not cleared in this in vitro system. The results show that the compositions of the present technology are useful in the treatment or prevention of viral infection.

Example 6

LSTc Liposomes Extend Survival of Mice Infected with Lethal Dose of IAV

The ability of multivalent LSTc liposomes to increase survival of mice infected with lethal dose of IAV examined.

Methods and Materials

LSTc liposomes (at 7.5 mol % and 15 mol % LSTc) or control liposomes were co-incubated with 1,000 plaque forming units (PFU) of PR/8 or the equivalent amount of control liposomes in a final volume of 30 μL at 37° C. for 30 minutes. Samples were stored on ice until use. The dose of PR/8 typically causes 90% lethality ($LD_{90}$) in C57BL/6 mice following intratracheal delivery. Female C57BL/6 wild-type mice were purchased from the Jackson Laboratory (Bar Harbor, Me.). Mice were 8 to 10 weeks of age at the time of infection. Mice were infected intratracheally with 30 μL of sample and monitored daily. Mice were scored as deceased when found dead or were clearly imminently moribund, in which case they were euthanized.

Results

Figure 5:
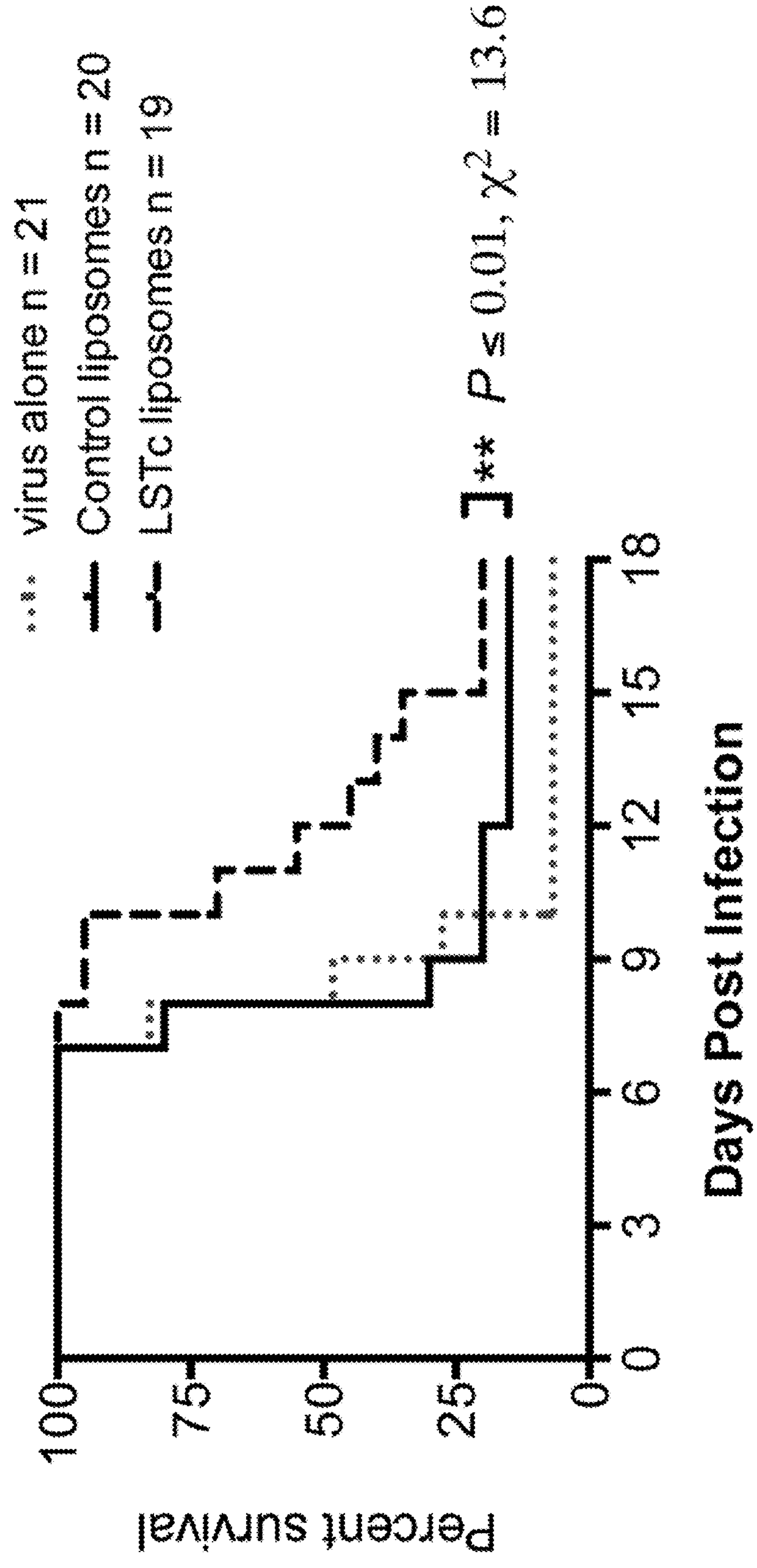
FIG. 5 is a graph showing that LSTc liposomes extend survival in mice following lethal IAV challenge. 1,000 PFU of PR/8 was incubated with control or LSTc liposomes at 37° C. for 30 minutes, and then used for intratracheal infection of C57BL/6 mice. Mice were monitored daily for survival. Mice that received LSTc liposomes and PR/8 (dashed black line) had a 33% increase of mean survival time post infection as compared to mice that received control liposomes and PR/8 (solid black line) or PR/8 alone (gray dotted line). The LSTc liposome and PR/8 treated mice survival advantage was statistically significant ($\chi^2$=13.6, P≤0.01; n≥19 for each strain). Data shown are combined from three independent experiments, each having similar results.

Mice that received control liposomes and 1,000 PFU of PR/8 died at the same rate as mice that received 1,000 PFU of PR/8 alone (FIG. 5, median survival of 8 days for both groups, Log Rank test, $\chi^2$=0.01, P=0.9). However, mice that received LSTc liposomes and 1,000 PFU of PR/8 had significantly extended survival, with a median survival of 12 days compared to 8 days for mice that received control liposomes and 1,000 PFU of PR/8 (Log Rank test, $\chi^2$=13.6, P≤0.01), resulting in a 33.3% mean increase in lifespan post-infection (FIG. 5). The median survival and survival curve slope was reproducible over multiple experiments (see FIG. 5, which represents the sum of three independent experiments with a combined n≥19 mice for each group). The results show that LSTc liposomes significantly extend survival of mice challenged with a $LD_{90}$ of IAV and that the inhibition observed in vitro (see Example 3) extends to a physiological infection setting in vivo. Additionally, LSTc liposomes may form long-lasting interactions with viral particles, even in the presence of the mucociliary system, lung surfactants, and resident professional phagocytes. No apparent toxicity was observed in uninfected mice that were administered LSTc liposomes and monitored for three weeks (data not shown).

The results show that LSTc liposomes of the present technology are useful in inhibiting the infectivity of influenza virus. The results show that the compositions of the present technology are useful in the treatment or prevention of viral infection.

Example 7

LSTc Liposomes Co-Localize with IAV and Inhibits Binding of IAV at the Surface of A549 Human Lung Epithelial Cells The ability of multivalent LSTc liposomes to co-localize with IAV and inhibit binding of IAV at the surface of A549 human lung epithelial cells was examined.

Methods and Materials

Adherent A549 cells were detached with 0.25% Trypsin/2.21 mM EDTA. Cells were washed twice with PBS, enumerated using a hemocytometer, and transferred to 96-well round-bottom plate (Costar, Washington D.C.) at 50,000 cells per well. Recombinant influenza A/WSN/33 with AlexaFluor 647 covalently attached to the HA protein via sortase (WSN HA-647) was prepared, as described in Popp et al., PLoS Pathogens 8; e1002604 (2012), and stored at 4° C. prior to use.

WSN HA-647 and LSTc liposomes were co-incubated for 30 minutes. WSN HA-647 was tested at 1.3, 6.5 and 13 HA units with 1000 nM, 7.5 mol % LSTc liposomes, diluted in PBS-1% BSA in a final volume of 50 μl. Control liposomes without LSTc were diluted to the same lipid concentration as LSTc liposomes. Cells were treated with virus/LSTc liposome mixtures for 15 minutes at 37° C. before being fixed with formalin (final concentration 1%). Cells were analyzed using a BD LSR II flow cytometer and FlowJo version 9.4.11 (TreeStar software).

Confocal microscopy—30 HA units of WSN HA-647 were absorbed onto glass coverslips overnight, then treated with either 7.5 mol % LSTc liposomes or control liposomes, both containing NBD-labeled lipids. LSTc liposomes were diluted to 1,000 nM LSTc in a final volume of 50 μL; control liposomes were diluted to the same lipid concentration as the LSTc liposomes. LSTc liposomes or control liposomes were incubated on the WSN HA-647 coverslips for 30 minutes at 4° C. and washed three times with PBS-1% BSA before imaging. Images were taken on a Leica SP2 AOBS confocal laser-scanning microscope with a 63× objective using the Leica Confocal Software (version 2.6.1). Multichannel images were obtained by sequential scanning with only one laser active for each scan to avoid cross-excitation. Overall brightness and contrast of images were optimized using Image J.

Results

Figure 6:
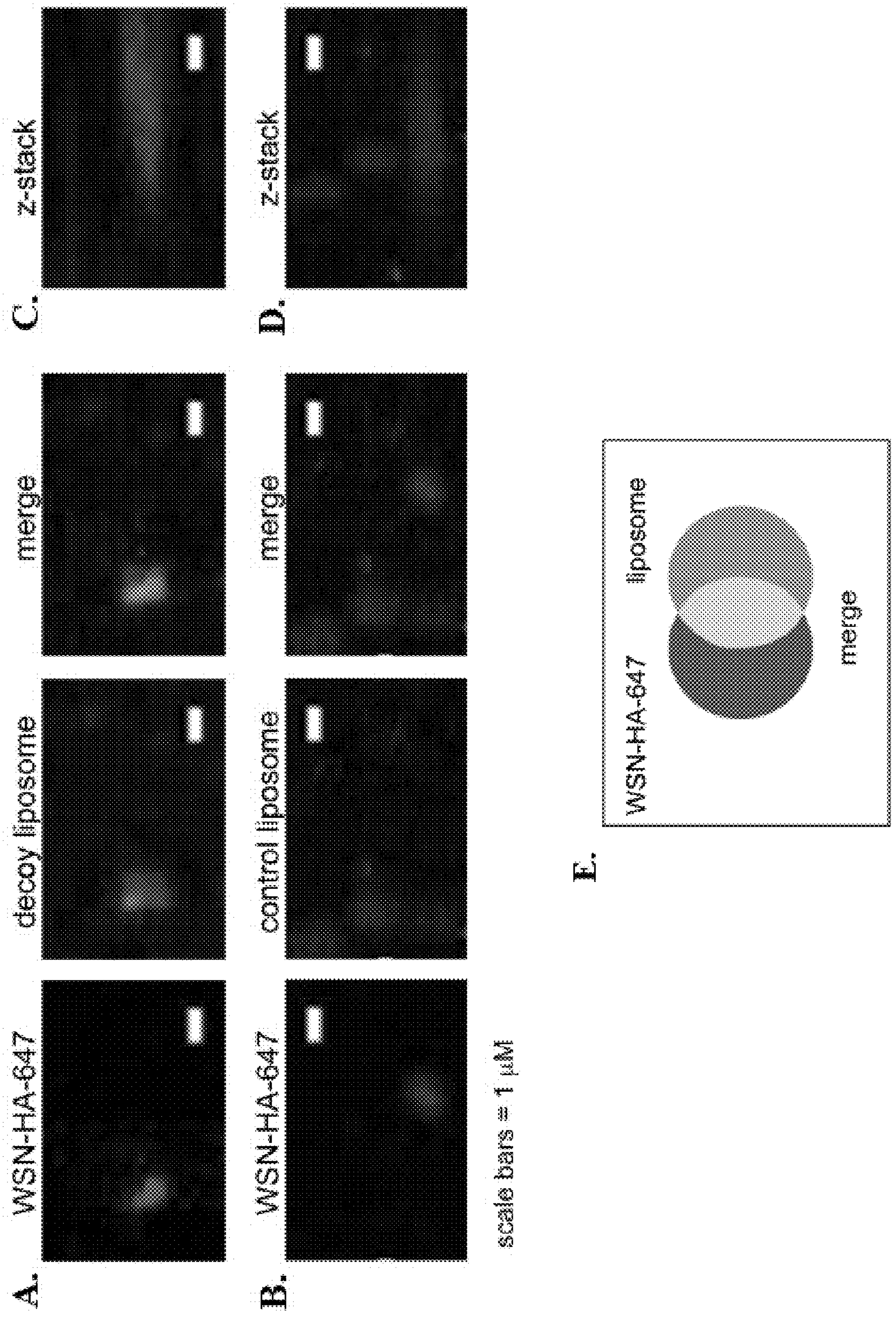
FIG. 6A-D are images showing that LSTc liposomes bind directly to influenza A virus. Immunofluorescent Z-stack images were obtained of WSN HA-647 and fluorescent control or LSTc liposomes, viewed from above (FIGS. 6A-B) or rotated 37 degrees (FIGS. 6C-D).
FIG. 6E is a diagram showing Van Steensel's cross-correlation function (CCF) coefficient analysis of FIGS. 6A and 6B. The CCF is the Pearson's coefficient of WSN HA-647 and liposomes at each pixel shift in the x dimension; this calculation is based on a representative field of 45 by 45 μm.
FIG. 6F is a graph showing the CCF. LSTc liposomes (open circles) significantly correlate to WSN HA-647 (P<0.001), while control liposomes (black squares) do not (P=0.21).
Figure 6:
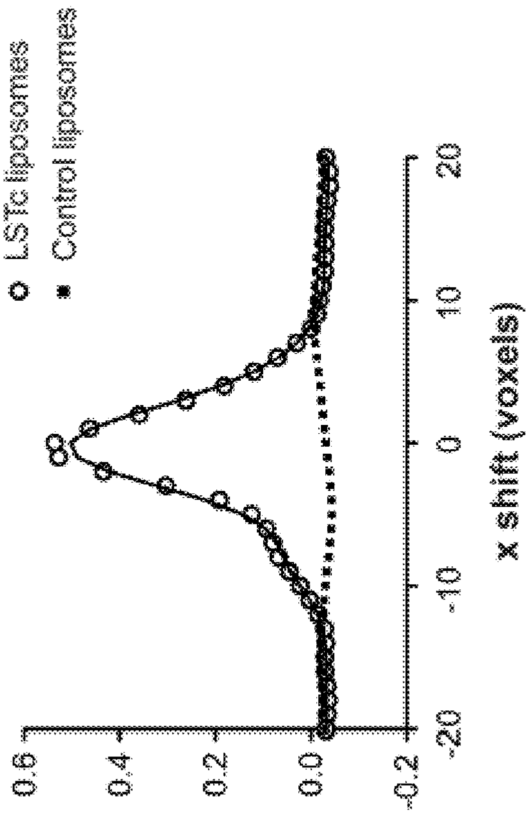

The inhibition of infection results from the direct binding of SA on LSTc liposomes to hemagglutinin. To directly observe contact between LSTc liposomes and influenza virus, a fluorophore was enzymatically attached onto viral particles for single virion tracking, as described in Popp et al., PLoS Pathogens 8; e1002604 (2012). WSN HA-647 was absorbed onto glass coverslips, then treated with either LSTc liposomes or control liposomes containing NBD-labeled lipids. WSN HA-647, LSTc liposomes, and control liposomes were each readily visible by confocal microscopy when fixed to glass coverslips (data not shown). Significant co-localization was observed when WSN HA-647 was treated with 1,000 nM SA LSTc liposomes with 7.5 mol % LSTc (FIGS. 6A and 6C, Pearson's correlation coefficient: r=0.423, P<0.01). Control liposomes did not co-localize with adhered virus (FIGS. 6B and 6D, Pearson's correlation coefficient r=0.023, P=0.87). FIG. 6E indicates the expected color change that indicates co-localization. Cross correlation analysis was used to validate the association of virus and LSTc liposomes. The cross-correlation function (CCF) establishes whether there is a relationship between two channels of a complex 3-D stacked image. FIG. 6F shows the CCF of WSN HA-647 treated with LSTc or control liposomes. The maximum CCF for LSTc liposomes is at 0 x-voxel displacement and follows the standard decay curve for x shift in both positive and negative directions. The distribution of LSTc liposomes and virus have significantly more overlap than control liposomes and virus, where the CCF does not peak at 0 x-voxel displacement, but peaks at 20 x-voxel shift with an r=0.023 and has a flat distribution of CCF throughout the x-voxel shift.

Figure 7:
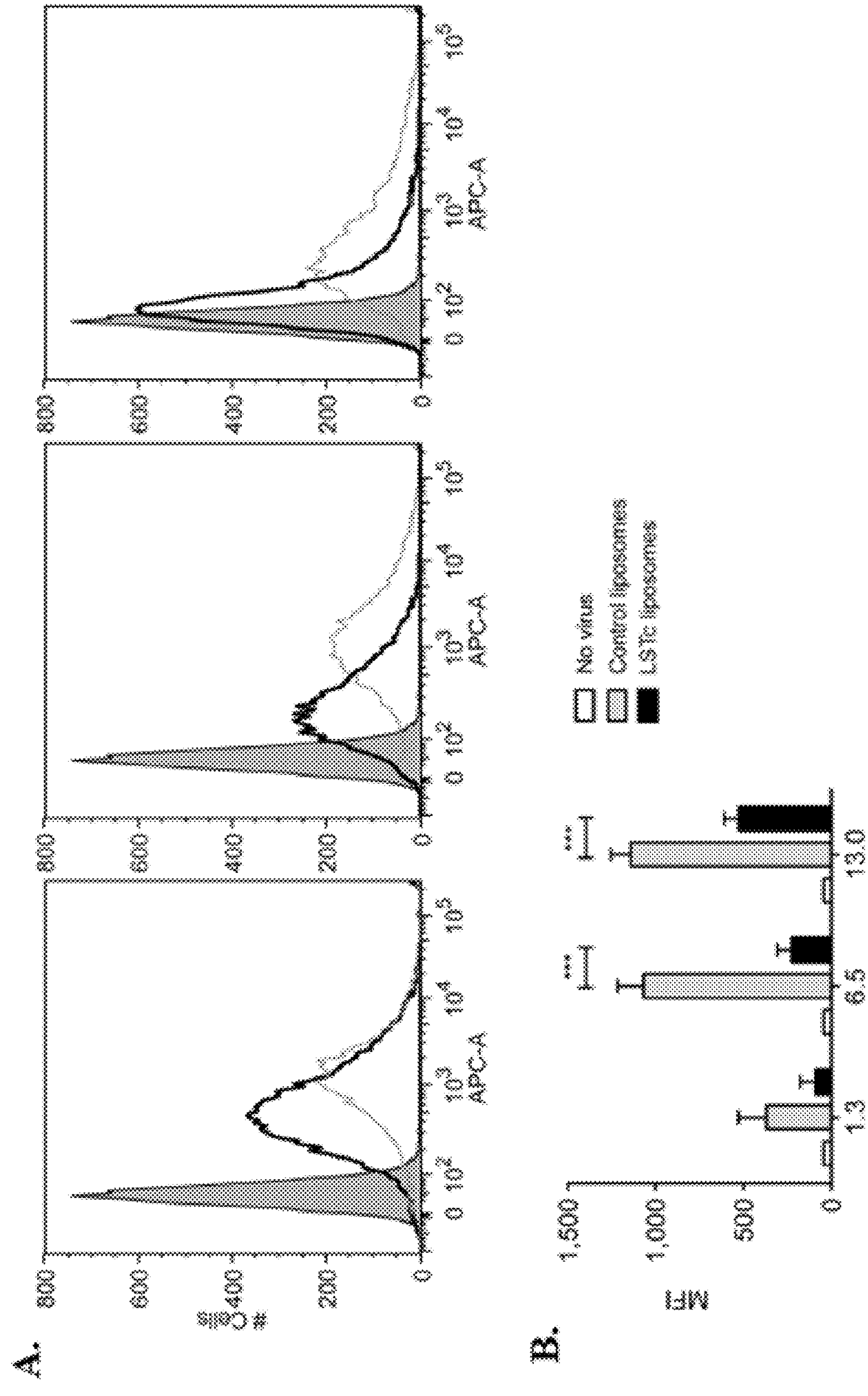
FIG. 7A shows flow cytometry plots showing that LSTc liposomes inhibit binding of influenza A virus to A549 cells. Representative flow cytometry plots of A549 cells treated with control liposomes (gray lines) combined with WSN HA-647 (1.3 HA units left panel, 6.5 HA units middle panel and 13 HA units right panel), LSTc liposomes combined WSN HA-647 (black lines) or A549 cells without virus (gray shaded). LSTc liposomes contained 7.5 mol % LSTc.
FIG. 7B is a graph showing mean fluorescence intensity (MFI) quantification of data in FIG. 7A, data presented as mean±S. E. M., P<0.001, LSTc liposomes versus control liposomes.

To further test the competitiveness of LSTc liposomes for IAV, human alveolar basal epithelial cells (A549 cells) were challenged with three different doses of WSN HA-647 combined with either LSTc liposomes or control liposomes. Mixtures of virus and liposome were added to A549 cells where free virus would bind to cells. Binding of virus at the single cell level was assessed by detection of WSN HA-647 by flow cytometry. WSN HA-647 in combination with control liposomes allowed a high degree of binding to A549 cells (FIG. 7A, gray lines). No significant shifts were noted for A549 cells challenged with control liposomes mixed with 1.3, 6.5, or 13 HA units of WSN-HA-647 (FIG. 7A, left, middle, and right panels). However, LSTc liposomes at 7.5 mol % LSTc reduced viral binding when challenged with WSN HA-647 (FIG. 7A, black lines). LSTc liposomes decreased 75%, 79% and 54% of binding when challenged with 1.3, 6.5, or 13 HA units of WSN HA-647 (FIG. 7A, left, middle, and right panels, respectively). At the 1.3 HA unit dose of WSN HA-647, the mean fluorescence intensities (MFI)±S.E.M. for control liposomes and LSTc liposomes were 369 (±158) and 89 (±88) (P=0.11) (FIG. 7B). The MFIs for 6.5 HA unit dose of WSN HA-647 were 1071 (±145) and 223 (±86) (P<0.001) and for 13 HA unit dose of WSN HA-647, 1142 (±113) and 522 (±89) (P<0.001) (FIG. 7B). Together with the infectivity data above, these results show that the LSTc liposomes competitively bind to influenza, block its adhesion to SA on uninfected cells thus blocking infection.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

What is claims is:

1. A composition comprising:

a first population of lipids, a second population of lipids, cholesterol, and two or more influenza A binding targets, wherein the influenza A binding targets are linked to the first population of lipids to form BT-lipids, wherein the BT-lipids, the second population of lipids, and cholesterols form a liposome, wherein the binding targets are displayed on the outer surface of the liposome, wherein the first population of lipids and the second population of lipids in the liposome have a phase transition temperature below 41° C., wherein the cholesterol comprises 15 to 30 mol % of the liposome.

2. The composition of claim 1, wherein the first population of lipids and the second population of lipids are the same.

3. The composition of claim 1, wherein the first population of lipids and the second population of lipids are different.

4. The composition of claim 1, wherein the two or more influenza A binding targets are selected from the group consisting of LSTc, α-5-N-acetyl-neuraminic acid (Neu5Ac), Neu5Acα2-3Galβ1-4GlcNAc, Neu5Acα2-6Galβ1-4GlcNAc, Neu5Acα2-3Galβ1-4GlcNAβ1-3Galβ14GlcNAc, Neu5Acα2-6Galβ1-4GlcNAcβ1-3Galβ1-4GlcNAc, Neu5Acα2-3Galβ1-4GlcNAcβ11-3Galβ1-4GlcNAcβ1-3Galβ1-4GlcNAc, Neu5Acα6Galβ4GlcNAcβ3Galβ4Glc, Neu5Acα3Galβ4GlcNAc, Neu5Acα6Galβ4GlcNAc, Neu5Acα3Gal, Neu5Acα6Gal, Neu5Acα3Galβ4Glc, Neu5Acα3Galβ3GlcNAc, Neu5Acα2-6Galβ1-4GlcNAcβ1-3Galβ1-4GlcNAc-, Neu5Acα2-6GalNAcβ1-4GlcNAcβ1-3GalNAcβ1-4GlcNAc-, Neu5Acα2-6GlcNAcβ1-3Galβ1-3/4GlcNAc-, Neu5Acα2-6Galβ1-4GlcNAcβ1-3Galβ1-3GalNAcα, Neu5Acα2-6Galβ1-4GlcNAcβ1-3Galβ1-4GlcNAcβ1-3Galβ1-3GalNAcα, Neu5Acα2-6GalNAcβ1-4GlcNAcβ1-3Galβ1-3GalNAcα, Neu5Acα2-6GalNAcβ1-4GlcNAcβ1-3GalNAcβ1-4GlcNAcβ1-3Galβ1-3GalNAcα, Neu5Acα2-6GalNAcα-β1-3Galα2-3Neu5Ac, Neu5Acα2-6Galβ1-4GlcNAcβ1-3/6GalNAcα, Neu5Acα2-6Galβ1-4GlcNAcβ1-3Galβ1-4GlcNAcβ1-3/6GalNAcα, Neu5Acα2-6GalNAcβ1-4GlcNAcβ1-3/6GalNAcα, Neu5Acα2-6GalNAcβ1-4GlcNAcβ1-3GalNAcβ1-4GlcNAcβ1-3/6GalNAcα, Neu5Acα2-6Galβ1-4GlcNAcβ1-6GalNAcα-β1-3Galα2-3Neu5Ac, Neu5Acα2-6Galβ1-4GlcNAcβ1-3/6GalNAcα-β1-3/6GlcNAcβ1-4Galα2-3/6Neu5Ac, Neu5Acα2-6GlcNAcβ1-3Galβ1-4GlcNAcβ1-3Galβ1-3GalNAc, Neu5Acα2-6GlcNAcβ1-3Galβ1-3GlcNAcβ1-3/6GalNAc, Neu5Acα2-6GlcNAcβ1-3Galβ1-4GlcNAcβ1-3/6GalNAc, Neu5Acα2-6Galβ1-3GalNAcβ1-4Galα1-3Galβ1-4Glc, Neu5Acα2-6Galβ1-4GlcNAcβ1-3Galβ1-4Glc, Neu5Acα2-6Galβ1-3GalNAcβ1-3Galα1-4Galβ1-4Glc, Neu5Acα2-6Galβ1-3GlcNAcβ1-3Galβ1-4Glc, Neu5α2-6Galβ1-4GlcNAcβ1-3GalNAcα, Neu5Acα2-6Galβ1-4GlcNAcβ1-3Gal-1-3GalNAcα, Neu5Acα2-6GalNAc(β1-3Gal)β1-4Galβ1-4Glc, Neu5Acα2-6GalNAc(β1-3Gal-)β1-3Galα1-4Galβ1-4Glc and a combination thereof.

5. The composition of claim 1, wherein the two or more influenza A binding targets are LSTc.

6. The composition of claim 1, wherein the first population of lipids is selected from the group consisting of 12:0 phosphatidylcholine (PC) (DLPC), 13:0 PC, 14:0 PC (DMPC), 15:0 PC, 16:0 PC (DPPC), 16:1 PC, 18:1c9 PC (DOPC), 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC (POPC), 16:0-22:6 PC, 18:0-14:0 PC, 18:0-18:1 PC, 18:1-16:0 PC, 18:1-18:0 PC, 12:0 phosphatidylglycerol (PG) (DLPG); 14:0 PG (DMPG), 16:0 PG (DPPG), 18:1 PG (DOPG), 16:0-18:1 PG (POPG), 14:0 phosphatidylserine (PS) (DMPS), 18:1 PS (DOPS), 16:0-18:1 PS (POPS), 12:0 phosphatidic acid (PA) (DLPA), 18:1 PA (DOPA), 16:0-18:1 PA (POPA), 12:0 phosphatidylethanolamine (PE) (DLPE), 18:1c9 PE (DOPE), 18:1t9 PE, 18:2 PE, 18:3 PE, 16:0-18:1 PE (POPE), and a combination thereof.

7. The composition of anyone of claim 1, wherein the first population of lipids is DOPE.

8. The composition of claim 1, wherein the second population of lipids is selected from the group consisting of 12:0 phosphatidylcholine (PC) (DLPC), 13:0 PC, 14:0 PC (DMPC), 15:0 PC, 16:0 PC (DPPC), 16:1 PC, 18:1c9 PC (DOPC), 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC (POPC), 16:0-22:6 PC, 18:0-14:0 PC, 18:0-18:1 PC, 18:1-16:0 PC, 18:1-18:0 PC, 12:0 phosphatidylglycerol (PG) (DLPG); 14:0 PG (DMPG), 16:0 PG (DPPG), 18:1 PG (DOPG), 16:0-18:1 PG (POPG), 14:0 phosphatidylserine (PS) (DMPS), 18:1 PS (DOPS), 16:0-18:1 PS (POPS), 12:0 phosphatidic acid (PA) (DLPA), 18:1 PA (DOPA), 16:0-18:1 PA (POPA), 12:0 phosphatidylethanolamine (PE) (DLPE), 18:1c9 PE (DOPE), 18:1t9 PE, 18:2 PE, 18:3 PE, 16:0-18:1 PE (POPE), and a combination thereof.

9. The composition of claim 8, wherein the second population of lipids are 18:1 lipids.

10. The composition of claim 1, wherein the second population of lipids is selected from the group consisting of DOPE, DOPC, DOPG, or a combination thereof.

11. The composition of claim 1, wherein the composition binds to a virus particle.

12. A composition of claim 1, wherein the BT-lipids comprises LSTc linked to DOPE and wherein the second population of lipids is selected from the group consisting of DOPE, DOPC, DOPG, or a combination thereof.

13. A method for treating or preventing influenza A infection comprising administering an effective amount of a liposome composition to a subject in need thereof, wherein the liposome composition comprises two or more influenza A binding targets, wherein the influenza A binding targets are linked to a first population of lipids to form BT-lipids, a second population of lipids, and cholesterols, wherein the BT-lipids, the second population of lipids, and cholesterols form a liposome, wherein the binding targets are displayed on the outer surface of the liposome, wherein the first population of lipids and the second population of lipids in the liposome have a phase transition temperature below 41° C., and wherein the cholesterol is about 15 to 30 mol % of the liposome.

14. The method of claim 13, wherein the first population of lipids and the second population of lipids are the same.

15. The method of claim 13, wherein the first population of lipids and the second population of lipids are different.

16. The method of claim 13, wherein the first and second population of lipids are selected from the group consisting of 12:0 phosphatidylcholine (PC), 13:0 PC, 14:0 PC, 15:0 PC, 16:0 PC, 16:1 PC, 18:1c9 PC (DOPC), 18:1t9 PC, 18:1c6 PC, 22:1c13 PC, 18:2 PC, 18:3 PC, 20:4 PC, 14:0-16.0 PC, 14:0-18:0 PC, 16:0-14:0 PC, 16:0-18:1 PC, 16:0-22:6 PC, 18:0-14:0 PC, 18:0-18:1 PC, 18:1-16:0 PC, 18:1-18:0 PC, 12:0 phosphatidylglycerol (PG); 14:0 PG, 16:0 PG, 18:1 PG (DOPG), 16:0-18:1 PG, 18:1 PS (DOPS) phosphatidylserine (PS), 16:0-18:1 PS, 12:0 phosphatidic acid (PA), 18:1 PA (DOPA), 16:0-18:1 PA, 12:0 phosphatidylethanolamine (PE), 18:1c9 PE (DOPE), 18:1t9 PE, 18:2 PE, 18:3 PE, 16:0-18:1 PE, or a combination thereof.

17. The method of claim 13, wherein the two or more influenza A binding targets are select from the group consisting of LSTc, α-5-N-acetyl-neuraminic acid (Neu5Ac), Neu5Acα2-3Galβ1-4GlcNAc, Neu5Acα2-6Galβ1-4GlcNAc, Neu5Acα2-3Galβ1-4GlcNAβ1-3Galβ14GlcNAc, Neu5Acα2-6Galβ1-4GlcNAcβ1-3Galβ1-4GlcNAc, Neu5Acα2-3Galβ1-4GlcNAcβ11-3Galβ1-4GlcNAcβ1-3Galβ1-4GlcNAc, Neu5Acα6Galβ4GlcNAcβ3Galβ4Glc, Neu5Acα3Galβ4GlcNAc, Neu5Acα6Galβ4GlcNAc, Neu5Acα3Gal, Neu5Acα6Gal, Neu5Acα3Galβ4Glc, Neu5Acα3Galβ3GlcNAc, Neu5Acα2-6Galβ1-4GlcNAcβ1-3Galβ1-4GlcNAc-, Neu5Acα2-6GalNAcβ1-4GlcNAcβ1-3GalNAcβ1-4GlcNAc-, Neu5Acα2-6GlcNAcβ1-3Galβ1-3/4GlcNAc-, Neu5Acα2-6Galβ1-4GlcNAcβ1-3Galβ1-3GalNAcα, Neu5Acα2-6Galβ1-4GlcNAcβ1-3Galβ1-4GlcNAcβ1-3Galβ1-3GalNAcα, Neu5Acα2-6GalNAcβ1-4GlcNAcβ1-3Galβ1-3GalNAcα, Neu5Acα2-6GalNAcβ1-4GlcNAcβ1-3GalNAcβ1-4GlcNAcβ1-3Galβ1-3GalNAcα, Neu5Acα2-6GalNAcα-β1-3Galα2-3Neu5Ac, Neu5Acα2-6Galβ1-4GlcNAcβ1-3/6GalNAcα, Neu5Acα2-6Galβ1-4GlcNAcβ1-3Galβ1-4GlcNAcβ1-3/6GalNAcα, Neu5Acα2-6GalNAcβ1-4GlcNAcβ1-3/6GalNAcα, Neu5Acα2-6GalNAcβ1-4GlcNAcβ1-3GalNAcβ1-4GlcNAcβ1-3/6GalNAcα, Neu5Acα2-6Galβ1-4GlcNAcβ1-6GalNAcα-β1-3Galα2-3Neu5Ac, Neu5Acα2-6Galβ1-4GlcNAcβ1-3/6GalNAcα-β1-3/6GlcNAcβ1-4Galα2-3/6Neu5Ac, Neu5Acα2-6GlcNAcβ1-3Galβ1-4GlcNAcβ1-3Galβ1-3GalNAc, Neu5Acα2-6GlcNAcβ1-3Galβ1-3GlcNAcβ1-3/6GalNAc, Neu5Acα2-6GlcNAcβ1-3Galβ1-4GlcNAcβ1-3/6GalNAc, Neu5Acα2-6Galβ1-3GalNAcβ1-4Galα1-3Galβ1-4Glc, Neu5Acα2-6Galβ1-4GlcNAcβ1-3Galβ1-4Glc, Neu5Acα2-6Galβ1-3GalNAcβ1-3Galα1-4Galβ1-4Glc, Neu5Acα2-6Galβ1-3GlcNAcβ1-3Galβ1-4Glc, Neu5α2-6Galβ1-4GlcNAcβ1-3GalNAcα, Neu5Acα2-6Galβ1-4GlcNAcβ1-3Gal-1-3GalNAcα, Neu5Acα2-6GalNAc(β1-3Gal)β1-4Galβ1-4Glc, and Neu5Acα2-6GalNAc(β1-3Gal-)β1-3Galα1-4Galβ1-4Glc, Dystroglycan, asialoglycoprotein, sialyl Lewis, Neu5Ac(α2-3)Gal(β1-4)Glc, Neu5Acα2Me, dextran sulfate, heparin, and a combination thereof.

* * * * *